(12) United States Patent
Kamatani et al.

(10) Patent No.: US 9,812,646 B2
(45) Date of Patent: Nov. 7, 2017

(54) ORGANIC COMPOUND AND ORGANIC LIGHT-EMITTING DEVICE AND DISPLAY APPARATUS HAVING THE SAME

(71) Applicant: CANON KABUSHIKI KAISHA, Tokyo (JP)

(72) Inventors: Jun Kamatani, Tokyo (JP); Shigemoto Abe, Yokohama (JP); Tetsuya Kosuge, Yokohama (JP); Takayuki Horiuchi, Tokyo (JP); Yosuke Nishide, Kawasaki (JP); Hirokazu Miyashita, Tokyo (JP); Kengo Kishino, Tokyo (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 401 days.

(21) Appl. No.: 14/432,690

(22) PCT Filed: Sep. 20, 2013

(86) PCT No.: PCT/JP2013/076455
§ 371 (c)(1),
(2) Date: Mar. 31, 2015

(87) PCT Pub. No.: WO2014/054552
PCT Pub. Date: Apr. 10, 2014

(65) Prior Publication Data
US 2015/0333267 A1    Nov. 19, 2015

(30) Foreign Application Priority Data
Oct. 2, 2012 (JP) ................................. 2012-220406

(51) Int. Cl.
*H01L 51/00* (2006.01)
*H01L 51/50* (2006.01)
(Continued)

(52) U.S. Cl.
CPC ........ *H01L 51/0054* (2013.01); *C07C 13/567* (2013.01); *C07C 15/38* (2013.01);
(Continued)

(58) Field of Classification Search
None
See application file for complete search history.

(56) References Cited

U.S. PATENT DOCUMENTS 7,429,425 B2 * 9/2008 Ikeda ................... C07C 13/567
257/40
8,115,378 B2 * 2/2012 Ionkin ................... C07C 15/62
257/40
(Continued)

FOREIGN PATENT DOCUMENTS

JP    2006-052323 A    2/2006
JP    2011-60878 A     3/2011
(Continued)

OTHER PUBLICATIONS

Marvel et al., Journal of the American Chemical Society, vol. 61, 894-897, Apr. 1939.

*Primary Examiner* — Robert S Loewe
(74) *Attorney, Agent, or Firm* — Canon U.S.A. Inc., IP Division

(57) ABSTRACT

A novel organic compound having high stability is provided. The organic compound is represented by Formula (1) described in claim 1:
In Formula (1), $R_1$ and $R_2$ each independently selected from a hydrogen atom, Substituent group A, and Substituent group B shown in claim 1, wherein at least one of $R_1$ and $R_2$ is selected from Substituent group A or Substituent group B; and $R_{11}$ and $R_{12}$ of a substituent belonging to Substituent group A are each independently selected from Substituent group B.

16 Claims, 1 Drawing Sheet

(51) Int. Cl.
| | |
|---|---|
| *G03G 15/04* | (2006.01) |
| *H05B 33/08* | (2006.01) |
| *C07D 333/76* | (2006.01) |
| *C07C 15/38* | (2006.01) |
| *C09K 11/06* | (2006.01) |
| *C07C 255/52* | (2006.01) |
| *C07C 13/567* | (2006.01) |
| *C07D 307/91* | (2006.01) |
| *C07D 307/92* | (2006.01) |
| *H05B 33/14* | (2006.01) |
| *C07D 307/77* | (2006.01) |
| *C09B 57/00* | (2006.01) |

(52) U.S. Cl.
CPC .......... *C07C 255/52* (2013.01); *C07D 307/77* (2013.01); *C07D 307/91* (2013.01); *C07D 307/92* (2013.01); *C07D 333/76* (2013.01); *C09B 57/00* (2013.01); *C09K 11/06* (2013.01); *G03G 15/04036* (2013.01); *H01L 51/0058* (2013.01); *H01L 51/504* (2013.01); *H01L 51/5024* (2013.01); *H05B 33/0896* (2013.01); *H05B 33/14* (2013.01); *C07C 2603/18* (2017.05); *C07C 2603/24* (2017.05); *C07C 2603/26* (2017.05); *C07C 2603/42* (2017.05); *C07C 2603/48* (2017.05); *C07C 2603/50* (2017.05); *C07C 2603/52* (2017.05); *C09K 2211/1007* (2013.01); *C09K 2211/1011* (2013.01); *C09K 2211/1088* (2013.01); *C09K 2211/1092* (2013.01); *H01L 51/0059* (2013.01); *H01L 51/0085* (2013.01); *H01L 51/5012* (2013.01); *H01L 51/5028* (2013.01); *H01L 51/5036* (2013.01)

(56) References Cited

U.S. PATENT DOCUMENTS

| | | | |
|---|---|---|---|
| 8,221,907 B2* | 7/2012 | Kawamura | C07C 13/567 313/504 |
| 8,580,400 B2* | 11/2013 | Kosuge | C07C 15/38 257/40 |
| 9,240,553 B2* | 1/2016 | Kosuge | H01L 51/0055 |
| 2007/0236137 A1* | 10/2007 | Funahashi | C07C 211/61 313/504 |
| 2009/0162693 A1 | 6/2009 | Ionkin | |
| 2009/0174313 A1* | 7/2009 | Nishimura | C09K 11/06 313/504 |
| 2010/0187517 A1* | 7/2010 | Nishimura | B82Y 10/00 257/40 |
| 2010/0283043 A1* | 11/2010 | Nishimura | C09K 11/06 257/40 |
| 2011/0001130 A1* | 1/2011 | Nishimura | C09K 11/06 257/40 |
| 2012/0013700 A1* | 1/2012 | Horiuchi | C07C 13/62 347/225 |

FOREIGN PATENT DOCUMENTS

| | | |
|---|---|---|
| JP | 2012-149012 A | 8/2012 |
| JP | 2012-156499 A | 8/2012 |
| JP | 2012-182127 A | 9/2012 |
| WO | 00/56691 A1 | 9/2000 |
| WO | 2010/107037 A1 | 9/2010 |
| WO | 2010/107097 A1 | 9/2010 |
| WO | 2010/116661 A1 | 10/2010 |
| WO | 2010-150694 A1 | 12/2010 |
| WO | 2011/019360 A1 | 2/2011 |

* cited by examiner

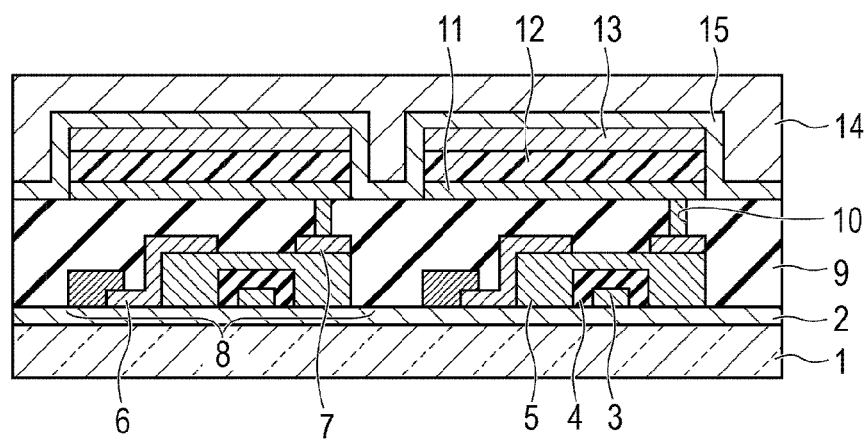

ORGANIC COMPOUND AND ORGANIC LIGHT-EMITTING DEVICE AND DISPLAY APPARATUS HAVING THE SAME

TECHNICAL FIELD

The present invention relates to a novel organic compound and an organic light-emitting device and a display apparatus including the organic compound.

BACKGROUND ART

An organic light-emitting device (also referred to as organic electroluminescent device or organic EL device) is an electronic element including a pair of electrodes and an organic compound layer disposed between the electrodes.

Electrons and holes are injected from the pair of electrodes into the organic compound layer to generate excitons of the organic light-emitting compound in the organic compound layer, and the organic light-emitting device emits light when the excitons return to the ground state.

The organic light-emitting devices have remarkably progressed recently and are characterized by low driving voltages, various emission wavelengths, rapid response, and reductions in size and weight of light-emitting devices.

In order to provide high-performance organic light-emitting devices, creation of compounds having excellent device lifetime characteristics is important. Accordingly, compounds suitable to organic light-emitting devices have been actively being created.

As compounds having aryl substituents at the 3-position or the 9-position of chrysene that have been created until now, for example, PTL 1 describes Compound 1-A shown below as an intermediate, and PTL 2 describes Compound 1-B shown below. As compounds having aryl substituents at the 2-position or the 8-position of chrysene, NPL 1 describes Compound 1-C shown below.

[Chem. 1]

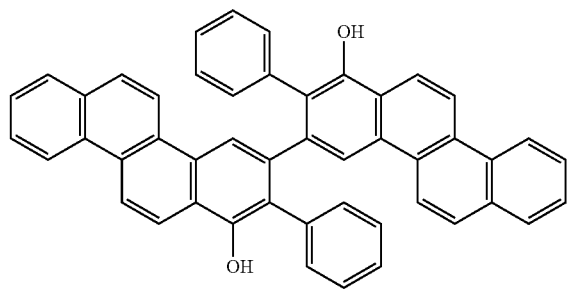 [SMILES: Oc1c(-c2ccccc2)c(-c2cc3c(ccc4c5ccccc5ccc34)c(O)c2-c2ccccc2)cc2c1ccc1c3ccccc3ccc21]

[Chem. 2]

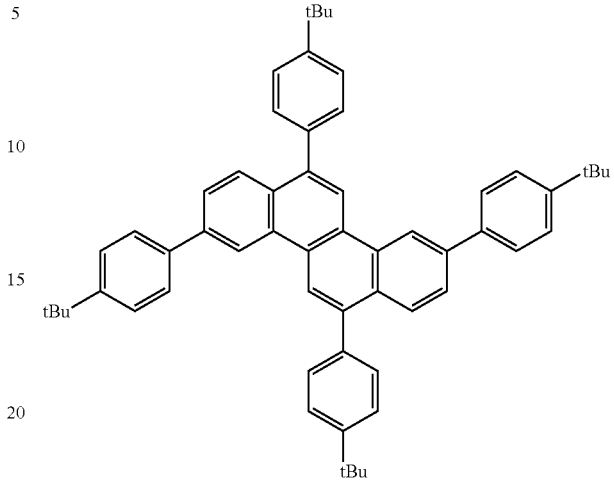

[Chem. 3]

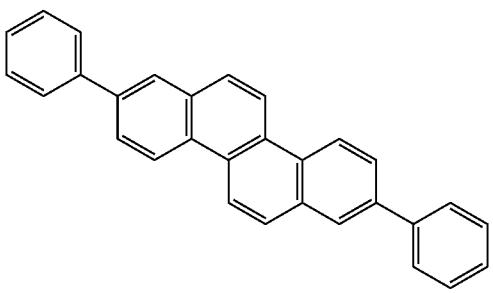 [SMILES: c1ccc(-c2ccc3c(ccc4c5ccc(-c6ccccc6)cc5ccc34)c2)cc1]

Compound 1-A has a substituent also at the 4-position, and therefore organic light-emitting devices including the compound have short device lifetimes.

Compound 1-B has a substituent also at the 6-position or the 12-position, and therefore organic light-emitting devices including the compound have short device lifetimes.

Compound 1-C has a substituent also at the 2-position or the 8-position, and therefore organic light-emitting devices including the compound have short device lifetimes.

Therefore, organic light-emitting devices including the compounds having such structures described in PTL 1 or 2 or NPL 1 cannot have high device lifetime characteristics.

CITATION LIST

Patent Literature

PTL 1 International Publication No. WO 2000/056691
PTL 2 U.S. Patent Application Publication No. 2009/0162693

Non Patent Literature

NPL 1 C. S. MARVEL and W. J. PEPPEL, Journal Of the American Chemical Society (1939), 61, 895-7

SUMMARY OF INVENTION

The present invention provides an organic compound that imparts high device lifetime characteristics to the organic light-emitting device including the organic compound. The present invention also provides an organic light-emitting device having a long device lifetime.

Accordingly, the present invention provides an organic compound represented by the following Formula (1):

[Chem. 4]

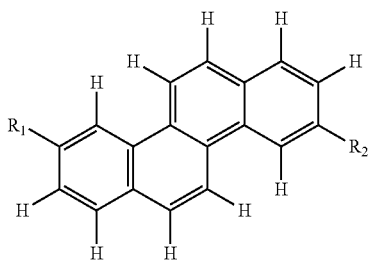

(1)

In Formula (1), R₁ and R₂ each independently selected from a hydrogen atom, Substituent group A, and Substituents belonging to group B shown below, wherein at least one of R₁ and R₂ is selected from Substituent group A or Substituent group B.

In Substituent group A, $R_{11}$ and $R_{12}$ are each independently selected from Substituent group B. Substituent shown in Substituent group A and Substituent group B are substituted or unsubstituted aryl groups and substituted or unsubstituted heterocyclic groups.

Advantageous Effects of Invention

The present invention can provide a highly stable organic compound and also provide an organic light-emitting device having a long device lifetime.

Further features of the present invention will become apparent from the following description of exemplary embodiments (with reference to the attached drawing).

BRIEF DESCRIPTION OF DRAWING

FIG. 1 is a schematic cross-sectional view illustrating an example of a display apparatus having organic light-emitting devices according to an embodiment of the present invention and active devices connected to the respective organic light-emitting devices.

DESCRIPTION OF EMBODIMENT

The organic compound according to the present invention is represented by Formula (1):

[Chem. 5]

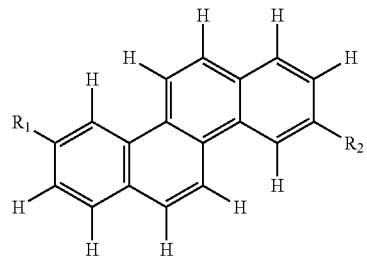

(1)

In Formula (1), $R_1$ and $R_2$ each independently selected from a hydrogen atom, Substituent group A, and Substituent group B shown below, wherein at least one of $R_1$ and $R_2$ is selected from Substituent group A or Substituent group B shown below.

In Substituent group A, $R_{11}$ and $R_{12}$ are each independently selected from Substituent group B.

[Chem. 6]

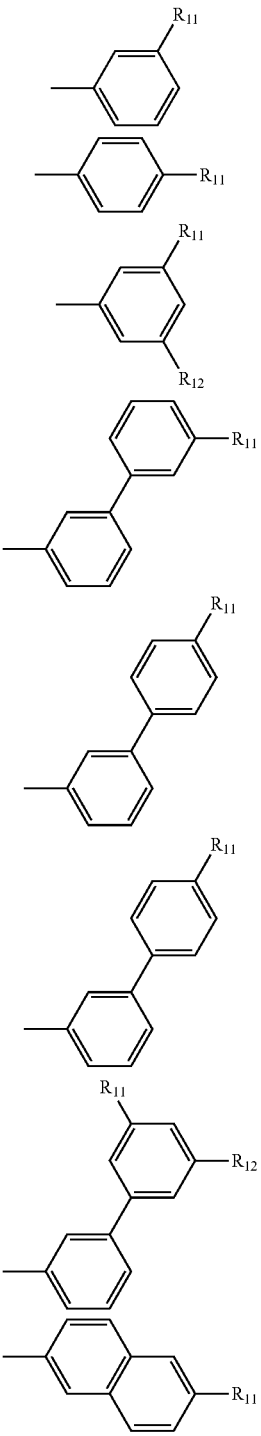

A

-continued
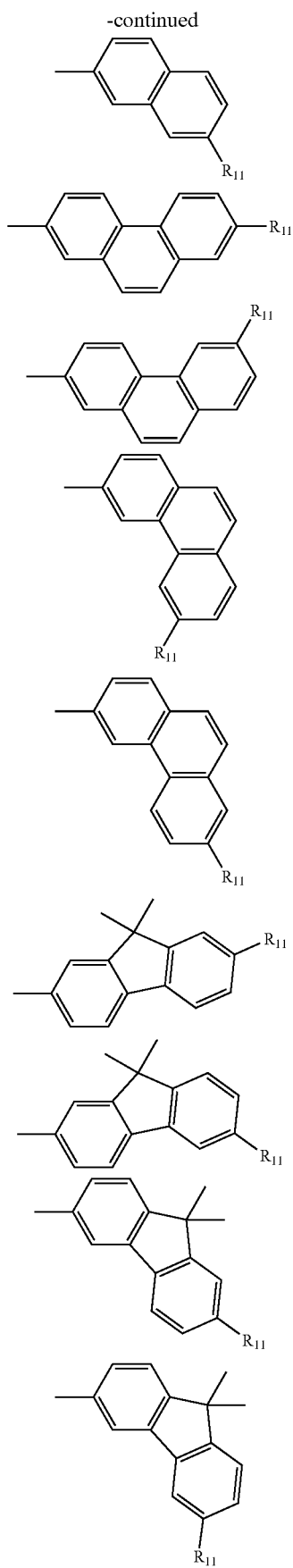
-continued
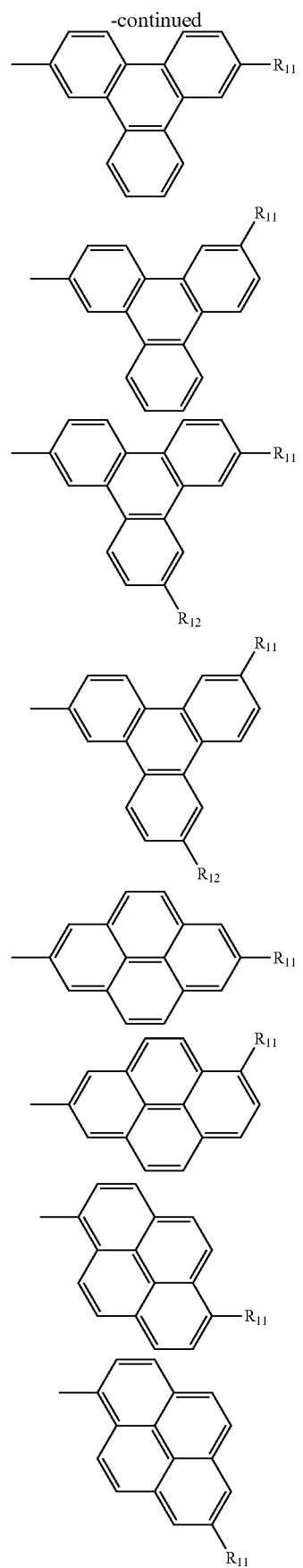

[Chem. 7]
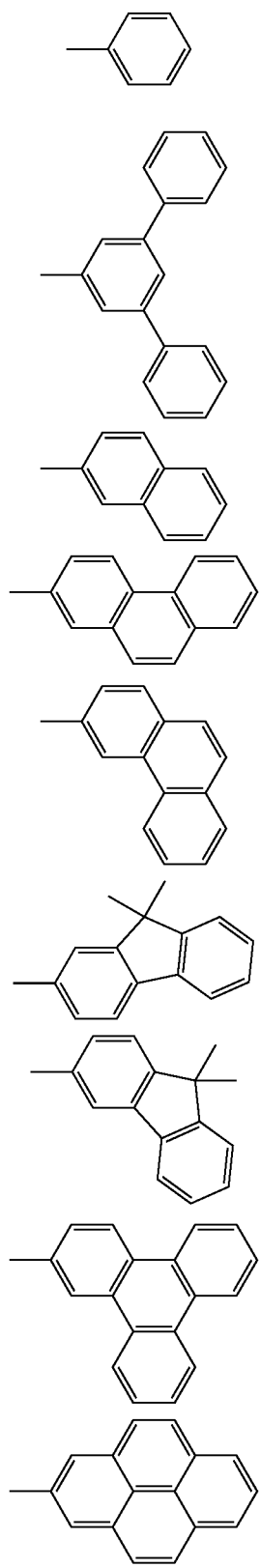
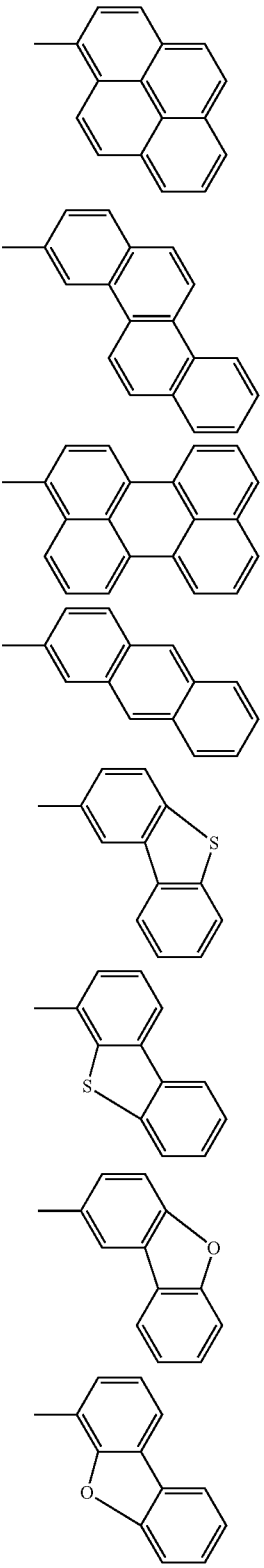
Each substituent belonging to Substituent group A or Substituent group B may have a halogen atom, a substituted or unsubstituted alkyl group, a substituted or unsubstituted alkoxy group, a silyl group, or a cyano group at a position other than the $R_{11}$ and $R_{12}$ substitution positions.

Each substituent belonging to Substituent group A is also referred to as A, and each substituent of Substituent group B is also referred to as B.

Examples of the halogen atoms of A and B include fluorine, chlorine, bromine, and iodine.

Examples of the alkyl groups of A and B include methyl, ethyl, normal propyl, isopropyl, normal butyl, tertiary butyl, secondary butyl, octyl, cyclohexyl, 1-adamantyl, and 2-adamantyl groups.

Examples of the alkoxy group of A and B include methoxy, ethoxy, propoxy, 2-ethyl-octyloxy, and benzyloxy groups.

In the organic compound according to the embodiment, the film-forming property is improved by introducing substituents into the basic skeleton, but introduction of too many substituents decreases the sublimability.

A high film-forming property can be confirmed by measuring the glass transition temperature. An organic light-emitting device including a compound having a high glass transition temperature can be a stable element. A stable element has a long device lifetime. A glass transition temperature is also referred to as Tg.

From this viewpoint, $R_1$ or $R_2$ in Formula (1) can be —B or -A-B. That is, $R_1$ or $R_2$ is only a substituent selected from Substituent group B or a complex substituent composed of a substituent selected from Substituent group A and a substituent selected from Substituent group B.

The basic skeleton in the embodiment is represented by the same structural formula as that of unsubstituted chrysene. The basic skeleton of the present invention can also be referred to as chrysene skeleton.

A method of synthesizing the organic compound according to the embodiment will now be described. The organic compound according to the embodiment can be synthesized in accordance with, for example, the following reaction scheme:

[Chem. 8]

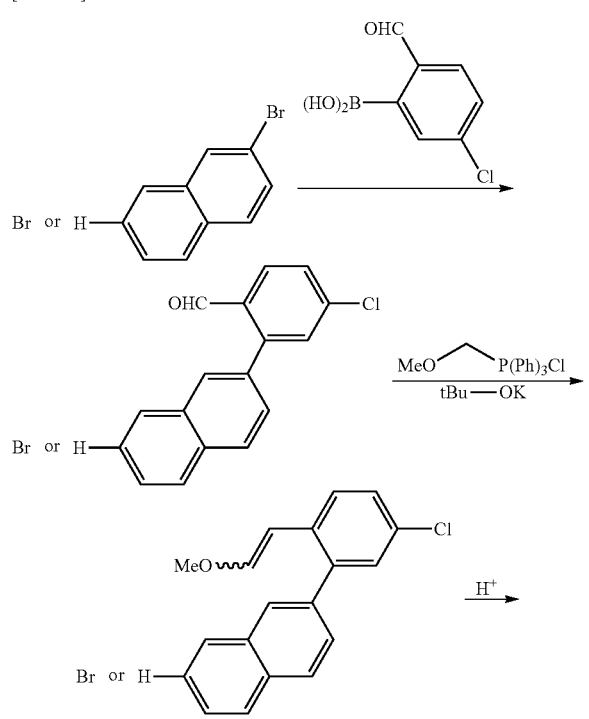

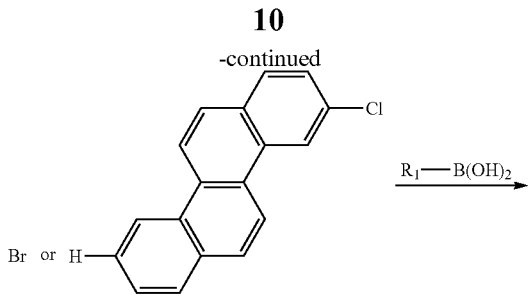

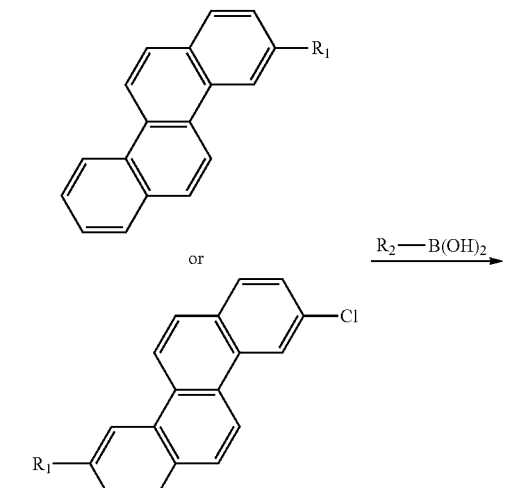

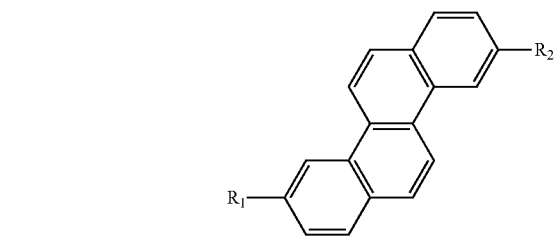

As shown in the synthetic scheme, the organic compound according to the embodiment can be synthesized.

Properties of the basic skeleton of the organic compound according to the embodiment will now be described.

The present inventors have focused on the basic skeleton and the substitution position in designing the organic compound represented by Formula (1). Specifically, high device lifetime characteristics are achieved by substituting at least either the 3-position or the 9-position of the chrysene skeleton and not substituting the other positions of the chrysene skeleton.

The properties of the organic compound according to the present invention will be described by comparing them with comparative compounds having similar structures to that of the organic compound of the present invention. Specifically, the comparative control compounds are represented by the following Formulae (2) to (4).

[Chem. 9]

(2)

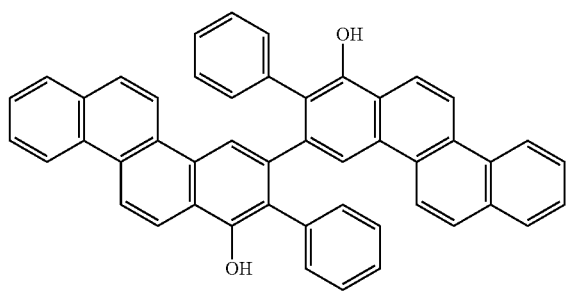

[Chem. 10]

(3)

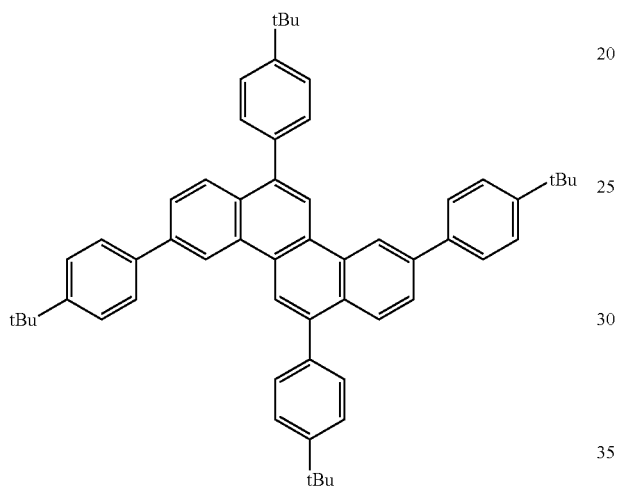

[Chem. 11]

(4)

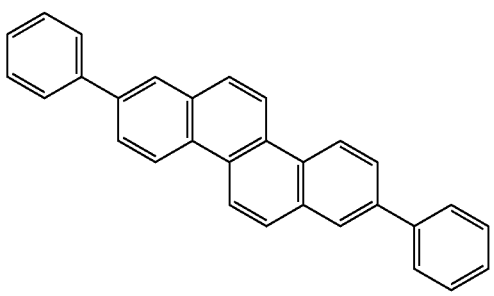

The organic compounds according to the present invention used for the comparison are the compound represented by following Formula (5), i.e., the chrysene skeleton represented by Formula (1) having chrysene at the 3-position, and the compound represented by the following Formula (6), i.e., the chrysene skeleton represented by Formula (1) having phenyl groups at the 3-position and the 9-position.

[Chem. 12]

(5)

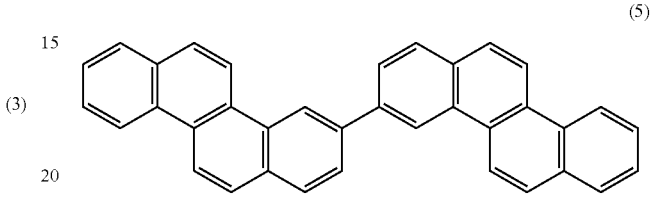

[Chem. 13]

(6)

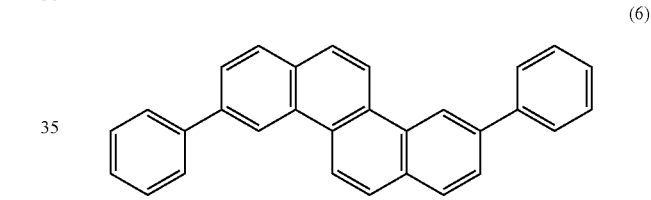

The present inventors have noticed that the lower molecular stability of the organic compounds represented by Formula (2) or (3) relative to that of the organic compounds represented by Formula (5) or (6) is caused depending on the substitution positions of the substituents in the chrysene skeleton.

The dihedral angle of the bond between the chrysene skeleton and an aryl group in the present invention was calculated. The calculation was performed based on the density functional theory, quantum chemical calculation at a B3LYP/6-31G* level. The results are shown in Table 1.

TABLE 1

| Name | Structural formula | Dihedral angle (°) | Bond length (Å) |
|---|---|---|---|
| 1-position phenyl group (7-position phenyl group) | | 58 | 1.492 |

TABLE 1-continued

| Name | Structural formula | Dihedral angle (°) | Bond length (Å) |
|---|---|---|---|
| 2-position phenyl group (8-position phenyl group) | | 38 | 1.484 |
| 3-position phenyl group (9-position phenyl group) | | 38 | 1.485 |
| 4-position phenyl group (10-position phenyl group) | | 55 | 1.496 |
| 5-position phenyl group (11-position phenyl group) | | 59 | 1.496 |
| 6-position phenyl group (12-position phenyl group) | | 58 | 1.492 |

As shown in Table 1, the dihedral angle between the chrysene skeleton and the aryl group in a stable structure is 38° when the aryl group is introduced at the 2-, 3-, 8-, or 9-position, whereas the dihedral angle is 50° or more when the aryl group is introduced at the 1-, 4-, 5-, 6-, 7-, 10-, 11-, or 12-position.

A compound in which groups are arranged so as to be nearly plane is stable. In the light of this point, a compound having a large dihedral angle, i.e., having a substituent at the 1-, 4-, 5-, 6-, 7-, 10-, 11-, or 12-position is less stable compared to a compound having a substituent at the 2-, 3-, 8-, or 9-position.

This relationship applies to the bond length between the chrysene skeleton and an aryl group. The compound having a large dihedral angle, i.e., having the aryl group at the 1-, 4-, 5-, 6-, 7-, 10-, 11-, or 12-position has a bond length of 1.49 Å or more, whereas the compound having a small dihedral angle, i.e., having the aryl group at the 2-, 3-, 8-, or 9-position has a bond length of less than 1.49 Å.

A longer bond length between carbon atoms leads to weak bonding and low stability.

A chrysene skeleton that is used as a charge-transporting material for transporting charges, such as organic EL materials, can have an aryl group from the viewpoint of amorphous properties.

In such a case, from the point of stability, the 1-, 4-, 5-, 6-, 7-, 10-, 11-, and 12-positions should be hydrogen without introducing aryl groups.

Based on the above, compounds represented by Formula (2) or (3) (hereinafter, also referred to as Compound (2) or Compound (3)) are compared with compounds represented by Formula (5) or (6) (hereinafter, also referred to as Compound (5) or Compound (6)). Table 2 shows the calculated dihedral angles of the bond between the chrysene skeleton and the aryl group at the 2-position and the bond between the chrysene skeleton and the aryl group at the 3-position in Compound (2); and the calculated dihedral angles of the bond between the chrysene skeleton and the aryl group at the 3- or 9-position and the bond between the chrysene skeleton and the aryl group at the 6- or 12-position in Compound (3).

include unstable binding sites compared to the compounds of the present invention. That is, the compounds of the present invention have high stability relative to the comparative compounds.

In an organic light-emitting device, when holes are injected from a hole-transporting layer to a light-emitting layer or from a hole-injecting layer to a hole-transporting layer, a smaller difference in the HOMO level between the hole-injecting layer or the hole-transporting layer and the light-emitting layer decreases the barrier for hole injection.

TABLE 2

| Name | Structural formula | Dihedral angle (°) | | Bond length (Å) |
|---|---|---|---|---|
| Compound (2) | | a | 52 | 1.498 |
| | | b1 or b2 | 58 | 1.495 |
| Compound (3) | | c1 or c2 | 37 | 1.484 |
| | | d1 or d2 | 57 | 1.490 |
| Compound (5) | | e | 38 | 1.485 |
| Compound (6) | | f1 or f2 | 38 | 1.485 |

The results demonstrate that the comparative compounds used for the comparison each have a dihedral angle of 50° or more and a bond length of 1.49 Å or more and thus This reduces the drive voltage of the light-emitting device and leads to a reduction in power consumption or an increase in device lifetime. Accordingly, the barrier for hole injection can be reduced by using a compound having a shallow HOMO level.

When electrons are injected from an electron-transporting layer to a light-emitting layer or from an electron-injecting layer to an electron-transporting layer, a smaller difference in the LUMO level between the electron-injecting layer or the electron-transporting layer and the light-emitting layer decreases the barrier for electron injection, resulting in a further reduction in the drive voltage of the organic light-emitting device.

The HOMO-LUMO gap is the S1 energy level of a compound. A decrease in S1 energy deepens the LUMO level. Accordingly, the barrier for electron injection can be reduced by using a compound having a low S1 energy level.

In particular, in phosphorescent materials, many phosphorescent materials, such as Ir(ppy)3 and Ir(piq)3, have shallow HOMO levels.

Many organic compounds composed of hydrocarbons have deeper HOMO levels than those phosphorescent materials, and holes are trapped therein, resulting in provision of a light-emitting device having low hole-transportability. This reduces the carrier balance in the light-emitting device, leading to a short device lifetime of the light-emitting device.

Accordingly, in the use of a phosphorescent material, it is necessary to inhibit charge trapping by holes by using a material having a shallow HOMO level in the transporting layer and as a host material to also reduce the potential difference in HOMO level from that of the light-emitting material.

The stability determined based on the dihedral angle and the bond length does not highly differ between the compound having an aryl substituent at the 2- or 8-position and the compound having an aryl substituent at the 3- or 9-position of the present invention.

Table 3 shows the HOMO levels and the calculated S1 energy levels of Compound (4) having aryl substituents at the 2- and 8-positions and Compound (6) having aryl substituents at the 3- and 9-positions.

or more than that of Compound (4) having aryl substituents at the 2- and 8-positions. The HOMO level is also shallower by about 0.4 eV.

This demonstrates that the introduction of an aryl group at the 3- or 9-position provides a compound having a low S1 energy level and a shallow HOMO level.

In the light of these points, in order that a material having a chrysene skeleton can have high stability, a shallow HOMO level, and a low S1 energy level, it is necessary that aryl substituents are introduced at the 3- and 9-positions only and that other all substitution positions are hydrogen atoms.

Accordingly, the chrysene compound having aryl substituents at the 3- and 9-positions only according to the present invention can provide an organic light-emitting device showing a longer lifetime compared to chrysene skeleton compounds having aryl substituents at other positions by being used in a transporting layer or as a host material of the light-emitting layer of the organic light-emitting device.

The use of the compound as a host material of a phosphorescent material has a problem involved in the T1 energy. The T1 energy level of the chrysene skeleton itself is 500 nm, which allows to be used as a host material of a light-emitting layer emitting green to red light.

In a case of using the chrysene skeleton compound as a host material of the light-emitting layer of a red phosphorescent light-emitting device, introduction of a substituent having a T1 energy level of less than 620 nm, in particular, less than 550 nm, is necessary.

Specific examples of the substituent include benzene, naphthalene, fluorene, triphenylene, dibenzothiophene, dibenzofuran, phenanthrene, and fluoranthene.

In the embodiment, "an energy level less than 620 nm" means that the wavelength defined by an energy level is smaller than 620 nm. The value of an eV defining an energy level increases with a decrease in the wavelength. This applies to other wavelengths.

The use of the compound as a host material of a fluorescent material does not have any problem involved in the T1 energy, and the compound can be used in a blue to red region.

TABLE 3

| Name | Structural formula | S1 | HOMO |
|---|---|---|---|
| Compound (4) | | 3.56 eV | −5.77 eV |
| Compound (6) | | 3.40 eV | −5.36 eV |

Table 3 shows the results that Compound (6) having aryl substituents at the 3- and 9-positions according to the present invention has an S1 energy level lower by 0.15 eV In a case of using the compound as a host material of the fluorescent material, examples of the substituent include pyrene, anthracene, and perylene in addition to those of the compounds used as a host material of the phosphorescent material.
Specific non-limiting examples of the organic compound according to the present invention are shown below.
[Chem. 14]
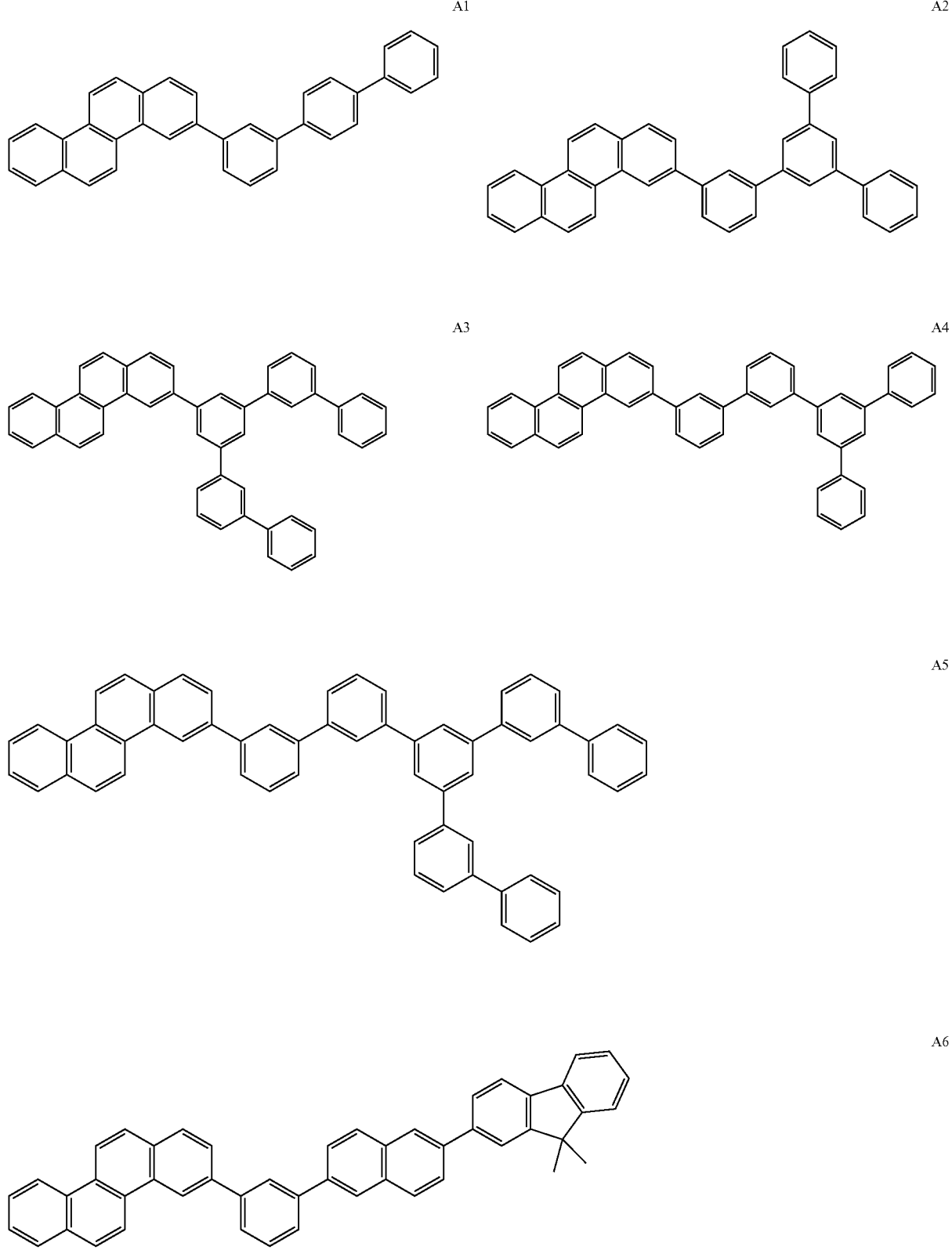

-continued
A7
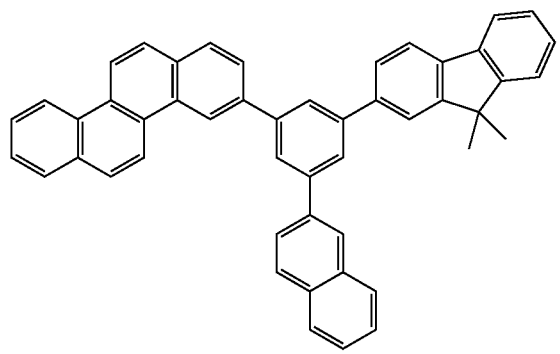
A8
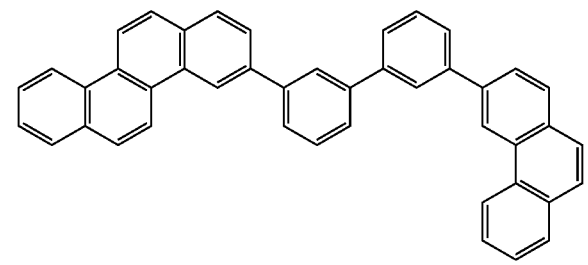
A9
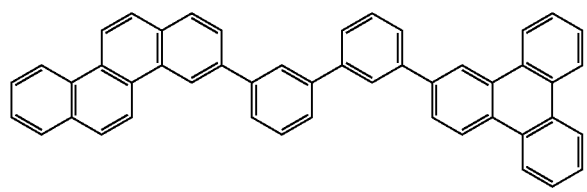
A10
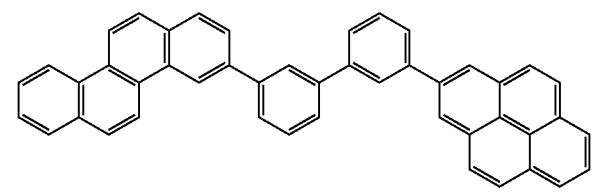
A11
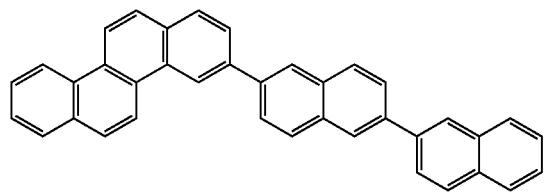
A12
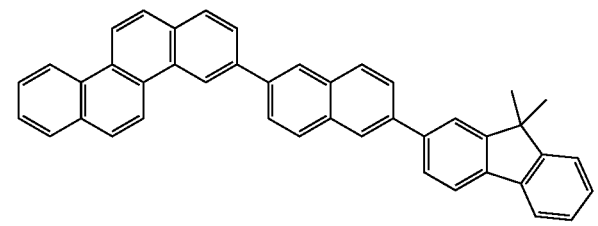
A13
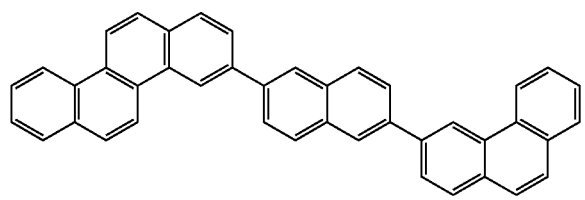
A14
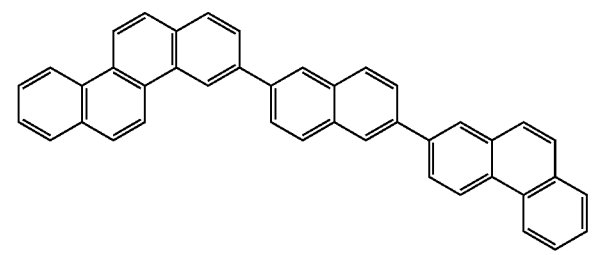
A15
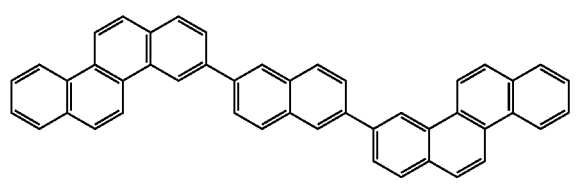
A16
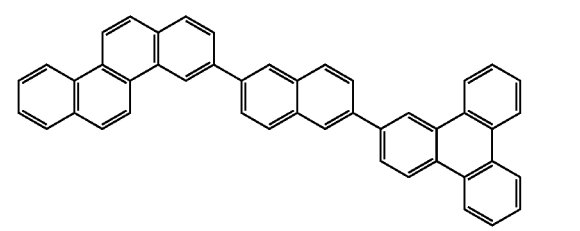

-continued
A17
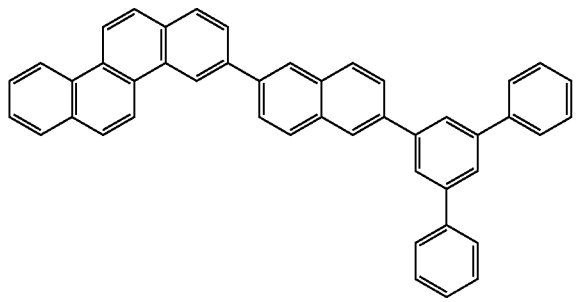
A18
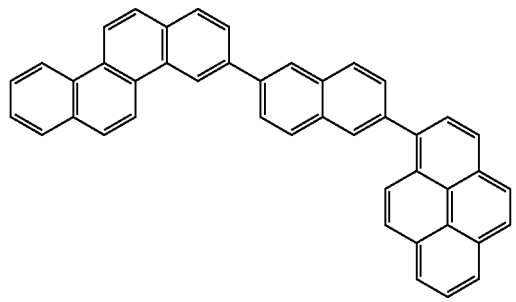
[Chem. 15]
A19
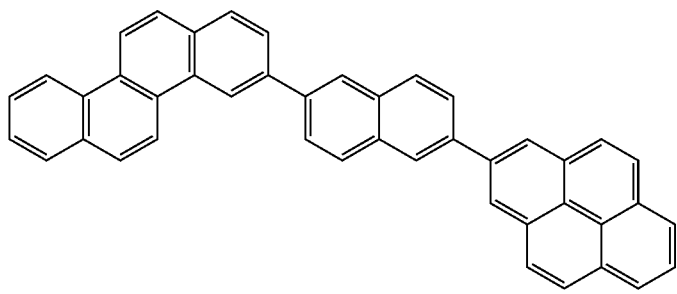
A20
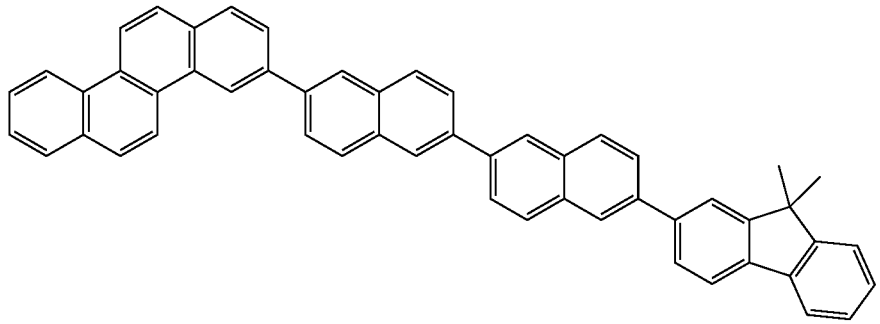
A21
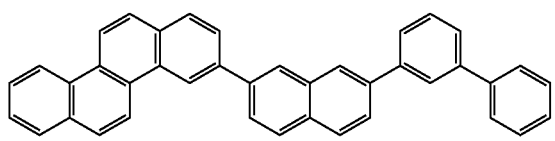
A22
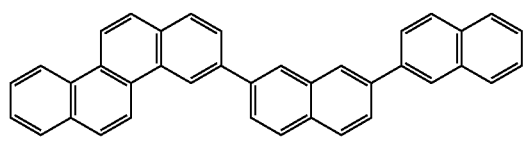
A23
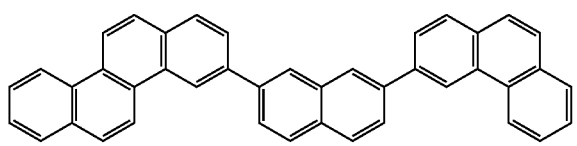
A24
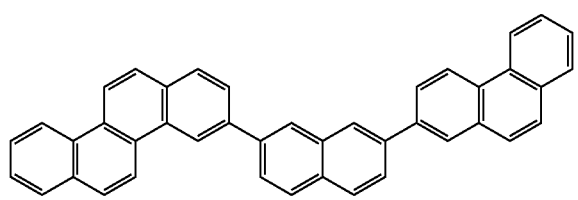
A25
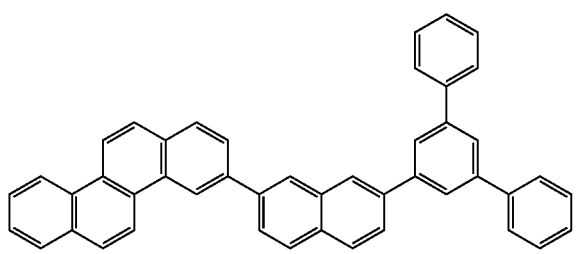
A26
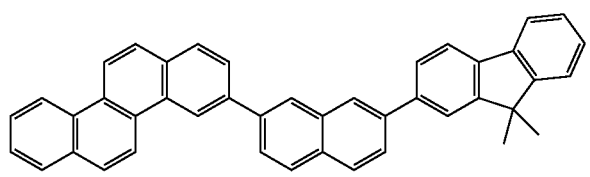

-continued

A36
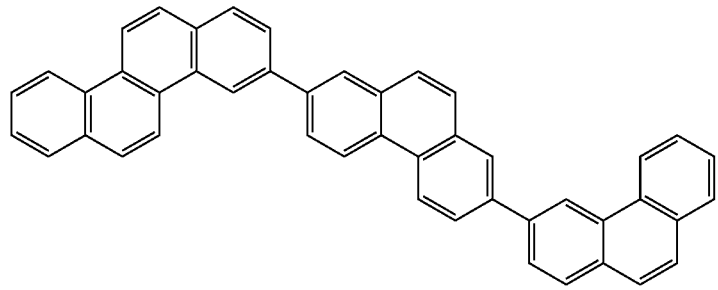
[Chem. 16]
A37
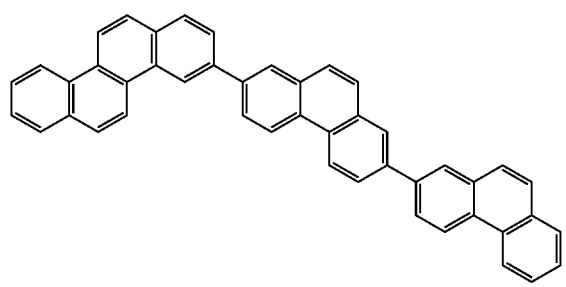
A38
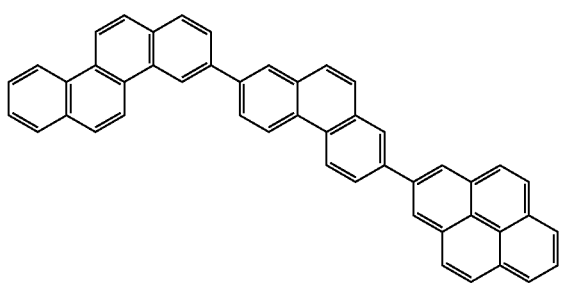
A39
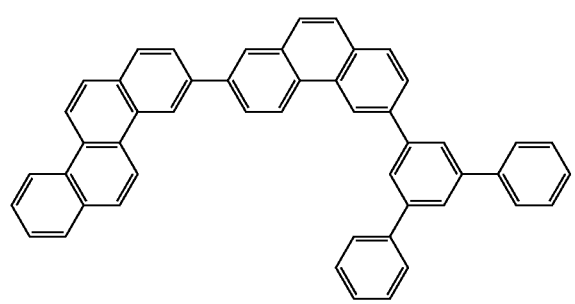
A40
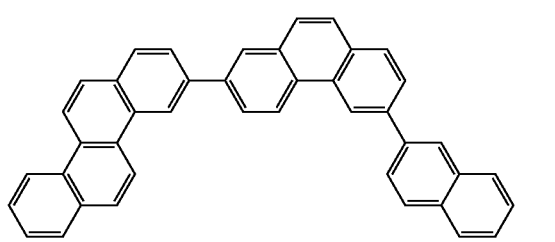
A41
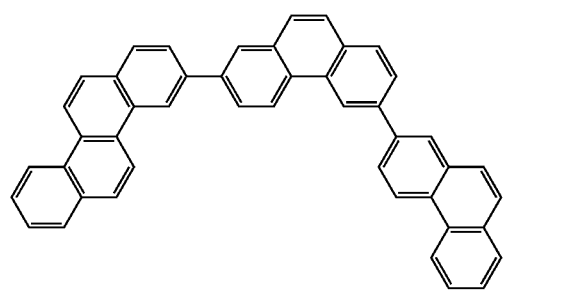
A42
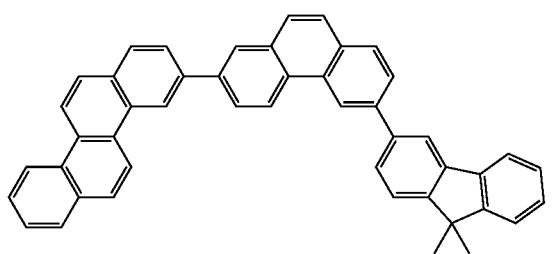
A43
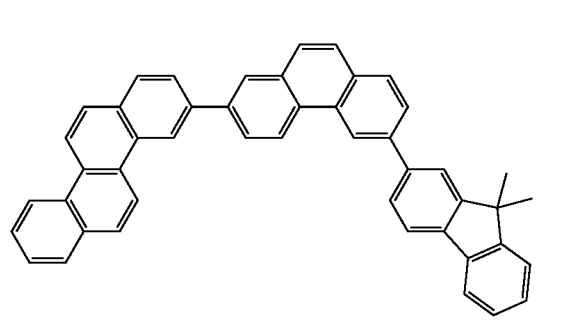
A44
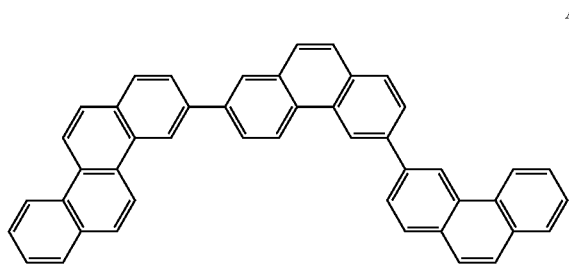

-continued
A45
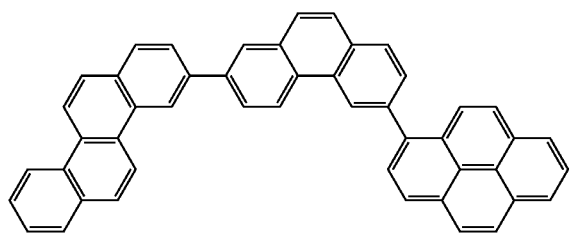
A46
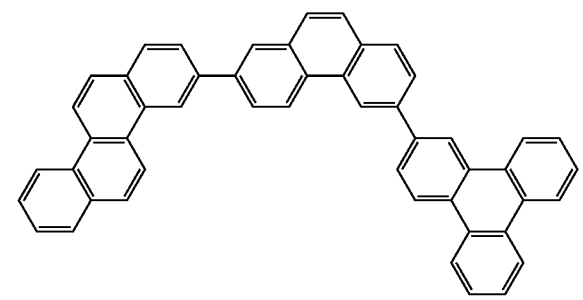
A47
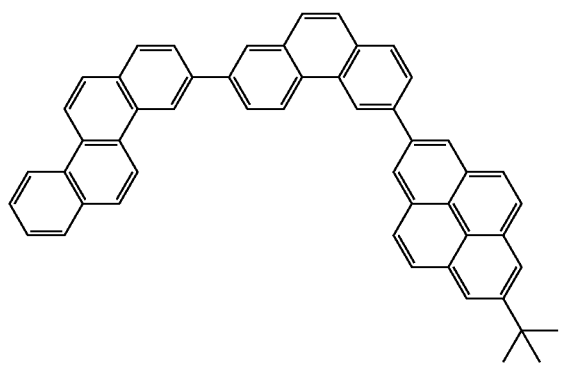
A48
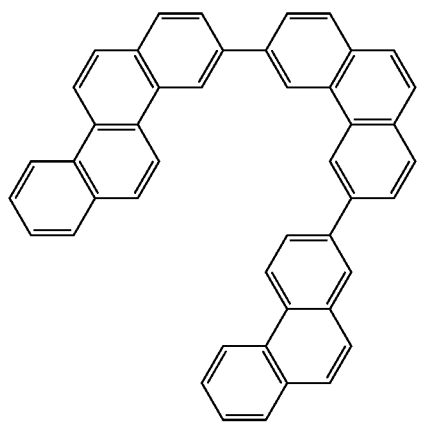
A49
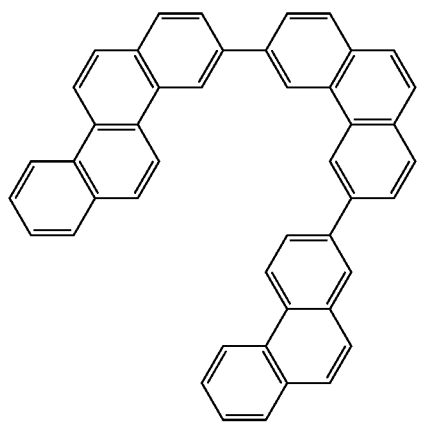
A50
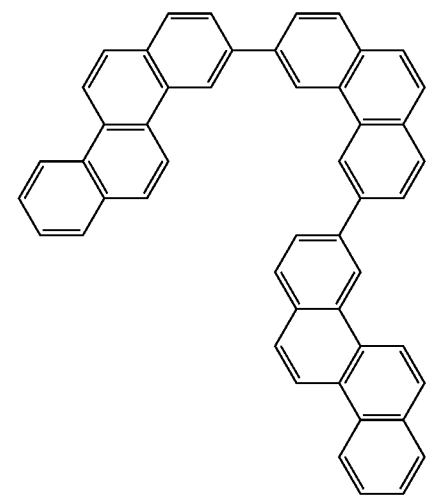
A51
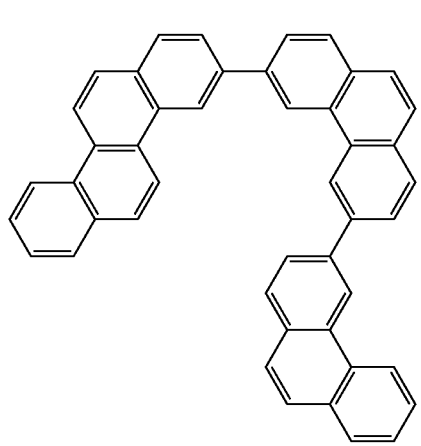
A52
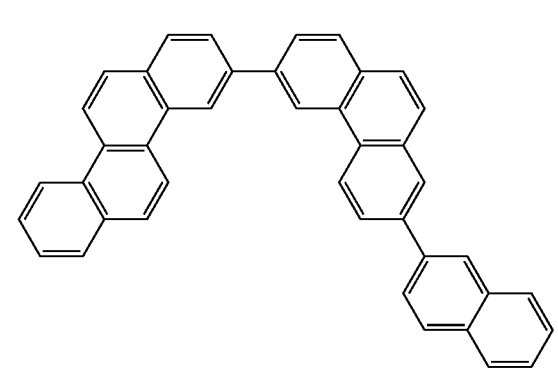

-continued
A53
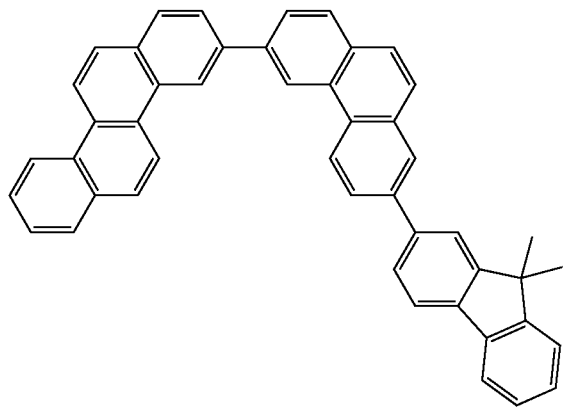
A54
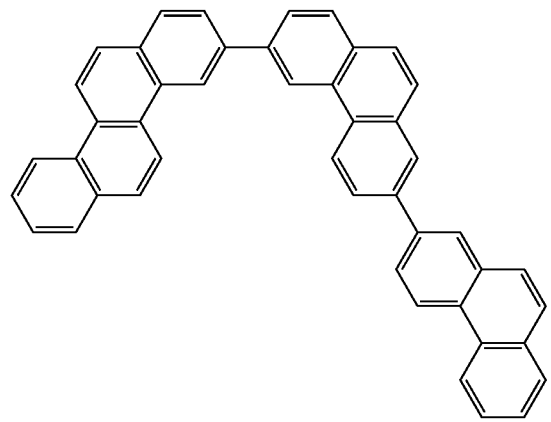
[Chem. 17]
A55
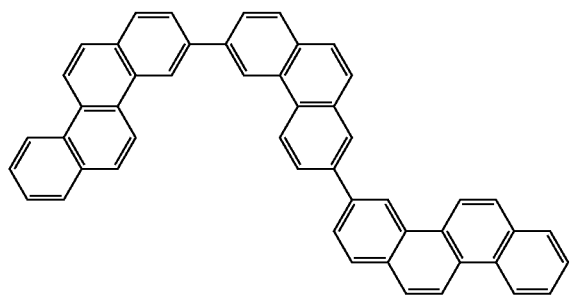
A56
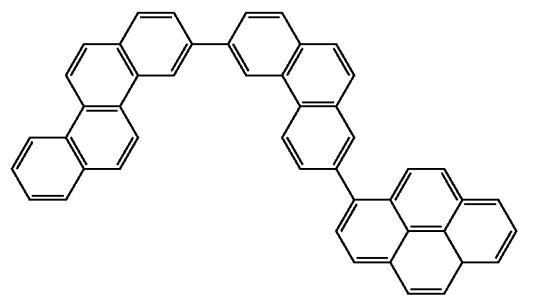
A57
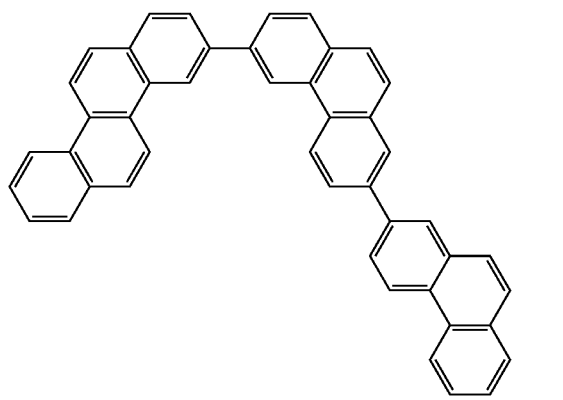
A58
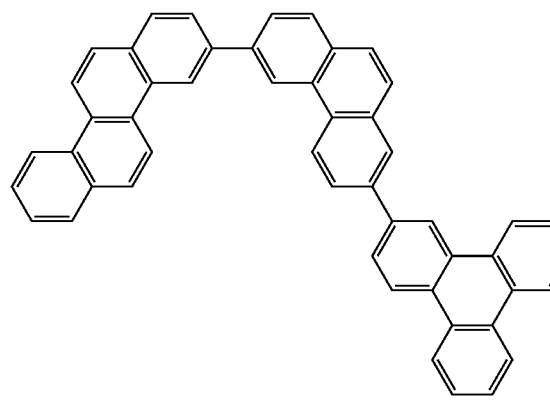
A59
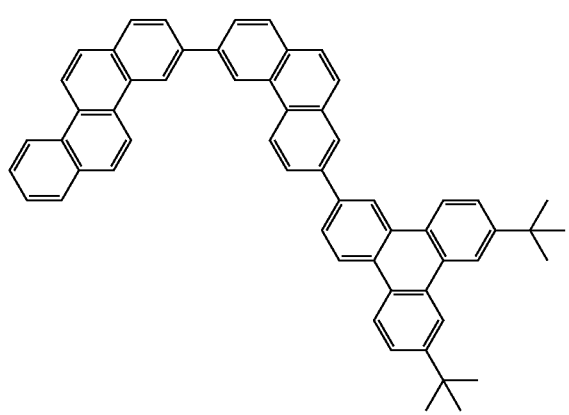
A60
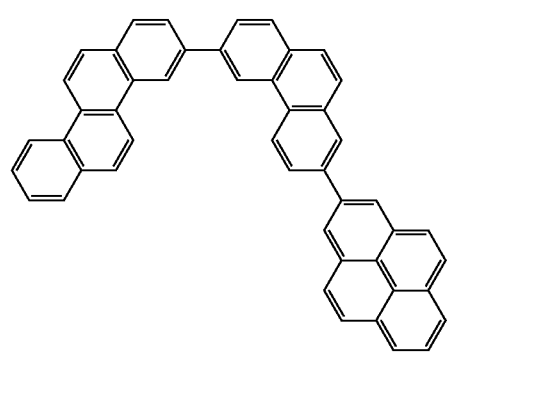

-continued
A61
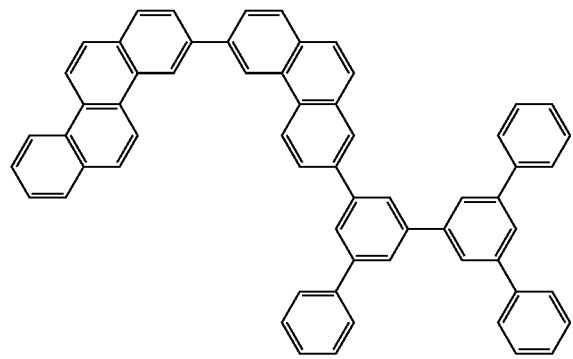
A62
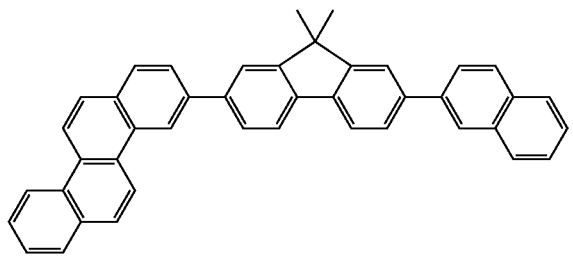
A63
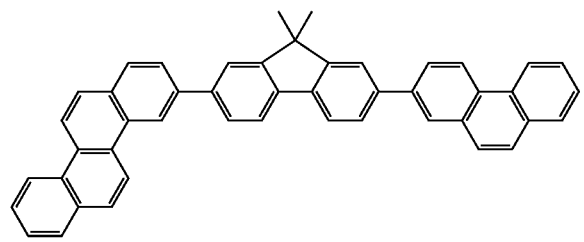
A64
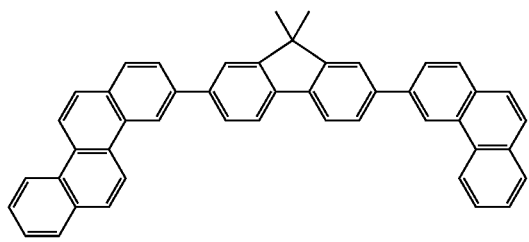
A65
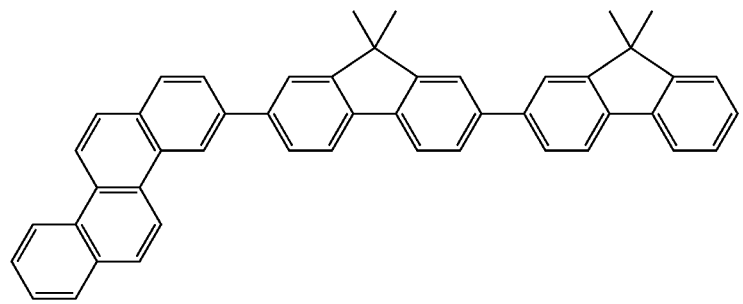
A66
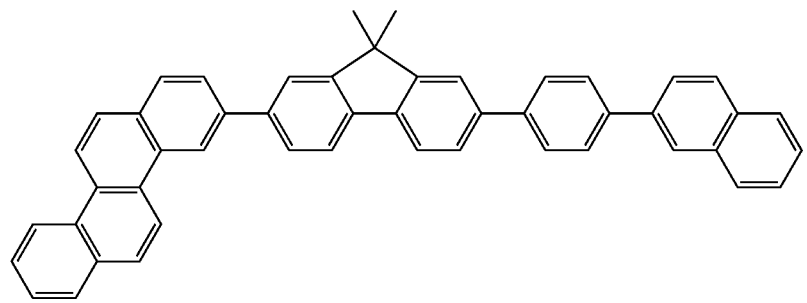
A67
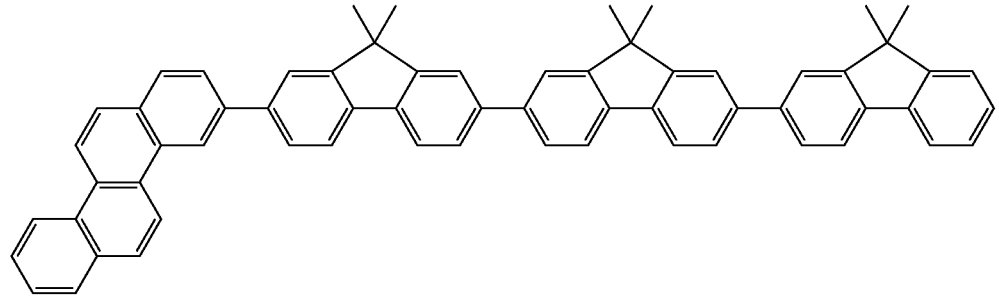

A68
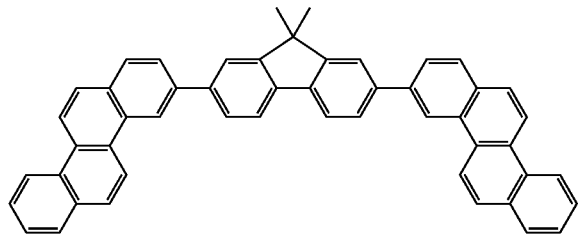
A69
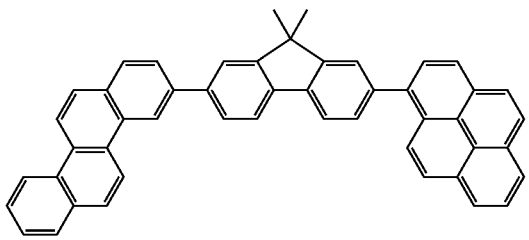
A70
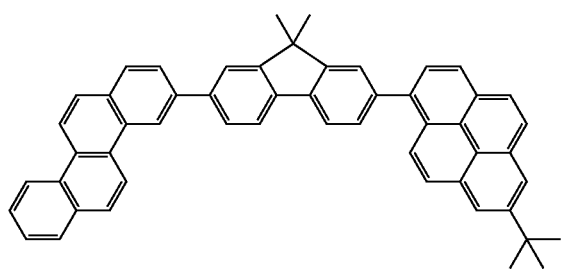
A71
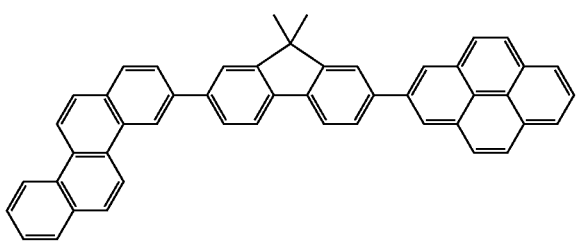
A72
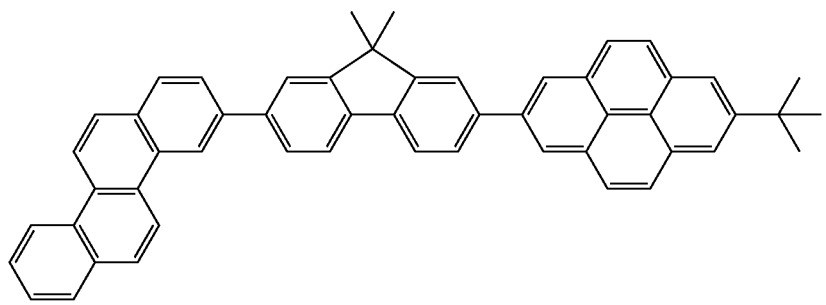
[Chem. 18]
A73
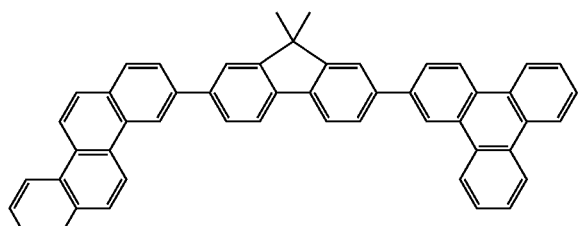
A74
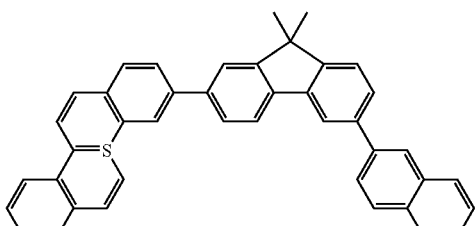
A75
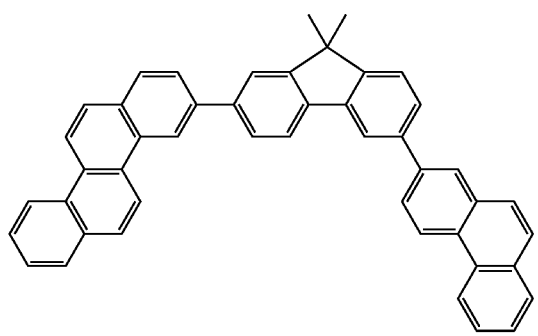
A76
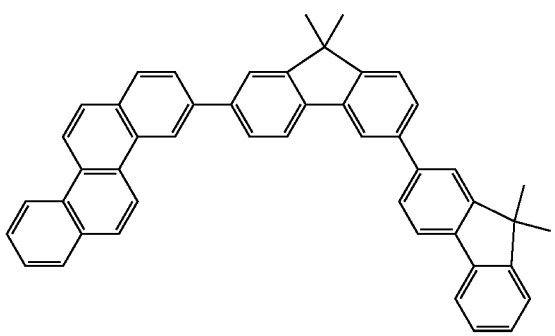

-continued
A77
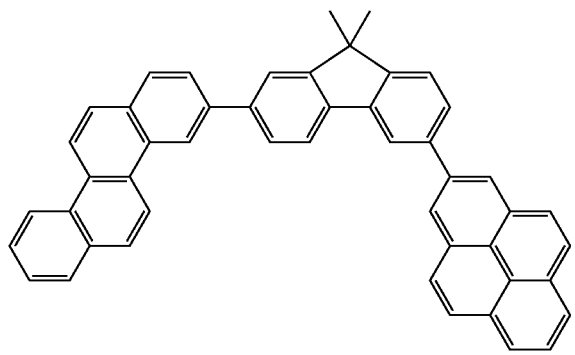
A78
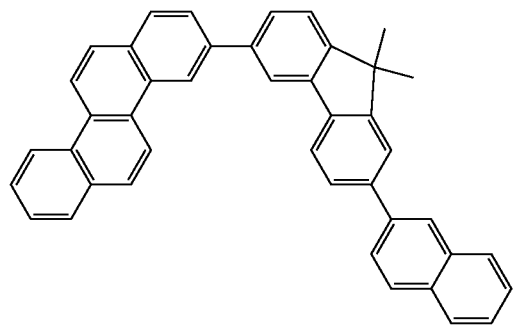
A79
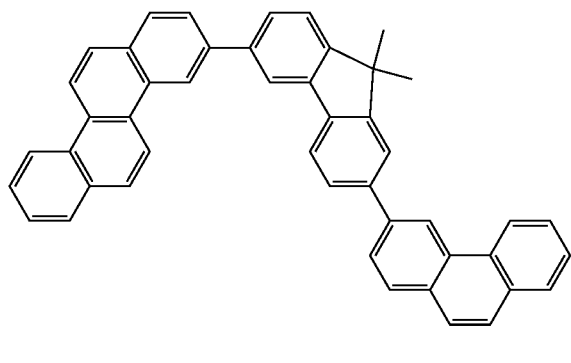
A80
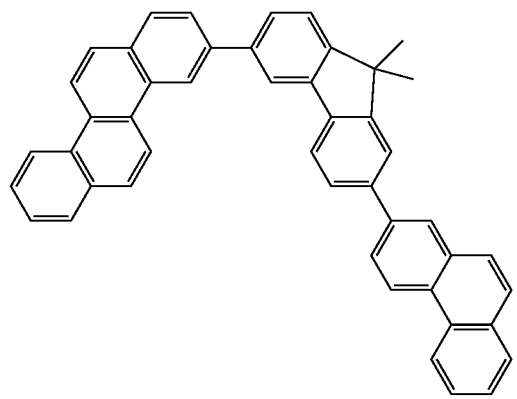
A81
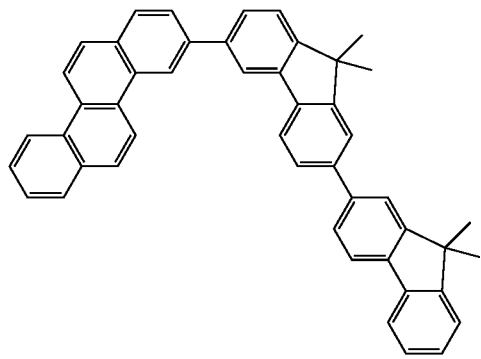
A82
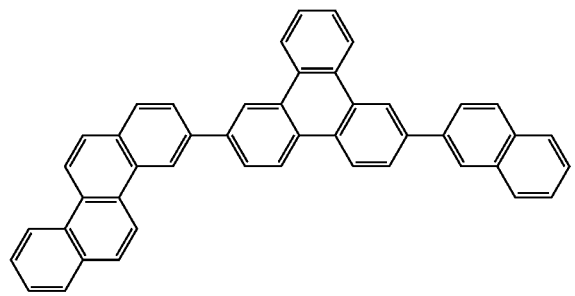
A83
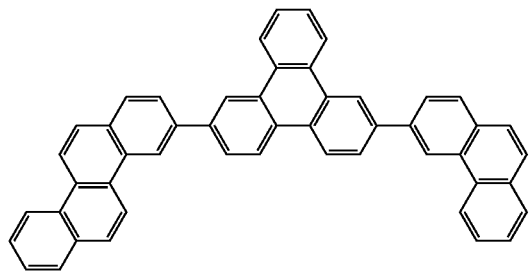
A84
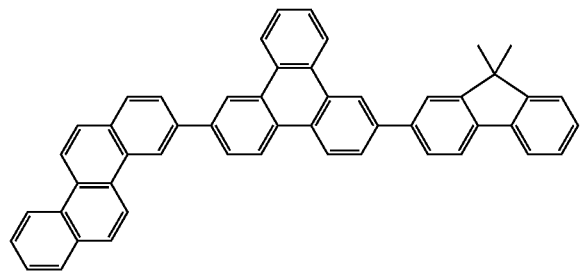

A85
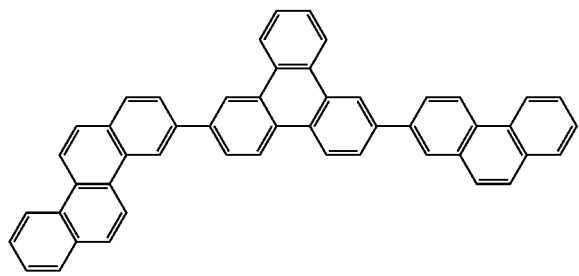
A86
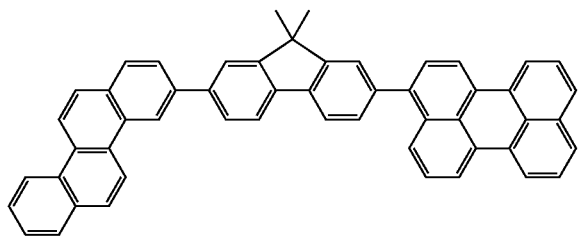
A87
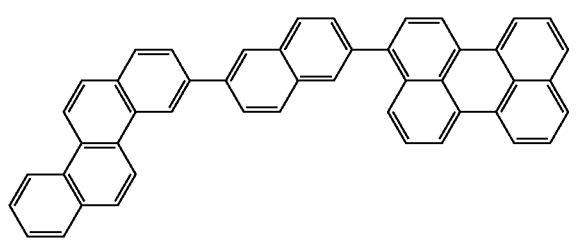
A88
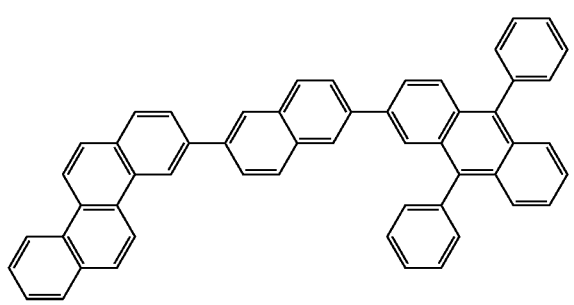
A89
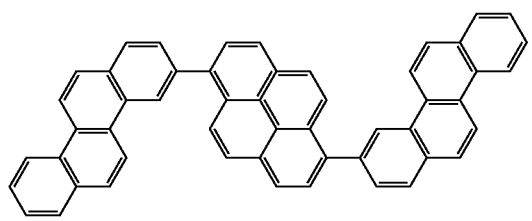
A90
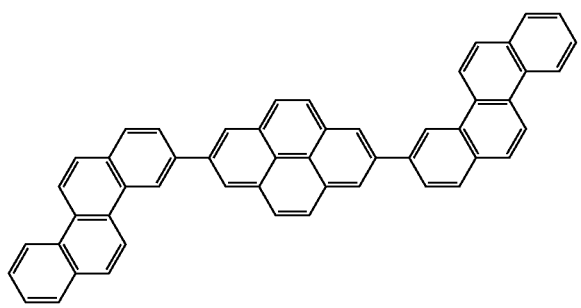
[Chem. 19]
B1
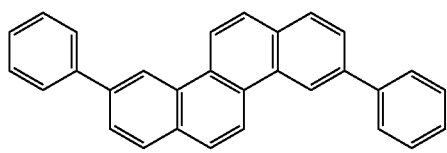
B2
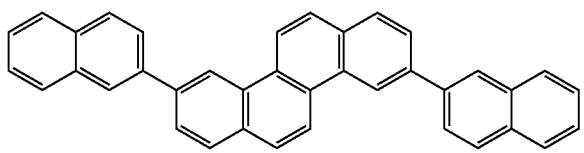
B3
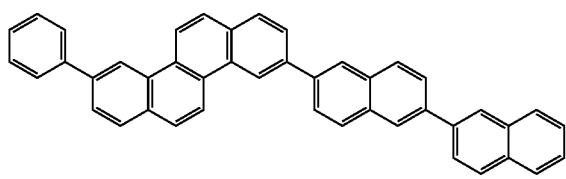
B4
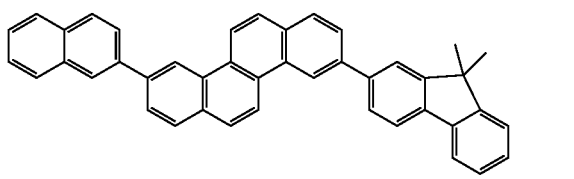
B5
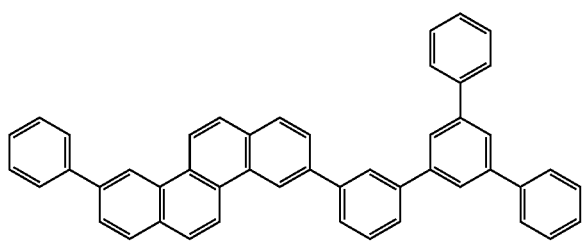
B6
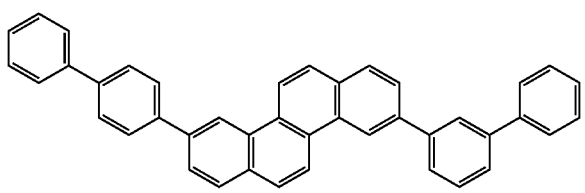

-continued
B7
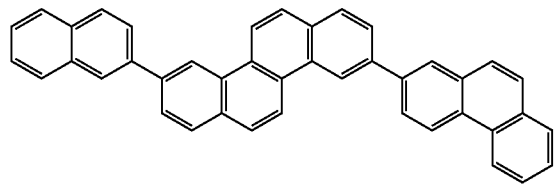
B8
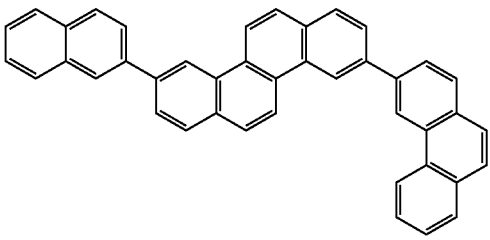
B9
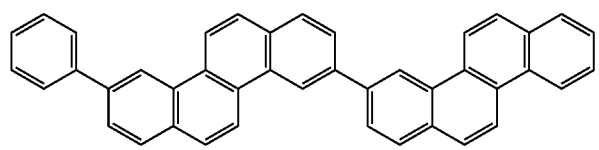
B10
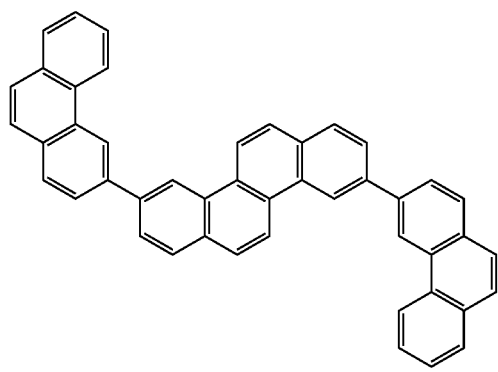
B11
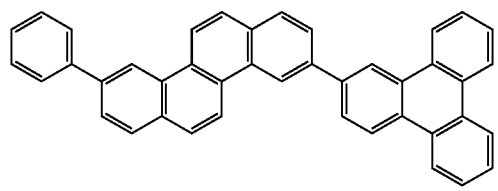
B12
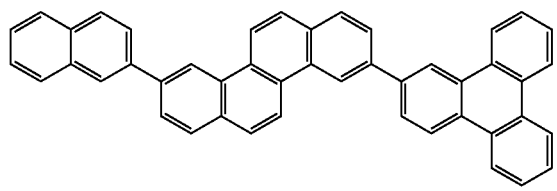
B13
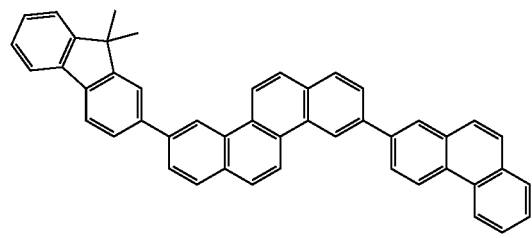
B14
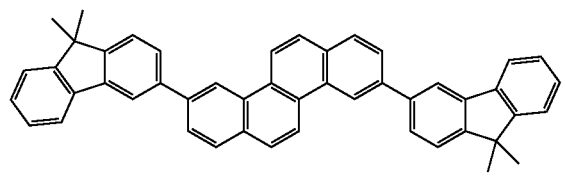
B15
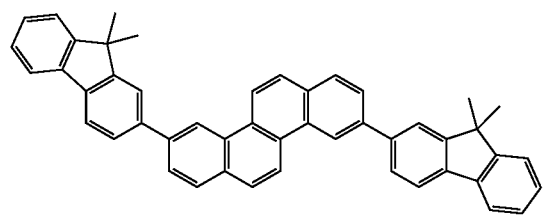
B16
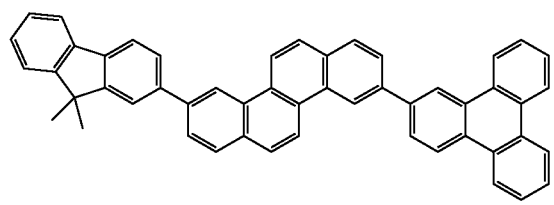
B17
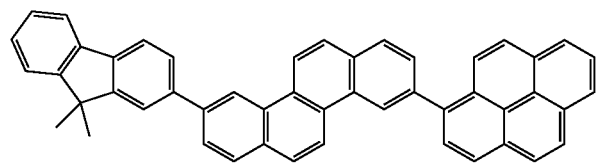
B18
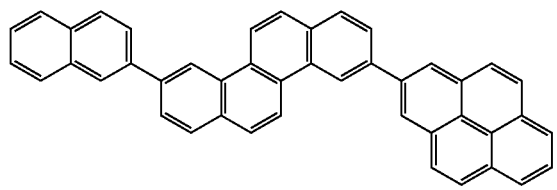

[Chem. 20]
B19
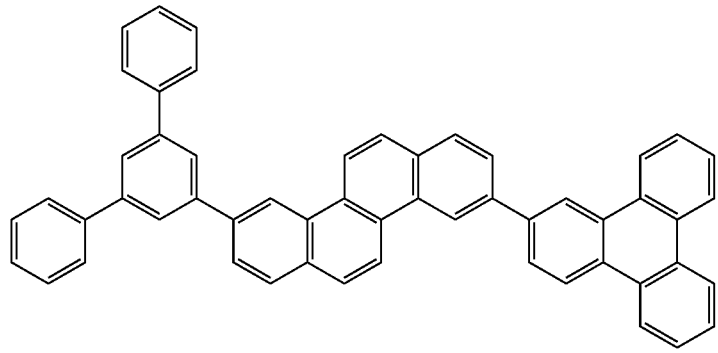
B20
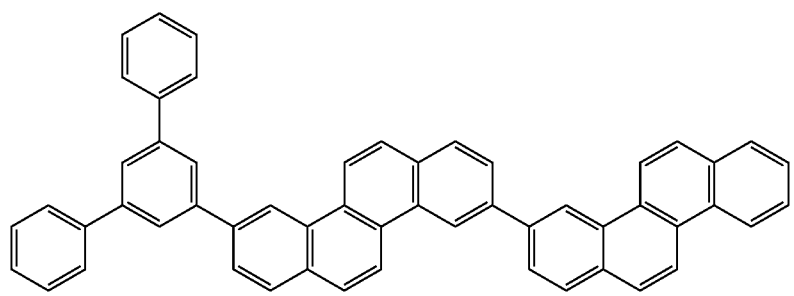
B21
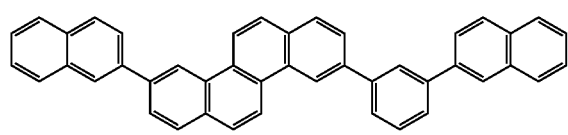
B22
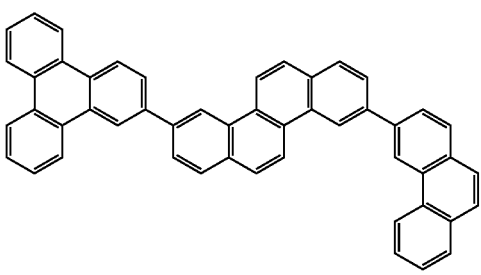
B23
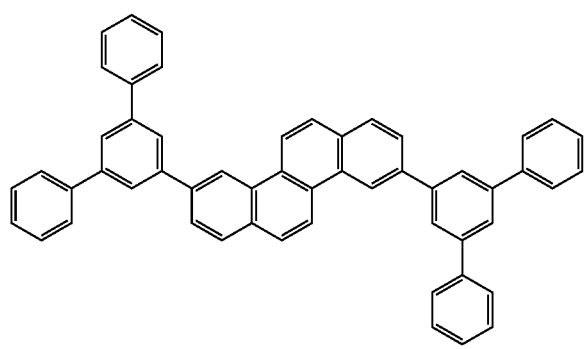
B24
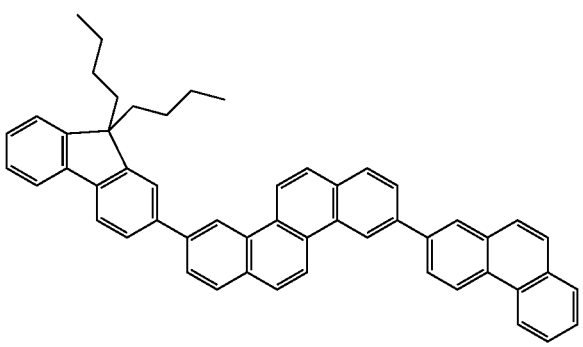
B25
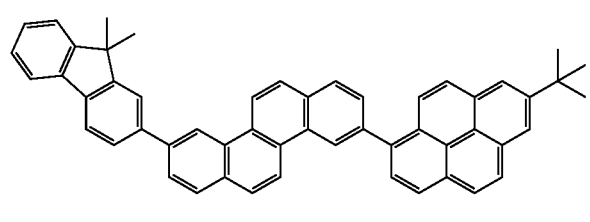
B26
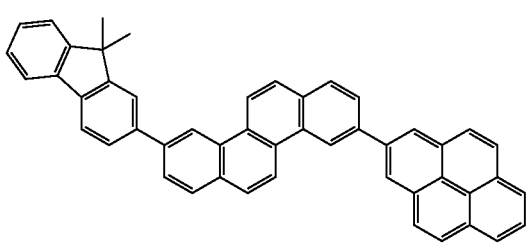

-continued
B27
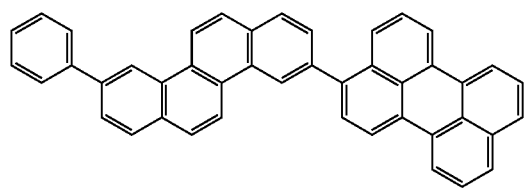
B28
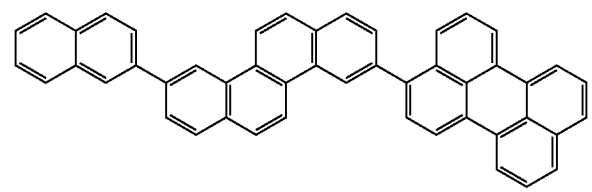
B29
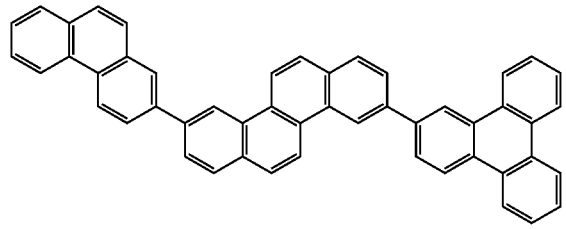
B30
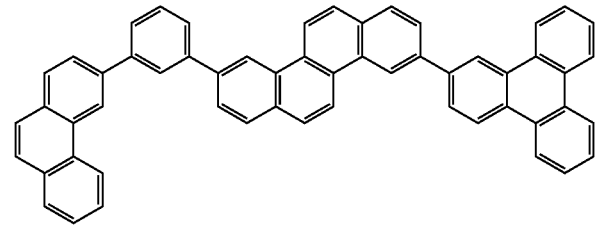
B31
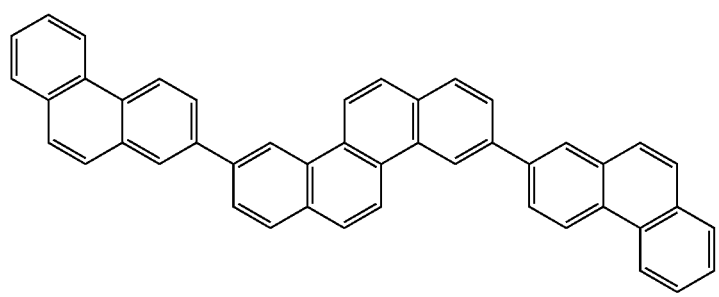
B32
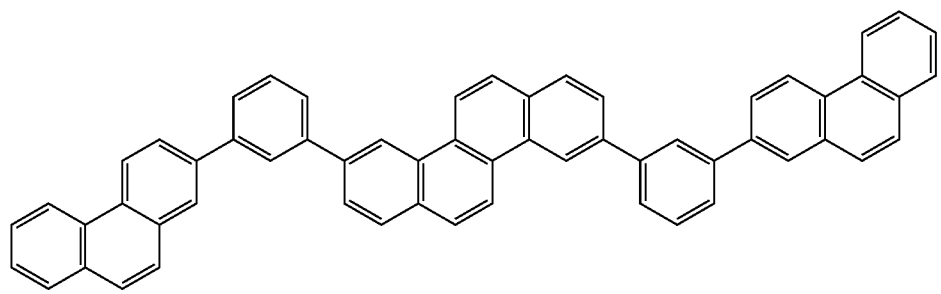
B33
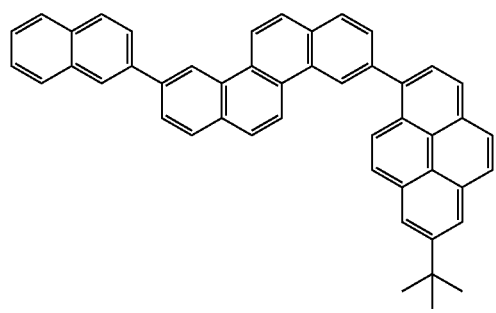
B34
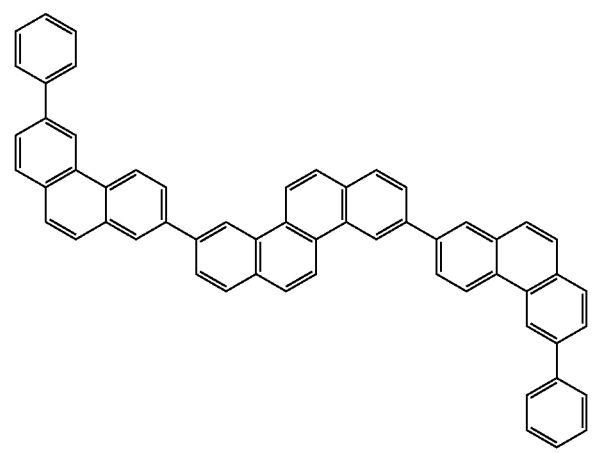

-continued
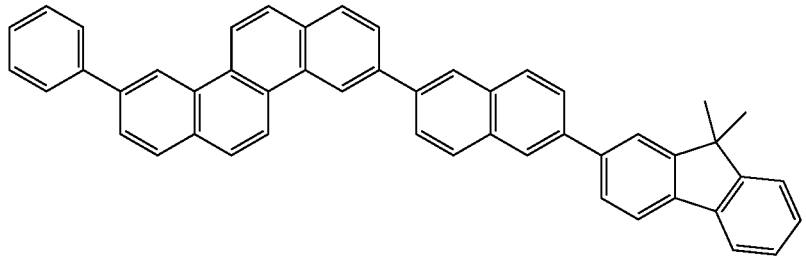
B35
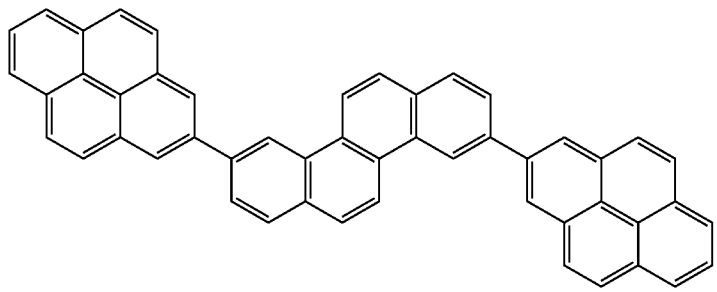
B36
[Chem. 21]
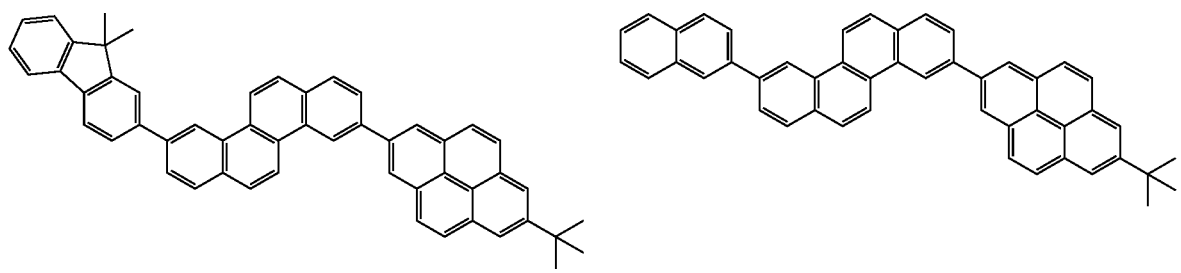
B37    B38
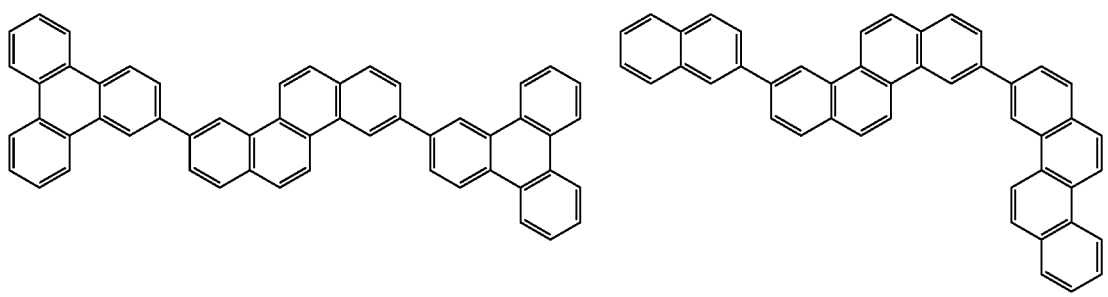
B39    B40
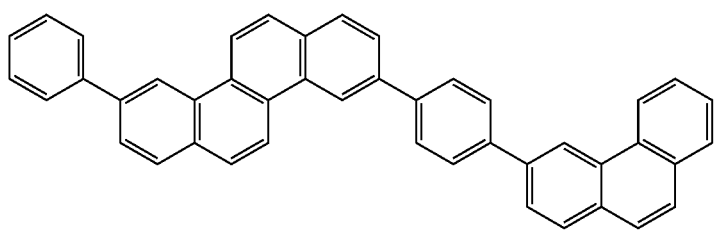
B41

-continued
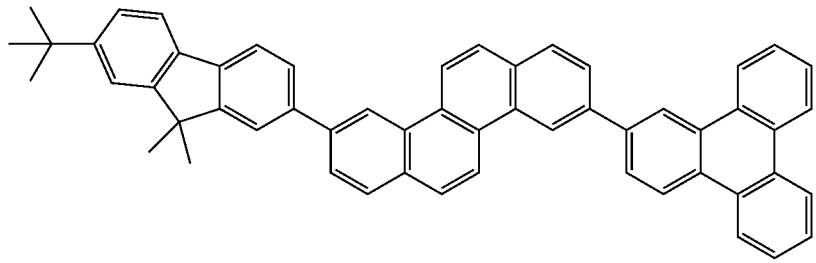
B42
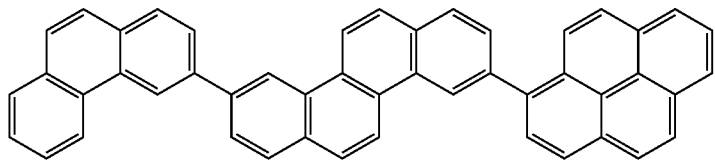
B43
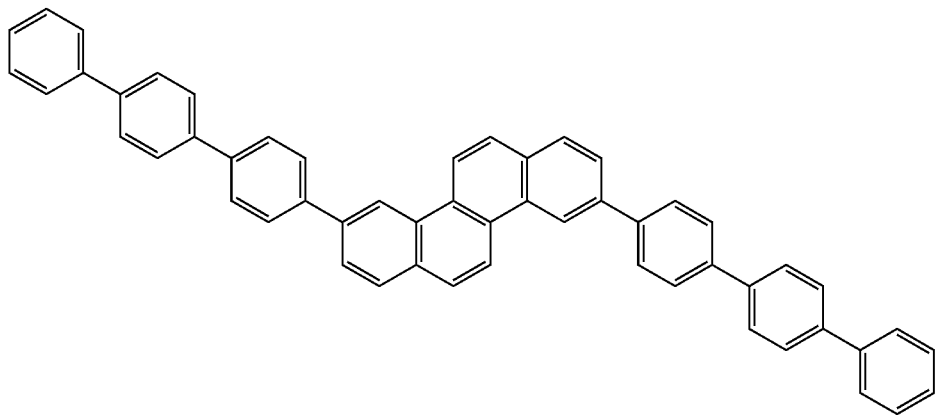
B44
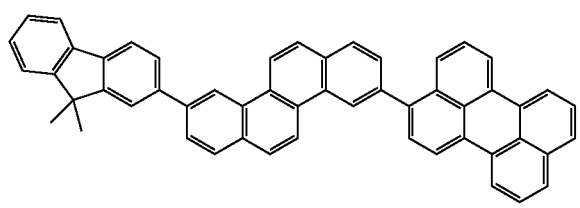
B45
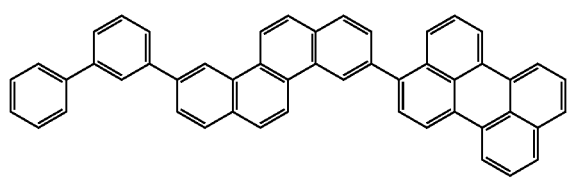
B46
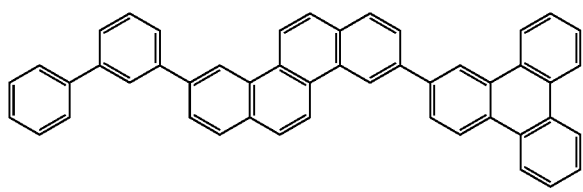
B47
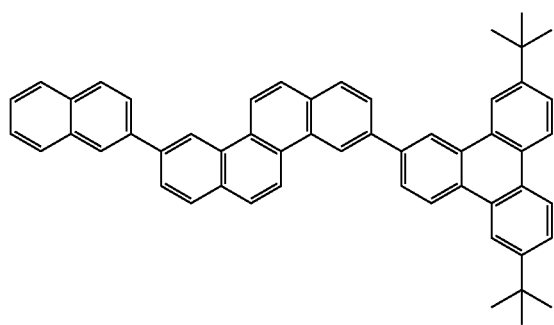
B48

-continued
B49
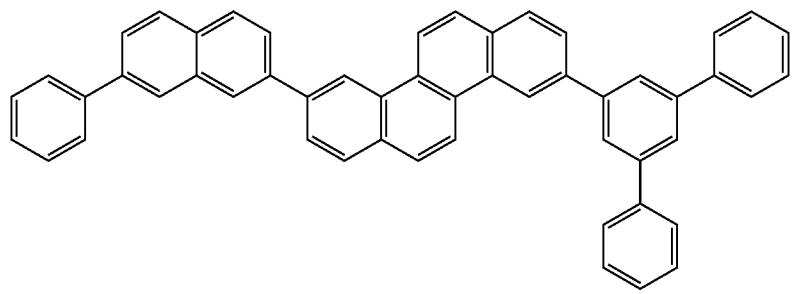
B50
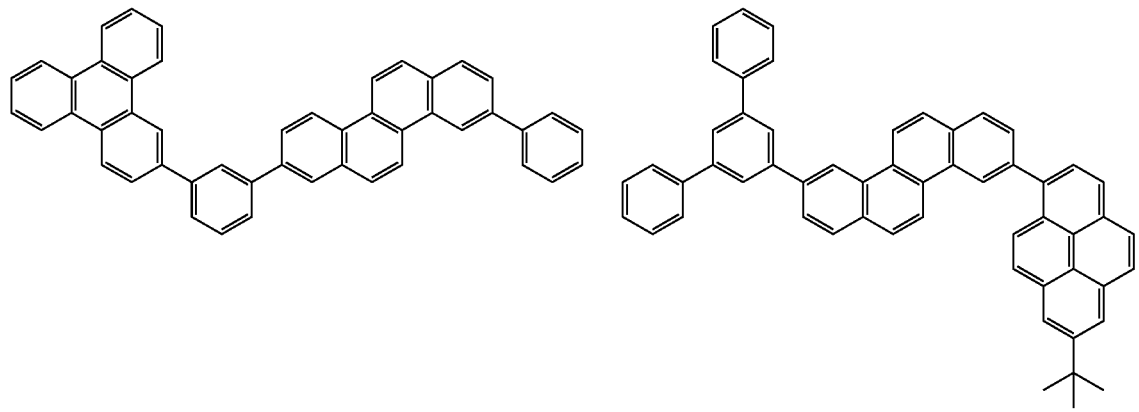
B51
B52
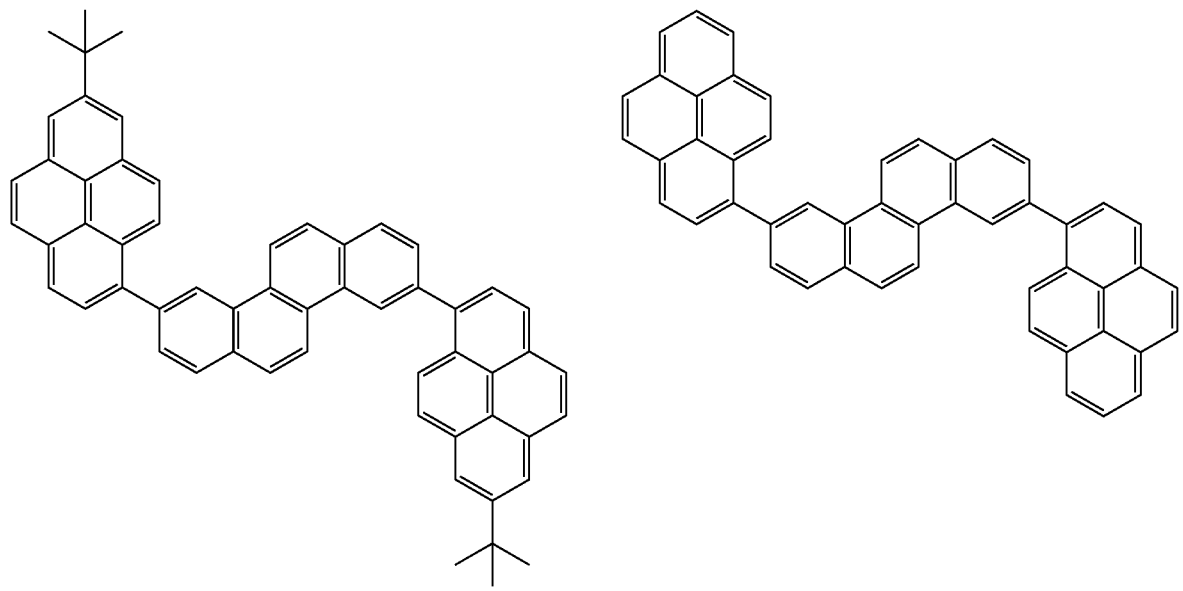
B53
B54
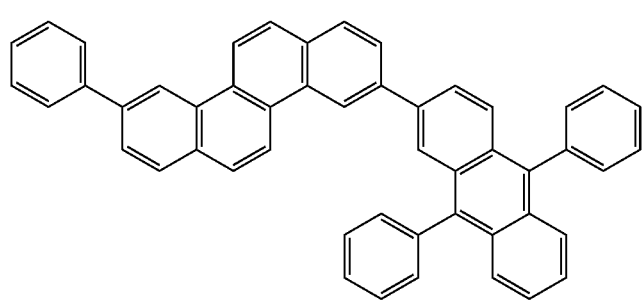

[Chem. 22]
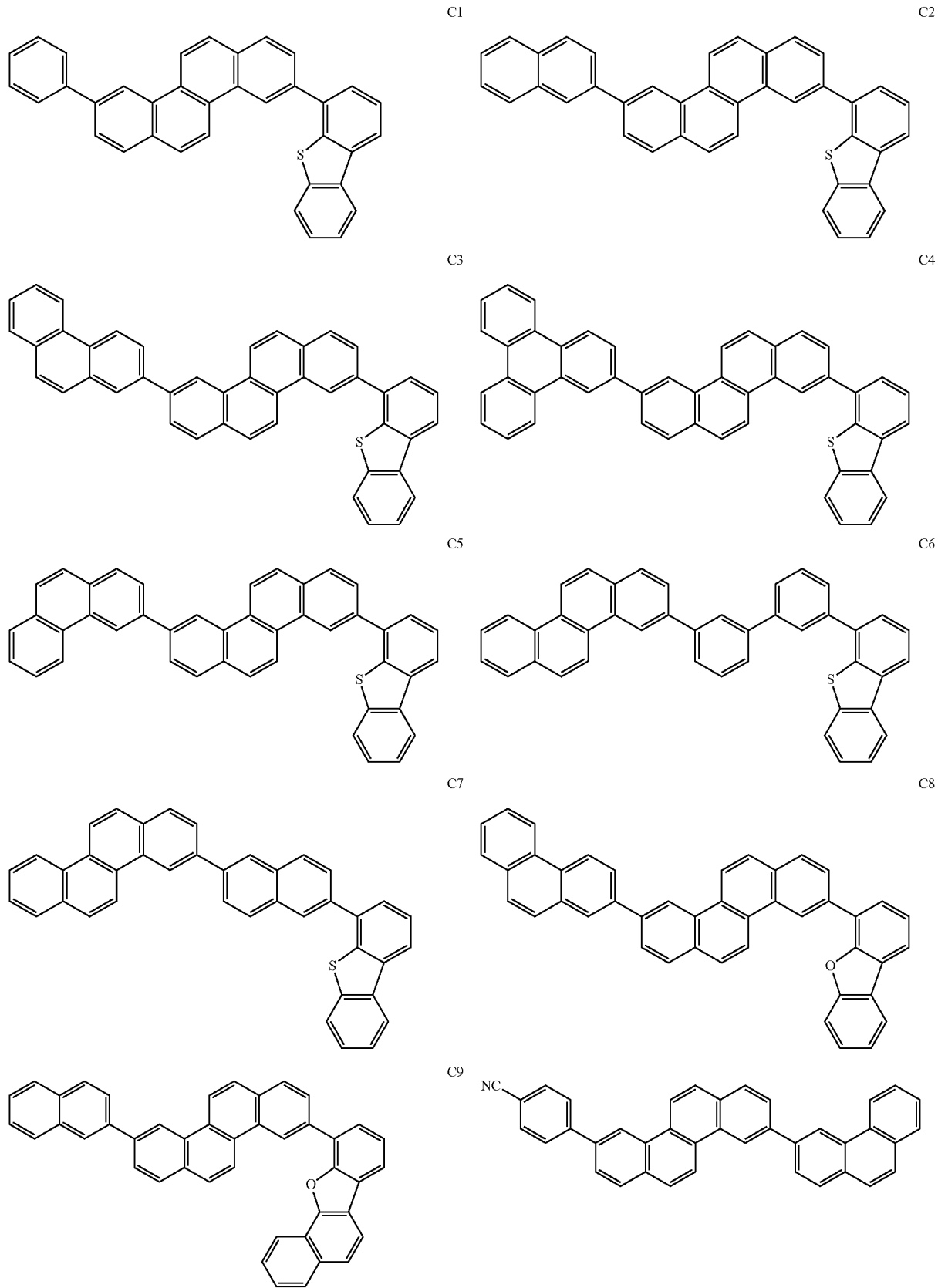

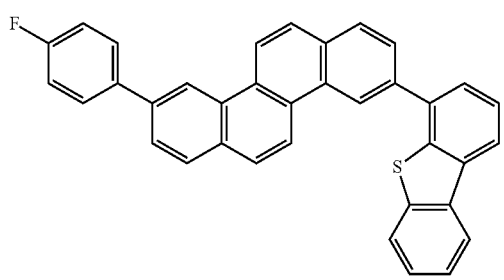
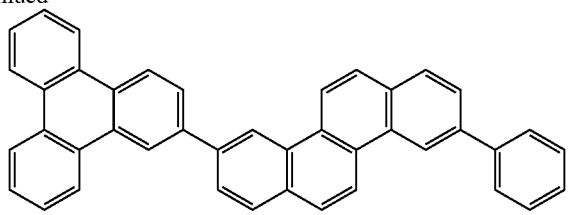

In the compounds exemplified above, the compounds belonging to Group A each have an aryl substituent only at the 3-position of chrysene, and each molecule is constituted of only hydrocarbons. Since the substituent is introduced only at the 3-position of chrysene, the synthesis is easy.

In general, a compound constituted of only hydrocarbons has a high binding energy level. The organic compounds are therefore stable.

Among the organic compounds according to the embodiment, the organic compounds constituted of only hydrocarbons, i.e., the compounds belonging to Group A have high molecular stability.

Each organic compound belonging to Group A can also be used as a high concentration material having a purity of up to 100% in a light-emitting layer, a transporting layer, or an injecting layer.

In a case of using the organic compound in a light-emitting layer, the compound can be used as a host material not as a light-emitting material. In the case of using the organic compound as the host material, the emission efficiency is high when the concentration of the light-emitting material is low.

Herein, "a high concentration" means a case in which the purity of a light-emitting material is 50% or more relative to the organic compound belonging to Group A, whereas "a low concentration" means a case in which the purity is 10% or less.

The compounds belonging to Group A according to the embodiment are represented by the following Formula (7):

[Chem. 23]

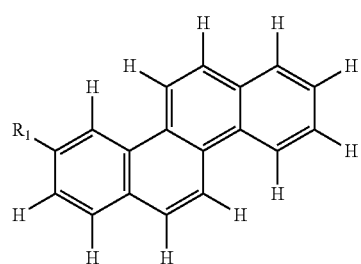

(7)

In Formula (7), $R_1$ represents a substituted or unsubstituted aryl group.

Examples of the aryl group include phenyl, naphthyl, biphenyl, phenanthryl, fluorenyl, triphenylenyl, and chrysenyl groups.

The aryl group may have an alkyl, phenyl, terphenyl, naphtyl, phenanthryl, fluorenyl, triphenylenyl, chrysenyl, pyrenyl, tetracenyl, perylenyl, anthracenyl, dibenzothiophenyl, or dibenzofuranyl group.

The substituent of the aryl group may further have an alkyl group.

In the compounds exemplified above, the compounds belonging to Group B each have aryl substituents at the 3- and 9-positions of chrysene, and each molecule is constituted of only hydrocarbons.

In these compounds, the band gap relative to chrysene skeleton can be readily controlled. In general, a compound constituted of only hydrocarbons has a high binding energy level. The organic compounds are therefore stable.

Accordingly, among the organic compounds according to the embodiment, the organic compounds constituted of only hydrocarbons, i.e., the compounds belonging to Group B have high molecular stability. Each organic compound belonging to Group B can also be used as a high concentration material having a purity of up to 100% in a light-emitting layer, a transporting layer, or an injecting layer.

In a case of using the organic compound in a light-emitting layer, the compound can be used as a host material not as a light-emitting material. In the case of using the organic compound as the host material, the emission efficiency is high when the concentration of the light-emitting material is low. Herein, "a high concentration" means a case in which the purity of a light-emitting material is 50% or more relative to the organic compound belonging to Group B, whereas "a low concentration" means a case in which the purity is 10% or less.

When the compound is used as a host material, the light-emitting layer may contain an assist material in addition to the guest material. The assist material is a compound having an energy level between the energy level of the host material and the energy level of the guest material.

In the compounds exemplified above, the compounds belonging to Group C each have a substituent containing a heteroatom in a cyclic group. Though the binding between a heteroatom and a carbon atom is generally weaker than that between carbon atoms, in this case, since the substituent has a heteroatom in a cyclic group, the binding between the heteroatom and the carbon atom is strong.

As a result, the compounds are stable molecules despite of the existence of heteroatoms. In this case, the intermolecular interaction varies due to the heteroatom.

Each organic compound belonging to Group C having a substituent containing a heteroatom is also useful as an electron-transporting, hole-transporting, or hole-trapping light-emitting material. Among the organic compounds, the fluorinated compounds, in which the intermolecular interaction is suppressed, are expected to be improved in the sublimability.

The organic compounds belonging to Group C can also be used as high concentration materials having a purity of up to 100%. Herein, "a high concentration" means a case using the organic compound belonging to Group C at a purity of 50% or more, whereas "a low concentration" means a case using the compound at a purity of 10% or less.

The organic light-emitting device of the embodiment will now be described.

The organic light-emitting device of the embodiment at least includes a pair of electrodes, an anode and a cathode, and an organic compound layer disposed between the electrodes. The organic compound layer of the organic light-emitting device of the embodiment may be a monolayer or a laminate of a plurality of layers as long as a light-emitting layer is included.

When the organic compound layer is a laminate composed of a plurality of layers, the organic compound layer may include, in addition to the light-emitting layer, for example, a hole-injecting layer, a hole-transporting layer, an electron-blocking layer, a hole/exciton-blocking layer, an electron-transporting layer, and an electron-injecting layer. The light-emitting layer may be a monolayer or a laminate of a plurality of layers.

In the organic light-emitting device of the embodiment, an organic compound according to the embodiment is contained in at least one layer of the organic compound layers.

Specifically, the organic compound according to the embodiment is may be contained in any of the light-emitting layer, the hole-injecting layer, the hole-transporting layer, the electron-blocking layer, the hole/exciton-blocking layer, the electron-transporting layer, and the electron-injecting layer. In particular, the organic compound according to the embodiment can be contained in the light-emitting layer.

When the organic compound according to the present invention is contained in the light-emitting layer of the organic light-emitting device of the embodiment, the light-emitting layer may be formed of only the organic compound according to the embodiment or may be formed of the organic compound according to the embodiment and another compound.

In the case of a light-emitting layer made of the organic compound according to the embodiment and another compound, the organic compound according to the embodiment may be used as a host material or a guest material of the light-emitting layer or may be used as an assist material that can be contained in the light-emitting layer.

Herein, the host material is a compound having a largest weight ratio among the compounds constituting a light-emitting layer, and the guest material is a compound having a smaller weight ratio than that of the host material among the compounds constituting a light-emitting layer and bearing main light emission. The assist material is a compound having a smaller weight ratio than that of the host material among the compounds constituting a light-emitting layer and assisting the light emission of the guest material. The assist material is also referred to as a second host material.

The present inventors have conducted various investigations and have found that an organic light-emitting device having an optical output with high efficiency and high luminance and showing significantly high durability can be obtained by using the organic compound according to the embodiment as a host material of the light-emitting layer or as the electron-transporting layer, in particular, as a host material of the light-emitting layer.

The light-emitting layer may be a monolayer or a multilayer and also can mix emission colors by containing light-emitting materials having two or more emission colors. The multilayer refers to a laminate of a plurality of light-emitting layers. In this case, the emission color of the organic light-emitting device ranges from blue, green and to red, but is not particularly limited.

More specifically, the emission color may be white or an intermediate color. In the case of emitting white light, the light-emitting layers emit light of red, blue, and green. The layer may be formed by deposition or application.

In the organic white-light-emitting device according to the embodiment, the organic compound layer may have a light-emitting portion, and the light-emitting portion may contain a plurality of light-emitting materials, of which any two light-emitting materials emit light of colors different from each other such that the device including these materials emits white light.

The organic compound according to the embodiment can be used as a constituent material of an organic compound layer other than the light-emitting layer constituting the organic light-emitting device of the embodiment. Specifically, The organic compound according to the embodiment may be used as a constituent material of, for example, an electron-transporting layer, an electron-injecting layer, a hole-transporting layer, a hole-injecting layer, or a hole-blocking layer.

Herein, in addition to the organic compound according to the embodiment, for example, a known low-molecular or high-molecular light-emitting material, hole-injecting or transporting compound, host material, light-emitting compound, or electron-injecting or transporting compound can be optionally used.

Examples of these compounds will be shown below.

The light-emitting material that is used as a guest material a fluorescent material or a phosphorescent material. The fluorescent material is an organic compound or a metal complex. Examples of the metal complex include boron complexes, zinc complexes, and aluminum complexes.

The phosphorescent material is a metal complex such as an iridium complex, a platinum complex, a rhenium complex, a copper complex, a europium complex, or a ruthenium complex. In particular, the iridium complex, which has a strong phosphorescent property, can be used. The light-emitting layer may include a plurality of fluorescent materials or phosphorescent materials in order to assist transmission of excitons or carriers.

As the hole-injecting or transporting compound, a material having high hole mobility can be used. Examples of the low or high molecular material having hole-injecting or transporting ability include, but not limited to, triarylamine derivatives, phenylenediamine derivatives, stilbene derivatives, phthalocyanine derivatives, porphyrin derivatives, poly(vinylcarbazole), poly(thiophene), and other electrically conductive polymers.

The host compound should allow both electrons and holes to flow. Examples of such compounds include, but not limited to, fused ring compounds (e.g., fluorene derivatives, naphthalene derivatives, anthracene derivatives, pyrene derivatives, carbazole derivatives, quinoxaline derivatives, and quinoline derivatives), organic aluminum complexes such as tris(8-quinolinolate)aluminum, organic zinc complexes, triphenylamine derivatives, and polymer derivatives such as poly(fluorene) derivatives and poly(phenylene) derivatives.

The electron-injecting or transporting compound are appropriately selected by considering, for example, the balance with the hole mobility of the hole-injecting or transporting compound. Examples of the compound having electron-injecting or transporting ability include, but not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

Table 4 shows non-limiting examples of the organic compound that is used as a light-emitting material; and Table 5 shows non-limiting examples of the metal complex compound, the hole-injecting compound, the hole-transporting compound, the host compound, the electron-injecting compound, and the electron-transporting compound.
TABLE 4
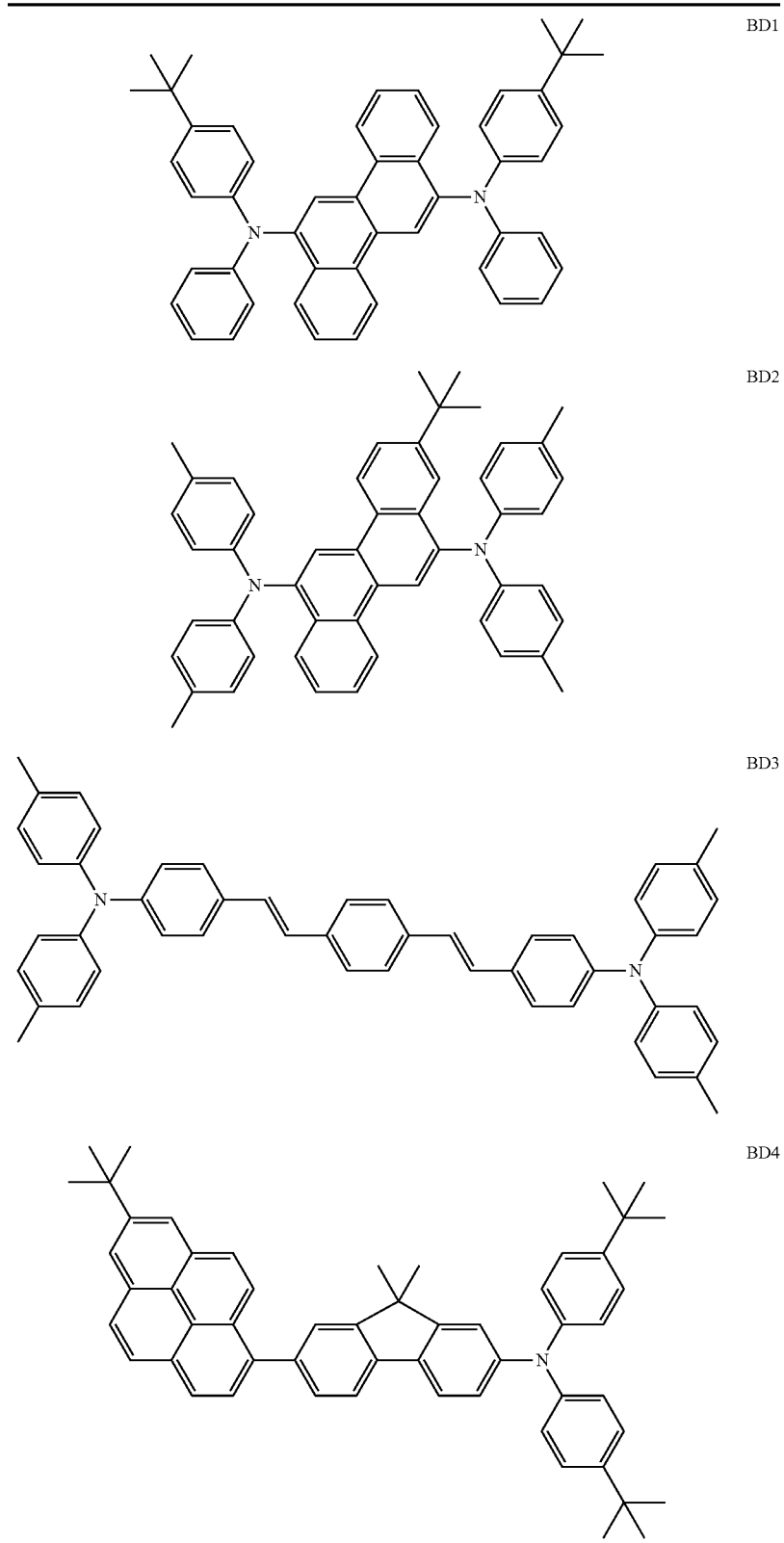

TABLE 4-continued
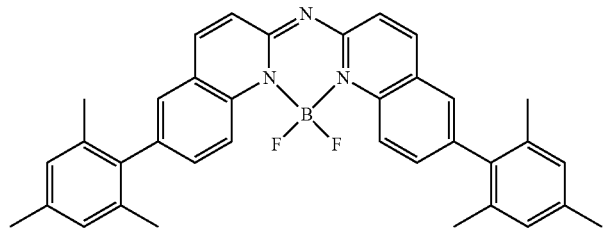
BD5
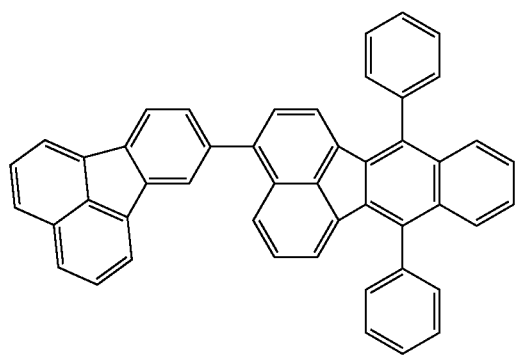 [SMILES: c1ccc(-c2c3c(c(-c4ccccc4)c4ccccc24)-c2ccc(-c4ccc5c(c4)-c4cccc6cccc-5c46)c4cccc-3c24)cc1]
BD6
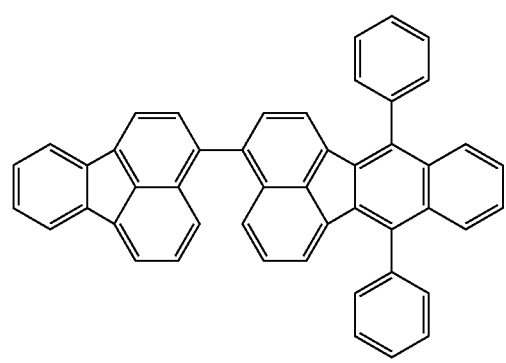 [SMILES: c1ccc(-c2c3c(c(-c4ccccc4)c4ccccc24)-c2ccc(-c4ccc5c6c(cccc46)-c4ccccc4-5)c4cccc-3c24)cc1]
BD7
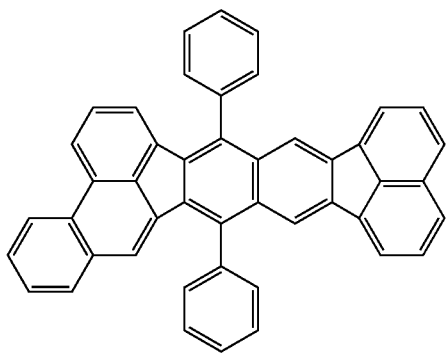 [SMILES: c1ccc(-c2c3cc4c(cc3c(-c3ccccc3)c3c5cc6ccccc6c6cccc(c23)c65)c2cccc3cccc4c32)cc1]
BD8
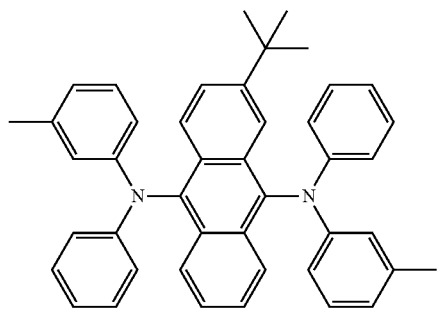
GD1

TABLE 4-continued
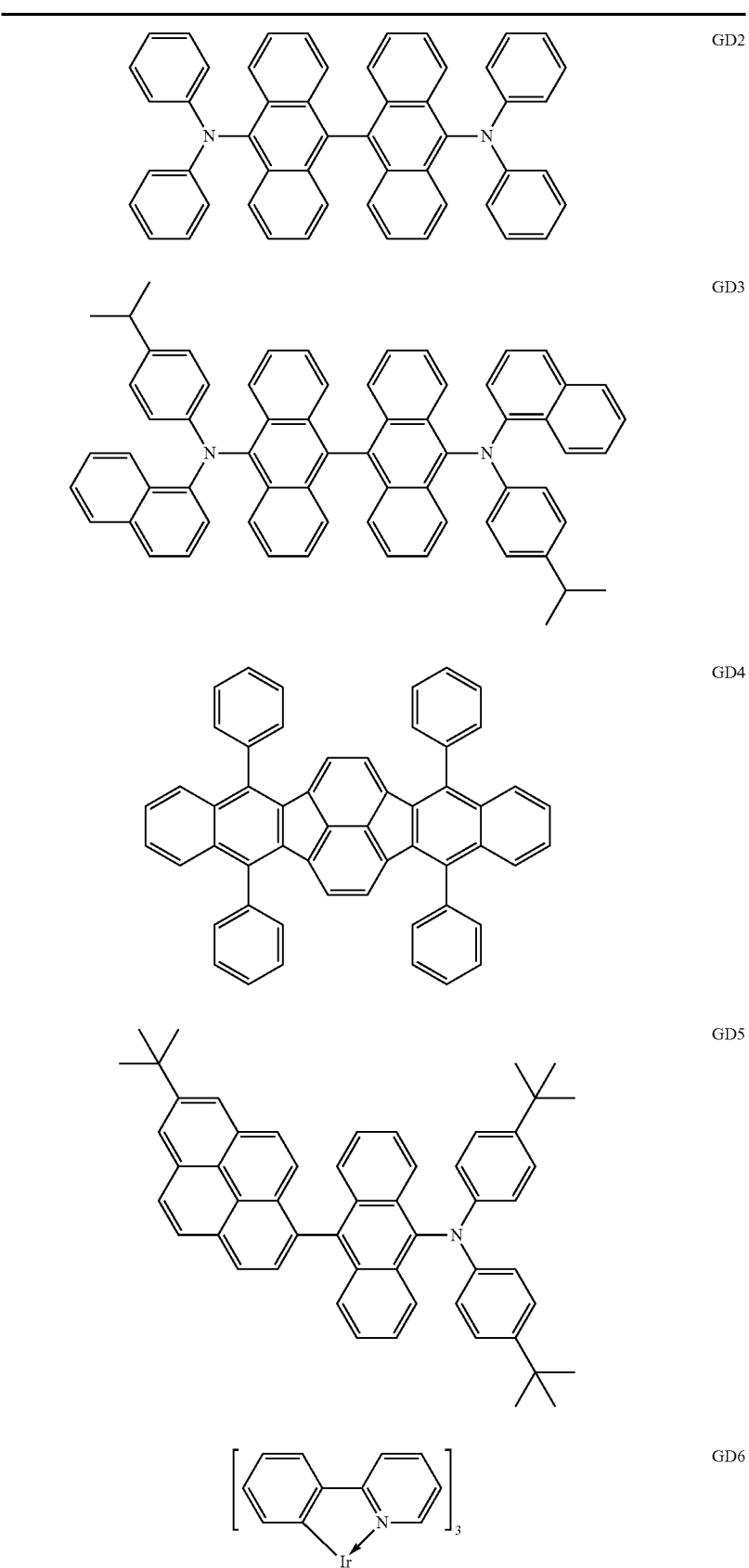

TABLE 4-continued
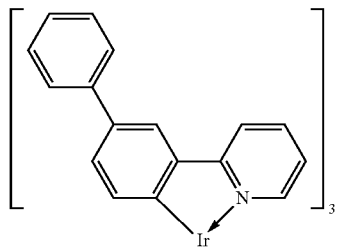
GD7
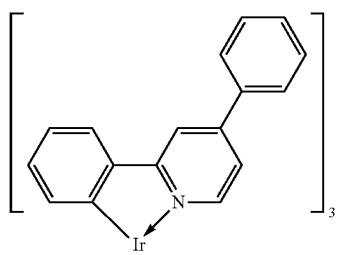
GD8
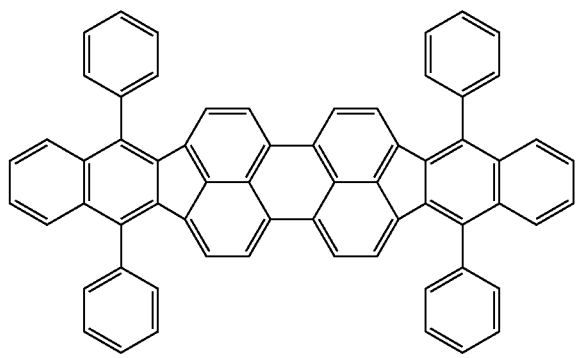 [SMILES: c1ccc(-c2c3c(c(-c4ccccc4)c4ccccc24)-c2ccc4c5ccc6c7c(ccc(c8ccc-3c2c84)c75)-c2c-6c(-c3ccccc3)c3ccccc3c2-c2ccccc2)cc1]
RD1
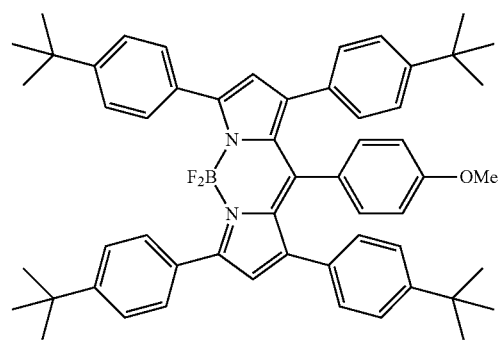
RD2
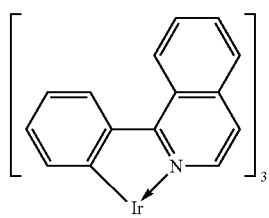
RD3

TABLE 4-continued
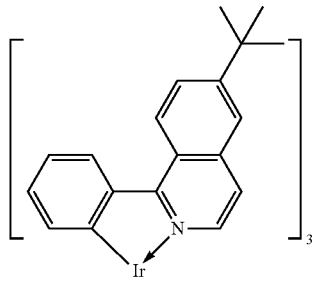
RD4
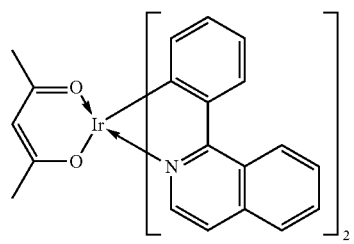
RD5
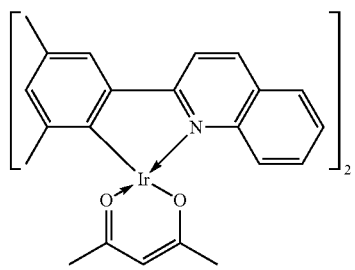
RD6
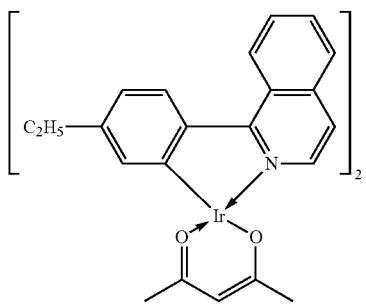
RD7
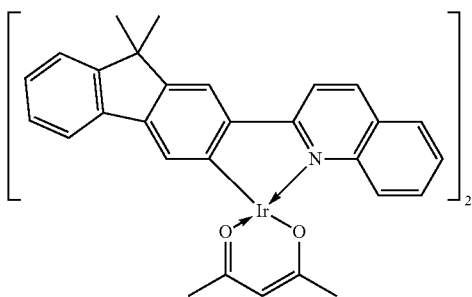
RD8

TABLE 5
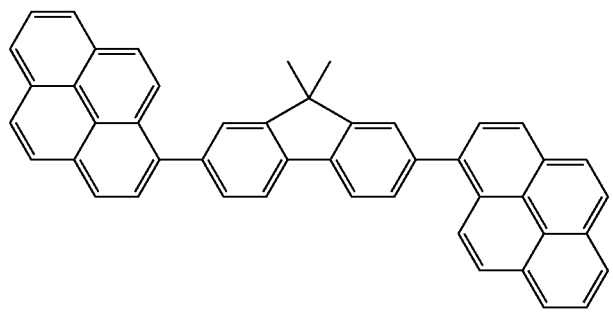 [SMILES: CC1(C)c2cc(-c3ccc4ccc5cccc6ccc3c4c56)ccc2-c2ccc(-c3ccc4ccc5cccc6ccc3c4c56)cc21] H1
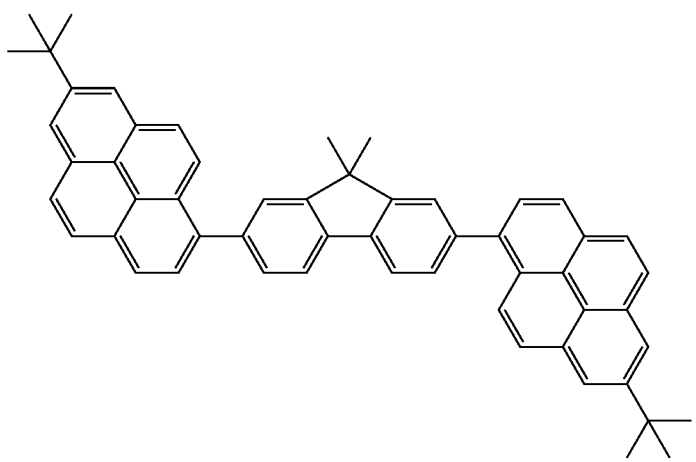 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] H2
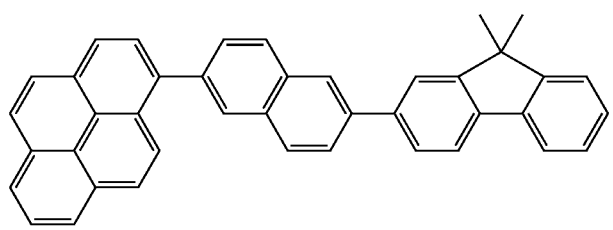 [SMILES: CC1(C)c2ccccc2-c2ccc(-c3ccc4cc(-c5ccc6ccc7cccc8ccc5c6c78)ccc4c3)cc21] H3
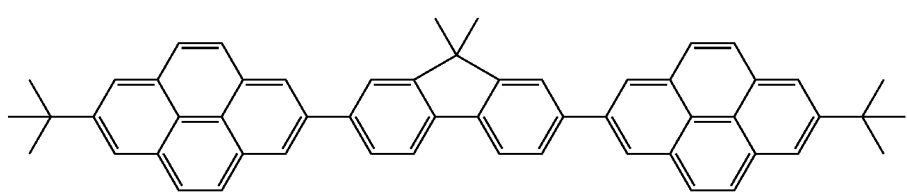 [SMILES: CC(C)(C)c1cc2ccc3cc(-c4ccc5c(c4)C(C)(C)c4cc(-c6cc7ccc8cc(C(C)(C)C)cc9ccc(c6)c7c89)ccc4-5)cc4ccc(c1)c2c34] H4
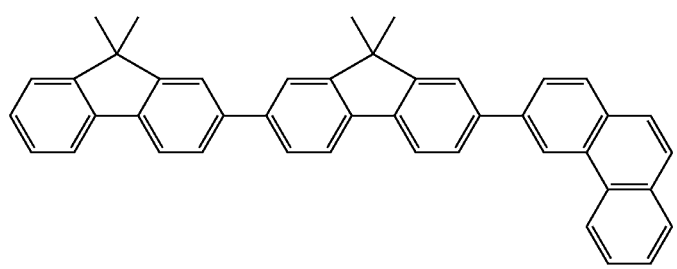 [SMILES: CC1(C)c2ccccc2-c2ccc(-c3ccc4c(c3)C(C)(C)c3cc(-c5ccc6ccc7ccccc7c6c5)ccc3-4)cc21] H5

TABLE 5-continued
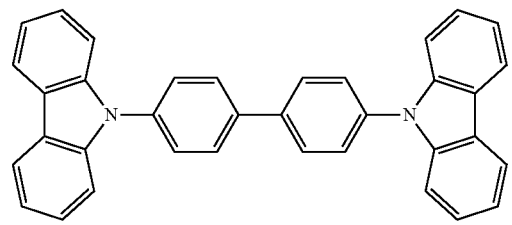 [SMILES: c1ccc2c(c1)c1ccccc1n2-c1ccc(-c2ccc(-n3c4ccccc4c4ccccc43)cc2)cc1]
H6
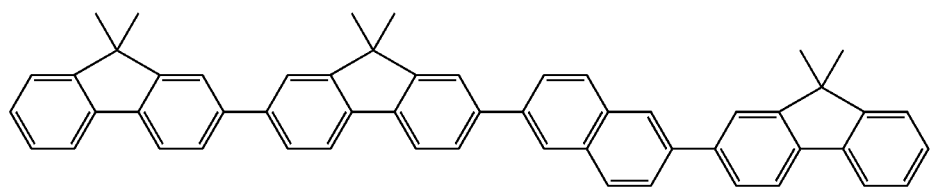 [SMILES: CC1(C)c2ccccc2-c2ccc(-c3ccc4c(c3)C(C)(C)c3cc(-c5ccc6cc(-c7ccc8c(c7)C(C)(C)c7ccccc7-8)ccc6c5)ccc3-4)cc21]
H7
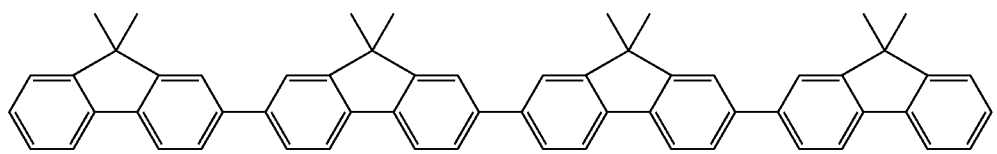 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]
H8
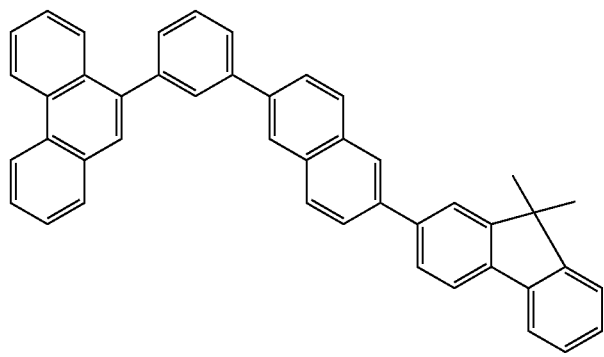 [SMILES: CC1(C)c2ccccc2-c2ccc(-c3ccc4cc(-c5cccc(-c6cc7ccccc7c7ccccc67)c5)ccc4c3)cc21]
H9
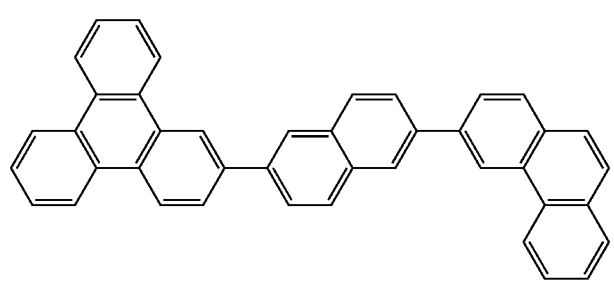 [SMILES: c1ccc2c(c1)ccc1ccc(-c3ccc4cc(-c5ccc6c7ccccc7c7ccccc7c6c5)ccc4c3)cc12]
H10
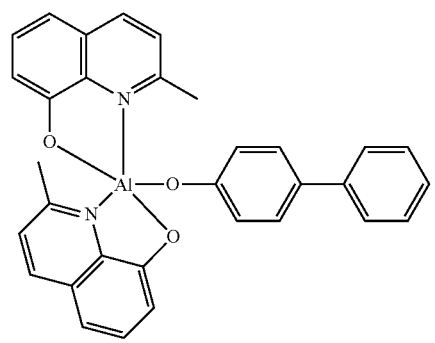
H11

TABLE 5-continued
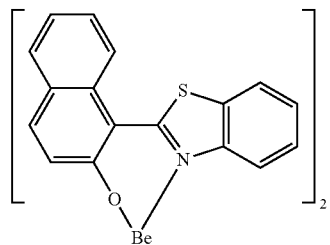 H12
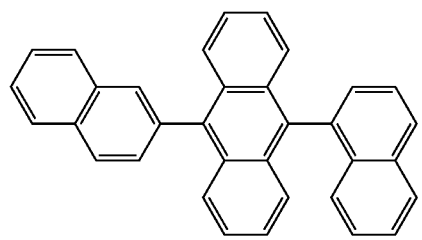 [SMILES: c1ccc2cc(-c3c4ccccc4c(-c4cccc5ccccc45)c4ccccc34)ccc2c1] H13
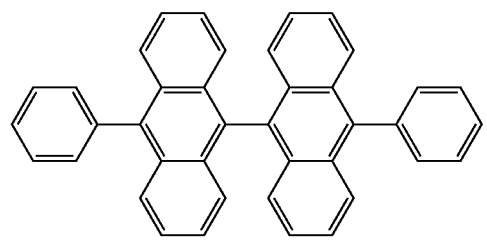 [SMILES: c1ccc(-c2c3ccccc3c(-c3c4ccccc4c(-c4ccccc4)c4ccccc34)c3ccccc23)cc1] H14
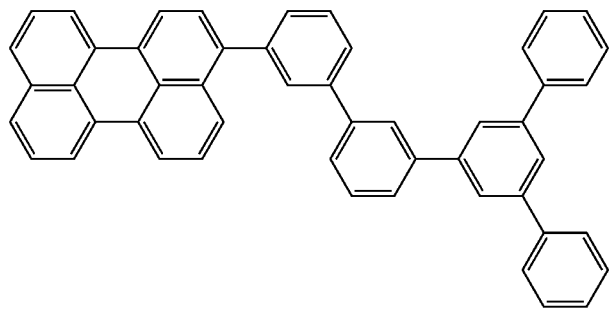 [SMILES: c1ccc(-c2cc(-c3ccccc3)cc(-c3cccc(-c4cccc(-c5ccc6c7cccc8cccc(c9cccc5c96)c87)c4)c3)c2)cc1] H15
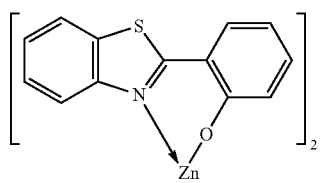 H16
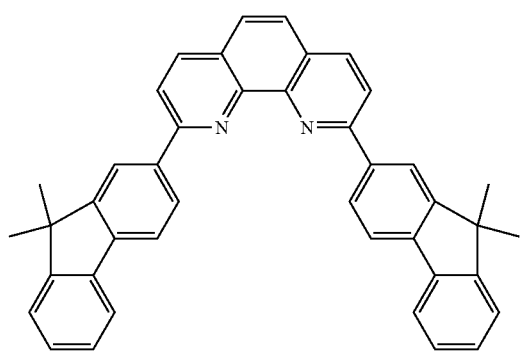 H17

TABLE 5-continued
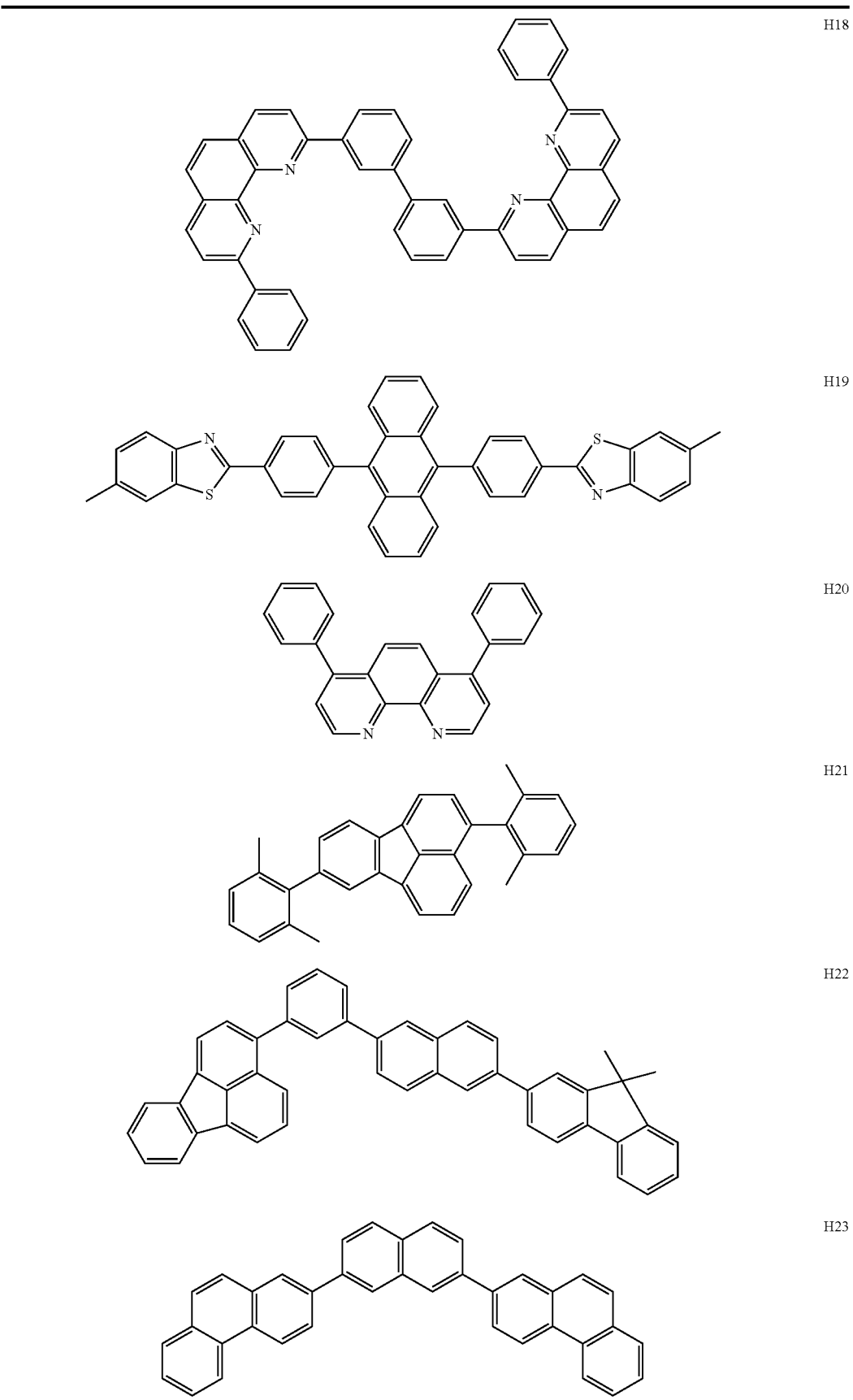
H18
H19
H20
H21
H22
H23

TABLE 5-continued
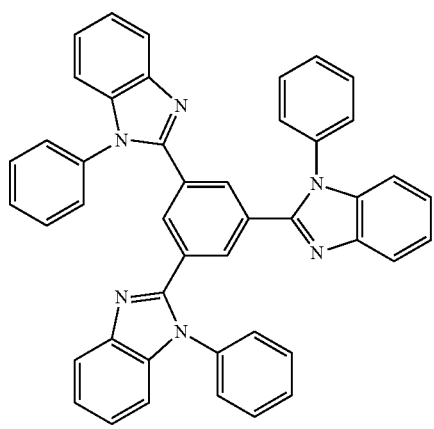 [SMILES: c1ccc(-n2c(-c3cc(-c4nc5ccccc5n4-c4ccccc4)cc(-c4nc5ccccc5n4-c4ccccc4)c3)nc3ccccc32)cc1]   H24
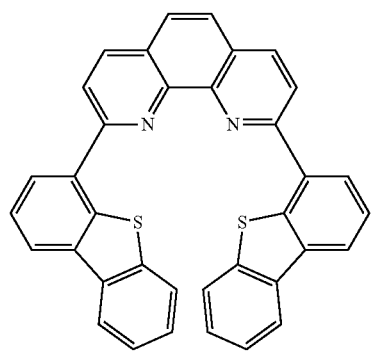 [SMILES: c1ccc2c(c1)sc1c(-c3ccc4ccc5ccc(-c6cccc7c6sc6ccccc67)nc5c4n3)cccc12]   H25
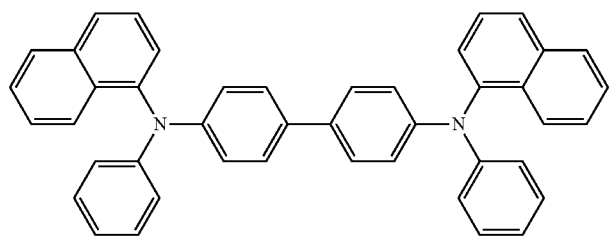 [SMILES: c1ccc(N(c2ccc(-c3ccc(N(c4ccccc4)c4cccc5ccccc45)cc3)cc2)c2cccc3ccccc23)cc1]   H26
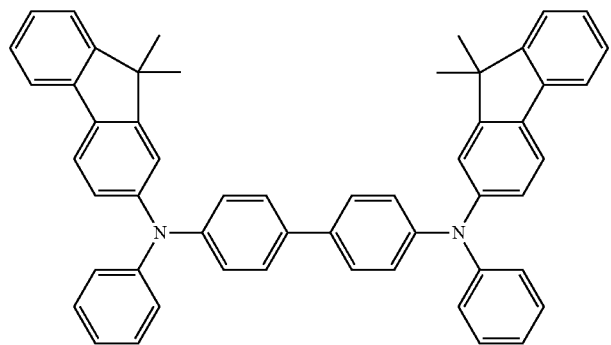 [SMILES: CC1(C)c2ccccc2-c2ccc(N(c3ccccc3)c3ccc(-c4ccc(N(c5ccccc5)c5ccc6c(c5)C(C)(C)c5ccccc5-6)cc4)cc3)cc21]   H27

TABLE 5-continued
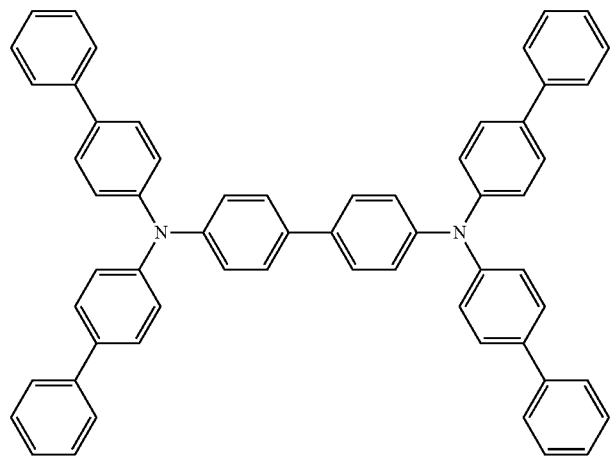 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
H28
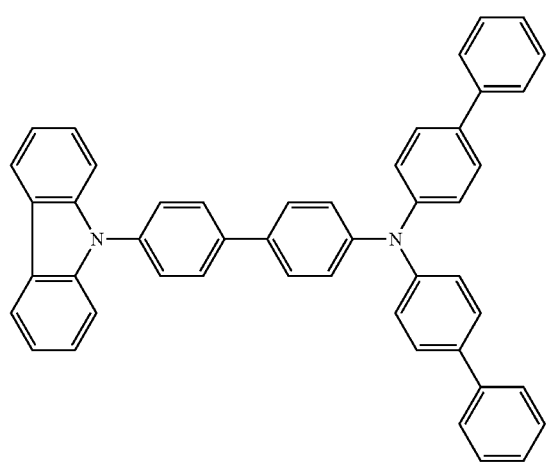 [SMILES: c1ccc(-c2ccc(N(c3ccc(-c4ccccc4)cc3)c3ccc(-c4ccc(-n5c6ccccc6c6ccccc65)cc4)cc3)cc2)cc1]
H29
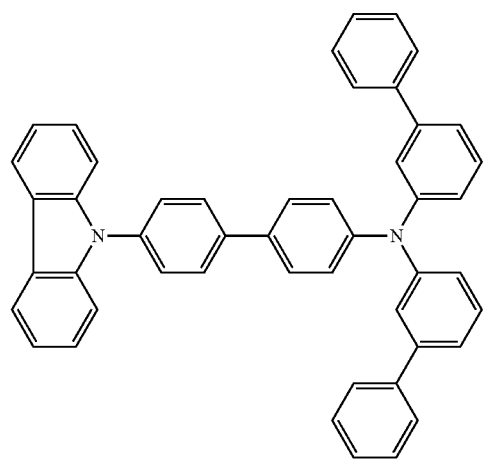 [SMILES: c1ccc(-c2cccc(N(c3ccc(-c4ccc(-n5c6ccccc6c6ccccc65)cc4)cc3)c3cccc(-c4ccccc4)c3)c2)cc1]
H30

TABLE 5-continued
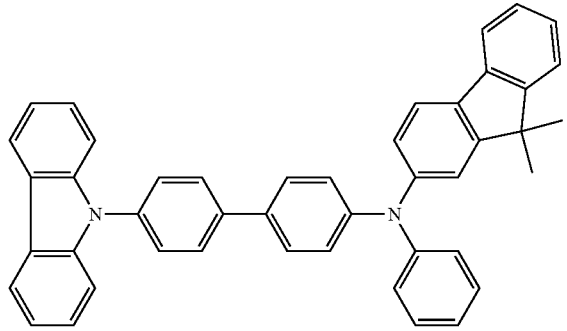 [SMILES: CC1(C)c2ccccc2-c2ccc(N(c3ccccc3)c3ccc(-c4ccc(-n5c6ccccc6c6ccccc65)cc4)cc3)cc21]
H31
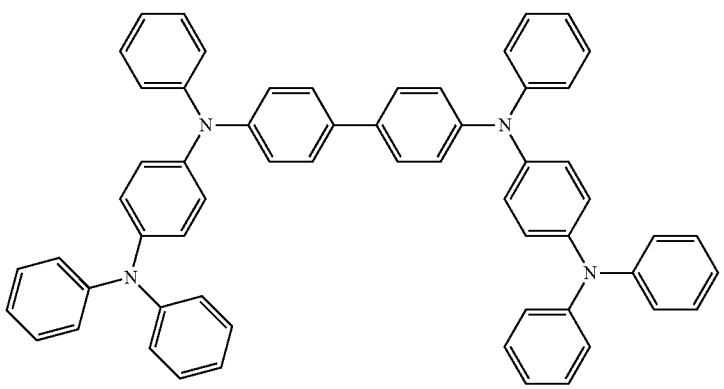 [SMILES: c1ccc(N(c2ccccc2)c2ccc(N(c3ccccc3)c3ccc(-c4ccc(N(c5ccccc5)c5ccc(N(c6ccccc6)c6ccccc6)cc5)cc4)cc3)cc2)cc1]
H32
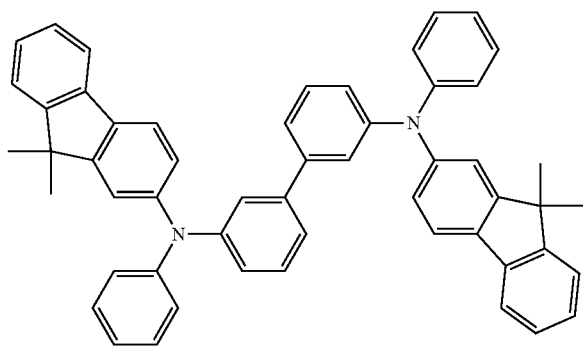
H33
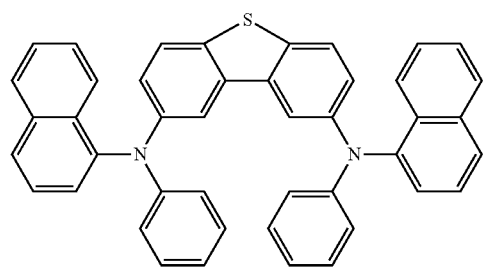 [SMILES: c1ccc(N(c2ccc3sc4ccc(N(c5ccccc5)c5cccc6ccccc56)cc4c3c2)c2cccc3ccccc23)cc1]
H34

TABLE 5-continued

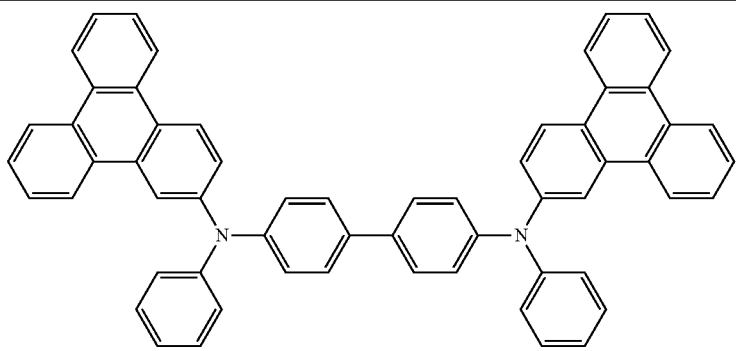

H35

As the constituent material of the anode, a material having a higher work function is used. Examples thereof include simple metals such as gold, platinum, silver, copper, nickel, palladium, cobalt, selenium, vanadium, and tungsten; alloys of two or more simple metals; and metal oxides such as tin oxide, zinc oxide, indium oxide, indium tin oxide (ITO), and indium zinc oxide.

In addition, electrically conductive polymers such as polyaniline, polypyrrole, and polythiophene can be used. These electrode materials may be used alone or in combination. The anode may have a monolayer structure or a multilayer structure.

In contrast, as the constituent material of the cathode, a material having a lower work function is used, and examples thereof include alkali metals such as lithium; alkaline earth metals such as calcium; simple metals such as aluminum, titanium, manganese, silver, lead, and chromium; and alloys of two or more simple metals.

For example, alloys such as magnesium-silver, aluminum-lithium, and aluminum-magnesium can be used. In addition, metal oxides such as indium tin oxide (ITO) can be used. These electrode materials may be used alone or in combination. The cathode may have a monolayer structure or a multilayer structure.

In the organic light-emitting device of the embodiment, a layer containing the organic compound according to the embodiment and layers of other organic compounds are formed by the following methods:

Thin films are formed by vacuum vapor deposition, ionized vapor deposition, sputtering, plasma coating, or known coating (e.g., spin coating, dipping, a casting method, an LB method, or an ink-jetting method) of compounds dissolved in appropriate solvents.

In a case of forming a layer by vacuum vapor deposition, solution coating, or the like, crystallization hardly occurs, and the resulting layer shows excellent stability for a long time. In addition, in coating, a film can be formed in combination with an appropriate binder resin.

Examples of the binder resin include, but not limited to, polyvinyl carbazole resins, polycarbonate resins, polyester resins, ABS resins, acrylic resins, polyimide resins, phenol resins, epoxy resins, silicone resins, and urea resins. These binder resins may be used alone as a homopolymer or a copolymer or in combination of two or more thereof. In addition, known additives such as a plasticizer, an antioxidant, and a UV absorber may be optionally contained in the films.

Use of Organic Light-Emitting Device According to the Embodiment

The organic light-emitting device of the present invention can be used as a constituent member of a display apparatus or a lighting system. Other examples of use include exposure light sources of electrophotographic image forming apparatuses, backlights of liquid crystal display apparatuses, color filterless white light sources, and light-emitting apparatuses including color filters, white light sources, and other components.

The color filter transmits at least one color of, for example, red, green, and blue. The light-emitting apparatus may be a combination of a filter for controlling the chromaticity of white and a white light source.

The display apparatus includes the organic light-emitting device of the embodiment in a display section. This display section includes a plurality of pixels, and the pixels each include the organic light-emitting device of the embodiment and an active device connected to the organic light-emitting device.

An example of the active device is a switching device or amplifier device for controlling luminance, more specifically, a transistor.

The anode or the cathode of the organic light-emitting device is electrically connected to the drain electrode or the source electrode of the transistor. Here, the display apparatus can be used as a display unit of, for example, a PC.

The display apparatus may be an image information processing apparatus that includes an image input section for inputting image information from, for example, an area CCD, a linear CCD, or a memory card and displays the input image on the display section.

The display section of an image pickup apparatus or ink-jet printer may have an image-outputting function for displaying image information input from the outside and an inputting function as an operating panel for inputting information to be processed into an image. The display apparatus may be used in the display section of a multi-functional printer.

The lighting system is an apparatus for lighting, for example, a room. The lighting system may emit light of white, neutral white, or any color from blue to red.

In the embodiment, the white color has a color temperature of about 4200 K, and the neutral white color has a color temperature of about 5000 K. The lighting system may have a color filter.

The lighting system according to the embodiment include the organic light-emitting device according to the embodiment and an AC/DC converter circuit connected to the organic light-emitting device for supplying a drive voltage.

The AC/DC converter circuit according to the embodiment converts AC voltage to DC voltage.

The image-forming apparatus according to the embodiment includes a photosensitive member, a charging unit for charging a surface of the photosensitive member, an exposure unit for forming an electrostatic latent image by exposing the photosensitive member to light, and a developing unit for developing the electrostatic latent image formed on the surface of the photosensitive member. The exposure unit includes the organic light-emitting device of the embodiment.

An example of the exposure unit is an exposure machine including the organic light-emitting device according to the embodiment. In the exposure machine, the organic light-emitting devices may be arranged in lines. Alternatively, the exposure machine may have a configuration such that the entire exposure side emits light.

The organic compound of the present invention can also be used in an organic solar cell, an organic TFT, an in vivo fluorescence recognizing material, a film, or a filter, in addition to the organic light-emitting device.

A display apparatus including the organic light-emitting device of the embodiment will now be described with reference to FIG. 1.

FIG. 1 is a schematic cross-sectional view of a display apparatus having the organic light-emitting devices of the embodiment and TFT devices as an example of the transistors connected to the organic light-emitting devices. FIG. 1 shows two pairs of the organic light-emitting device and the TFT device of a display apparatus 20. The structure will now be described in detail.

The display apparatus 20 shown in FIG. 1 include a substrate 1 such as a glass substrate and a moisture-proof protective film 2 disposed above the substrate 1 for protecting the TFT devices or the organic compound layer. Reference numeral 3 denotes a metal gate electrode, reference numeral 4 denotes a gate insulating film, and reference numeral 5 denotes a semiconductor layer.

The TFT device 8 includes a semiconductor layer 5, a drain electrode 6, and a source electrode 7. An insulating film 9 is disposed above the TFT device 8. The anode 11 of the organic light-emitting device is connected to the source electrode 7 via a contact hole 10.

The display apparatus is not limited to this configuration as long as either the anode or the cathode is connected to either the source electrode or the drain electrode of the TFT device.

The active device of the organic light-emitting device according to the embodiment may be directly formed on a substrate such as a Si substrate. Direct formation on a substrate means that a transistor is formed by machining a substrate itself such as a Si substrate.

In the display apparatus 20 shown in FIG. 1, the organic compound layer 12, which is a monolayer or a multilayer, is shown as one layer. Furthermore, a first protective layer 14 and a second protective layer 15 are disposed on the cathode 13 to prevent the organic light-emitting device from deteriorating.

The display apparatus according to the embodiment can also use an MIM device as a switching device, instead of the transistor.

The transistor is not limited to transistors using a single-crystalline silicon wafers and may be a thin film transistor having an active layer on the insulating surface of a substrate. The thin film transistor is also called a TFT device.

The thin film transistor may be a thin film transistor using single crystal silicon as the active layer, a thin film transistor using non-single crystalline silicon such as amorphous silicon or fine-crystalline silicon as the active layer, or a thin film transistor using non-single crystalline oxide semiconductor such as indium zinc oxide (IZO) or indium gallium zinc oxide (IGZO) as the active layer.

EXAMPLES

Example 1

Synthesis of Example Compound A4

[Chem. 24]

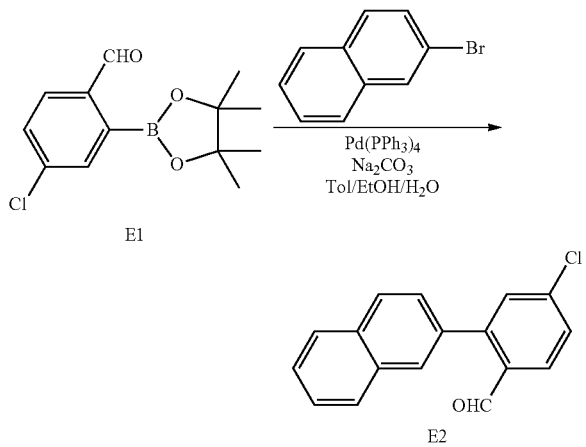

(1) Synthesis of Compound E2

The following reagents and solvents:

Compound E1: 8.00 g (30 mmol), 2-bromonaphthalene: 6.42 g (31 mmol), tetrakis(triphenylphosphine)palladium(0): 1.0 g (0.86 mmol), toluene: 100 mL, ethanol: 50 mL, and an aqueous 10 wt % sodium carbonate solution: 50 mL were put into a 300-mL three-neck flask.

This reaction solution was heated under reflux with stirring under a nitrogen atmosphere for 3 hours. After the completion of the reaction, the reaction solution was washed with water, was dried over sodium sulfate, and was then concentrated to give a crude product. Subsequently, the crude product was purified by silica gel column chromatography (eluent: toluene/heptane=2/1) to give 6.56 g (yield: 82%) of Compound E2.

[Chem. 25]

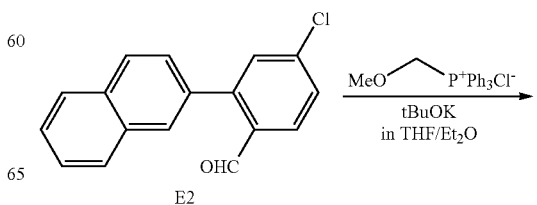

-continued

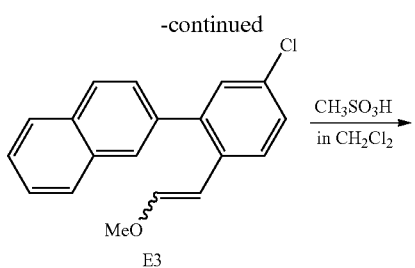

(2) Synthesis of Compound E4
The following reagent and solvent:
(methoxymethyl)triphenylphosphonium chloride: 18.0 g (52.5 mmol), and
dehydrated diethyl ether: 90 mL
were put into a nitrogen-purged 200-mL three-neck flask and were stirred.

Subsequently, 52.5 mL (52.5 mmol) of a solution of 1 M potassium tert-butoxide in THF was added to the reaction solution, followed by stirring for 1 hour. Subsequently, a solution of 5.33 g (20.0 mmol) of intermediate E2 dissolved in 250 mL of a THF solvent was added to the reaction solution, followed by stirring at room temperature for 3.5 hours. Water was then added to the reaction solution to stop the reaction. Subsequently, the aqueous phase was extracted with ethyl acetate by liquid-liquid separation three times, and the organic phase was washed with water, was dried over sodium sulfate, and was then concentrated to give a crude product. Subsequently, the crude product was purified by silica gel column chromatography (eluent: heptane/toluene=3/1) to give 5.35 g (yield: 90%) of intermediate E3.

A nitrogen-purged 100-mL recovery flask was fed with intermediate E3 (2.97 g (10 mmol)) and dehydrated dichloromethane (100 mL). The mixture was stirred, and 0.2 mL of methanesulfonic acid was added thereto, followed by stirring at room temperature for 2 hours. Methanol was then added to the reaction solution to stop the reaction. The precipitated yellow deposit was collected by filtration and was purified by silica gel column chromatography (eluent: heptane/toluene=4/1), followed by recrystallization from a solvent mixture of octane and toluene to give 2.31 g (yield: 88%) of intermediate E4, 3-chlorochrysene.

(3) Synthesis of Compound A4

[Chem. 26]

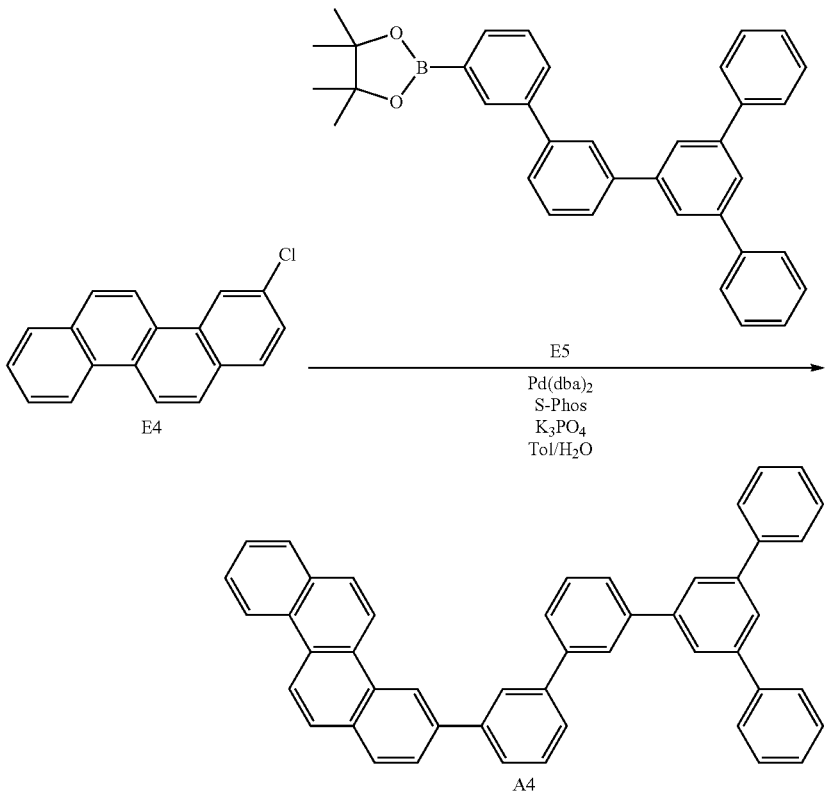

The following reagents and solvents:
intermediate E4: 525 mg (2.00 mmol),
boronic acid Compound E5: 1017 mg (2.00 mmol),
palladium(II) acetate: 18 mg (80 μmol),
dicyclohexyl(2',6'-dimethoxybiphenyl-2-yl)phosphine: 80 mg (194 μmol), potassium phosphate: 1.06 g (5.00 mmol), and
toluene: 50 mL
were put into a 100-mL recovery flask.

This reaction solution was heated under reflux with stirring for 8 hours. After the completion of the reaction, water was added to the reaction solution to perform liquid-liquid separation, followed by purification by silica gel column chromatography (eluent: heptane/toluene=4/1) and then recrystallization from toluene/ethanol. The resulting crystals were vacuum dried at 150° C. and were purified by sublimation to give 830 mg (yield: 68%) of Example Compound A4.

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=608.89, calculated value: $C_{48}H_{32}$=608.25

The energy gap of Example Compound A4 was measured by the following process:

Example Compound A4 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A4 was determined to be 3.4 eV from the absorption edge of the resulting absorption spectrum.

Example 2

Synthesis of Example Compound A9

Example Compound A9 was prepared as in Example 1 except that Compound E6 shown below was used in place of Compound E5 in Example 1, (3).

[Chem. 27]

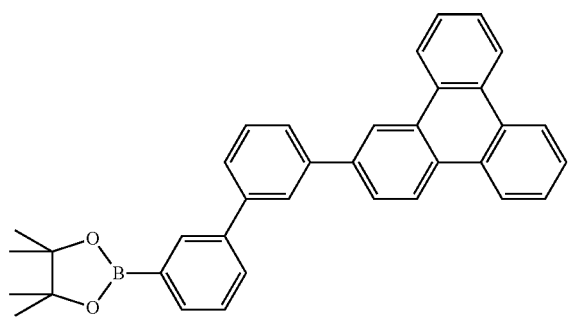

E6

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=606.86, calculated value: $C_{48}H_{30}$=606.23.

The energy gap of Example Compound A9 was measured by the following process:

Example Compound A9 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A9 was determined to be 3.4 eV from the absorption edge of the resulting absorption spectrum.

Example 3

Synthesis of Example Compound A10

Example Compound A10 was prepared as in Example 1 except that Compound E7 shown below was used in place of Compound E5 in Example 1, (3).

[Chem. 28]

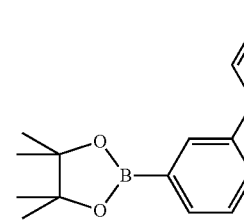

E7

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=580.17, calculated value: $C_{46}H_{28}$=580.71.

The energy gap of Example Compound A10 was measured by the following process:

Example Compound A10 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A10 was determined to be 2.9 eV from the absorption edge of the resulting absorption spectrum.

Example 4

Synthesis of Example Compound A11

Example Compound A11 was prepared as in Example 1 except that Compound E8 shown below was used in place of Compound E5 in Example 1, (3).

[Chem. 29]

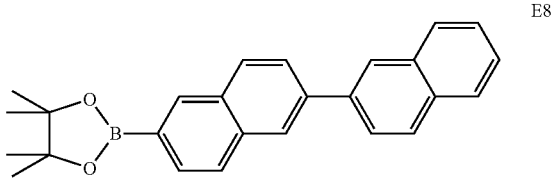

E8

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=480.10, calculated value: $C_{38}H_{24}$=480.19.

The energy gap of Example Compound A11 was measured by the following process:

Example Compound A11 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A11 was determined to be 3.3 eV from the absorption edge of the resulting absorption spectrum.

Example 5

Synthesis of Example Compound A12

Example Compound A12 was prepared as in Example 1 except that Compound E9 shown below was used in place of Compound E5 in Example 1, (3).

[Chem. 30]

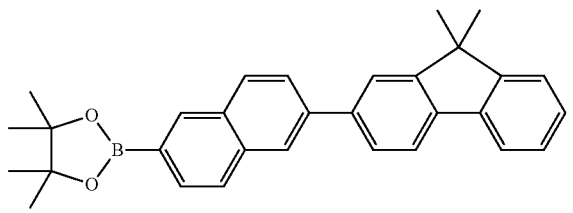

E9

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=546.46, calculated value: $C_{43}H_{30}$=546.23.

The energy gap of Example Compound A12 was measured by the following process:

Example Compound A12 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A12 was determined to be 3.3 eV from the absorption edge of the resulting absorption spectrum.

Example 6

Synthesis of Example Compound A15

[Chem. 31]

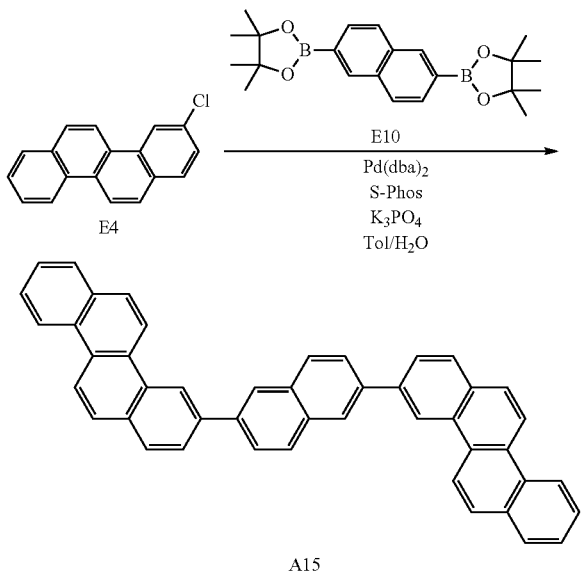

A15

The following reagents and solvents: intermediate E4: 578 mg (2.2 mmol),
boronic acid Compound E10: 380 mg (1.0 mmol),
palladium(II) acetate: 18 mg (80 μmol),
dicyclohexyl(2',6'-dimethoxybiphenyl-2-yl)phosphine: 80 mg (194 μmol),
potassium phosphate: 1.06 g (5.00 mmol), and
toluene: 50 mL
were put into a 100-ml recovery flask.

This reaction solution was heated under reflux with stirring for 8 hours. After the completion of the reaction, water was added to the reaction solution to perform liquid-liquid separation, followed by purification by silica gel column chromatography (eluent: heptane/toluene=4/1) and then recrystallization from toluene/ethanol. The resulting crystals were vacuum dried at 150° C. and were purified by sublimation to give 337 mg (yield: 58%) of Example Compound A15.

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=580.43, calculated value: $C_{46}H_{28}$=580.22.

The energy gap of Example Compound A15 was measured by the following process:

Example Compound A15 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A15 was determined to be 3.2 eV from the absorption edge of the resulting absorption spectrum.

Example 7

Synthesis of Example Compound A16

Example Compound A16 was prepared as in Example 1 except that Compound E11 shown below was used in place of Compound E5 in Example 1, (3).

[Chem. 32]

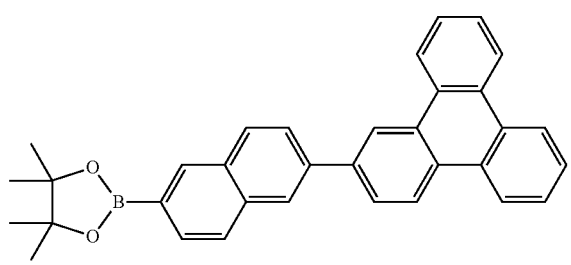

E11

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=580.13, calculated value: $C_{46}H_{28}$=580.22.

The energy gap of Example Compound A16 was measured by the following process:

Example Compound A16 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A16 was determined to be 3.3 eV from the absorption edge of the resulting absorption spectrum.

Example 8

Synthesis of Example Compound A18

Example Compound A18 was prepared as in Example 1 except that Compound E12 shown below was used in place of Compound E5 in Example 1, (3).

[Chem. 33]

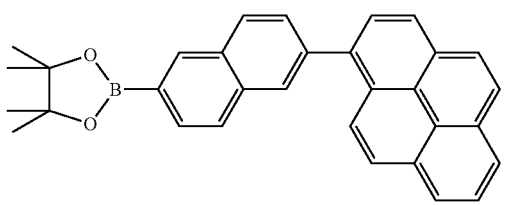

E12

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=554.65, calculated value: $C_{44}H_{26}$=554.20.

The energy gap of Example Compound A18 was measured by the following process:

Example Compound A18 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A18 was determined to be 3.0 eV from the absorption edge of the resulting absorption spectrum.

Example 9

Synthesis of Example Compound A27

Example Compound A27 was prepared as in Example 6 except that Compound E13 shown below was used in place of Compound E10 in Example 6.

[Chem. 34]

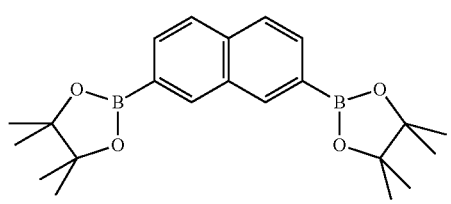

E13

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=580.44, calculated value: $C_{46}H_{28}$=580.22.

The energy gap of Example Compound A27 was measured by the following process:

Example Compound A27 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A27 was determined to be 3.2 eV from the absorption edge of the resulting absorption spectrum.

Example 10

Synthesis of Example Compound A14

Example Compound A14 was prepared as in Example 1 except that Compound E14 shown below was used in place of Compound E5 in Example 1, (3).

[Chem. 35]

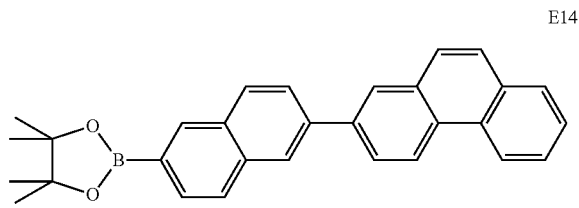

E14

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=530.41, calculated value: $C_{42}H_{26}$=530.66.

The energy gap of Example Compound A14 was measured by the following process:

Example Compound A14 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A14 was determined to be 3.2 eV from the absorption edge of the resulting absorption spectrum.

Example 11

Synthesis of Example Compound A35

Example Compound A35 was prepared as in Example 1 except that Compound E15 shown below was used in place of Compound E5 in Example 1, (3).

[Chem. 36]

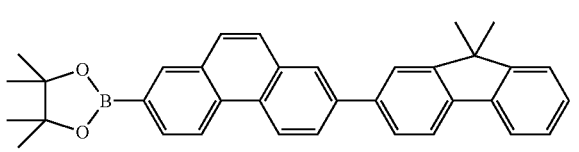

E15

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=596.25, calculated value: $C_{47}H_{32}$=596.76.

The energy gap of Example Compound A35 was measured by the following process:

Example Compound A35 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A35 was determined to be 3.1 eV from the absorption edge of the resulting absorption spectrum.

Example 12

Synthesis of Example Compound A48

Example Compound A48 was prepared as in Example 1 except that Compound E16 shown below was used in place of Compound E5 in Example 1, (3).

[Chem. 37]

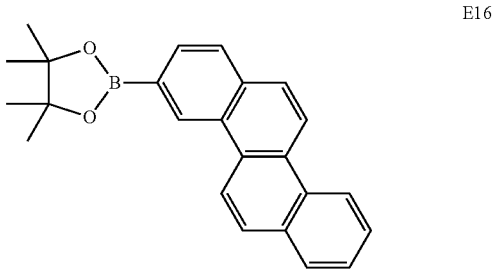

E16

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=454.67, calculated value: $C_{36}H_{22}$=454.17.

The energy gap of Example Compound A48 was measured by the following process:

Example Compound A48 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A48 was determined to be 3.1 eV from the absorption edge of the resulting absorption spectrum.

Example 13

Synthesis of Example Compound A65

Example Compound A65 was prepared as in Example 1 except that Compound E17 shown below was used in place of Compound E5 in Example 1, (3).

[Chem. 38]

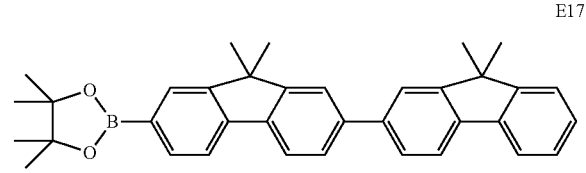

E17

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=612.88, calculated value: $C_{48}H_{36}$=612.28.

The energy gap of Example Compound A65 was measured by the following process:

Example Compound A65 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A65 was determined to be 3.2 eV from the absorption edge of the resulting absorption spectrum.

Example 14

Synthesis of Example Compound A70

Example Compound A70 was prepared as in Example 1 except that Compound E18 shown below was used in place of Compound E5 in Example 1, (3).

[Chem. 39]

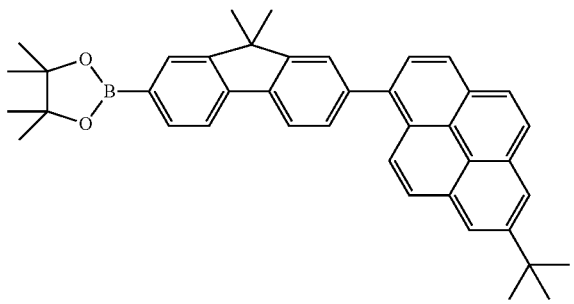

E18

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=676.75, calculated value: $C_{53}H_{40}$=676.88.

The energy gap of Example Compound A70 was measured by the following process:

Example Compound A70 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A70 was determined to be 2.9 eV from the absorption edge of the resulting absorption spectrum.

Example 15

Synthesis of Example Compound A82

Example Compound A82 was prepared as in Example 1 except that Compound E19 shown below was used in place of Compound E5 in Example 1, (3).

[Chem. 40]

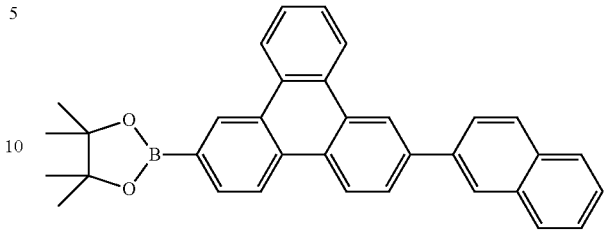

E19

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=580.28, calculated value: $C_{46}H_{28}$=580.22.

The energy gap of Example Compound A82 was measured by the following process:

Example Compound A82 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A82 was determined to be 3.2 eV from the absorption edge of the resulting absorption spectrum.

Example 16

Synthesis of Example Compound A87

Example Compound A87 was prepared as in Example 1 except that Compound E20 shown below was used in place of Compound E5 in Example 1, (3).

[Chem. 41]

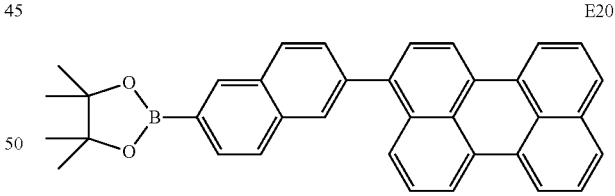

E20

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=604.12, calculated value: $C_{48}H_{28}$=604.74.

The energy gap of Example Compound A87 was measured by the following process:

Example Compound A87 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound A87 was determined to be 2.6 eV from the absorption edge of the resulting absorption spectrum.

Example 17

Synthesis of Example Compound B1

[Chem. 42]

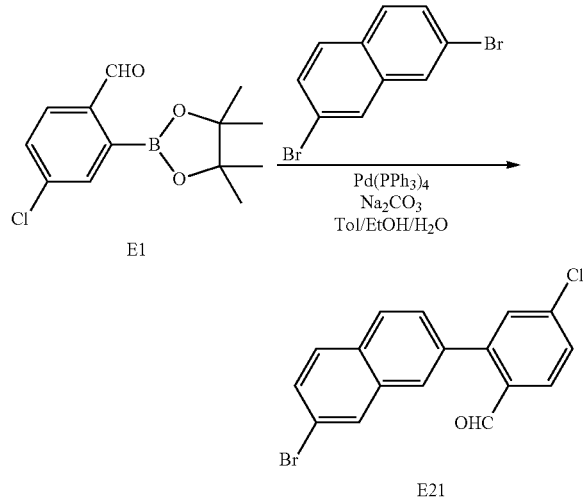

(1) Synthesis of Compound E21

The following reagents and solvents:
Compound E1: 8.00 g (30 mmol),
2,7-dibromonaphthalene: 9.43 g (33 mmol),
tetrakis(triphenylphosphine)palladium(0): 1.0 g (0.86 mmol),
toluene: 100 mL,
ethanol: 50 mL, and
an aqueous 10 wt % sodium carbonate solution: 50 mL were put into a 300-mL three-neck flask.

This reaction solution was stirred under a nitrogen atmosphere for reaction at 60° C. for 7 hours. After the completion of the reaction, the reaction solution was washed with water, was dried over sodium sulfate, and was then concentrated to give a crude product. Subsequently, the crude product was purified by silica gel column chromatography (eluent: toluene/heptane=2/1) to give 6.94 g (yield: 67%) of intermediate E21.

[Chem. 43]

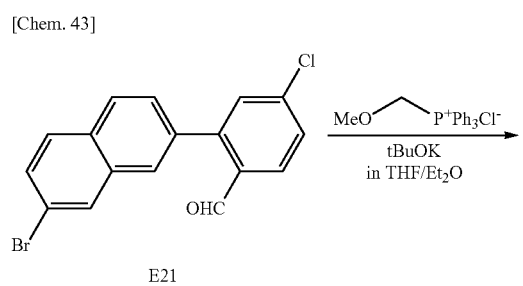

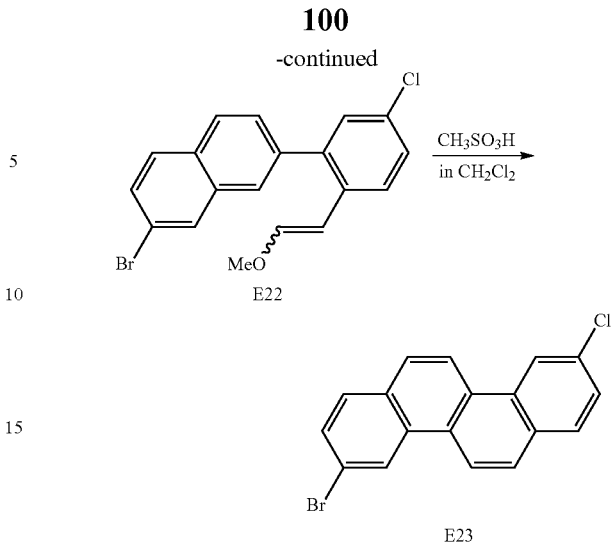

(2) Synthesis of Compound E23

The following reagent and solvent:
(methoxymethyl)triphenylphosphonium chloride: 18.0 g (52.5 mmol), and
dehydrated diethyl ether: 90 mL
were put into a nitrogen-purged 200-mL three-neck flask and were stirred.

Subsequently, 52.5 mL (52.5 mmol) of a solution of 1 M potassium tert-butoxide in THF was added to the reaction solution, followed by stirring for 1 hour. Subsequently, a solution of 6.87 g (20.0 mmol) of intermediate E21 dissolved in 250 mL of a THF solvent was added to the reaction solution, followed by stirring at room temperature for 3.5 hours. Water was then added to the reaction solution to stop the reaction. Subsequently, the aqueous phase was extracted with ethyl acetate by liquid-liquid separation three times, and the organic phase was washed with water, was dried over sodium sulfate, and was then concentrated to give a crude product. Subsequently, the crude product was purified by silica gel column chromatography (eluent: heptane/toluene=3/1) to give 5.1 g (yield: 86%) of intermediate E22.

A nitrogen-purged 100-mL recovery flask was fed with intermediate E22 (3.73 g (10 mmol)) and dehydrated dichloromethane (100 mL). The mixture was stirred, and 0.2 mL of methanesulfonic acid was added thereto, followed by stirring at room temperature for 2 hours. Methanol was then added to the reaction solution to stop the reaction. The precipitated yellow deposit was collected by filtration and was purified by silica gel column chromatography (eluent: heptane/toluene=4/1), followed by recrystallization from a solvent mixture of octane and toluene to give 2.90 g (yield: 85%) of intermediate E23, 3-bromo-9-chlorochrysene.

(3) Synthesis of Compound B1

[Chem. 44]

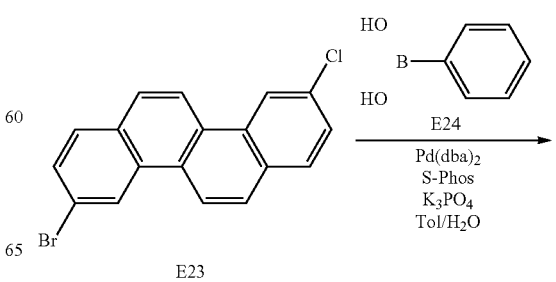

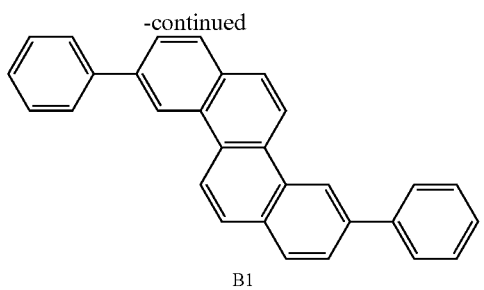

B1

The following reagents and solvents:
intermediate E23: 342 mg (1.0 mmol),
boronic acid Compound E24: 268 mg (2.2 mmol),
palladium(II) acetate: 18 mg (80 µmol),
dicyclohexyl(2',6'-dimethoxybiphenyl-2-yl)phosphine: 80 mg (194 µmol),
potassium phosphate: 1.06 g (5.0 mmol), and
toluene: 10 mL
were put into a 100-mL recovery flask.

This reaction solution was heated under reflux with stirring for 8 hours. After the completion of the reaction, water was added to the reaction solution to perform liquid-liquid separation, followed by purification by silica gel column chromatography (eluent: heptane/toluene=4/1) and then recrystallization from toluene/ethanol. The resulting crystals were vacuum dried at 150° C. and were purified by sublimation to give 285 mg (yield: 75%) of Example Compound B1.

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=380.11, calculated value: $C_{30}H_{20}$=380.16.

The energy gap of Example Compound B1 was measured by the following process:
Example Compound B1 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B1 was determined to be 3.3 eV from the absorption edge of the resulting absorption spectrum.

Example 18

Synthesis of Example Compound B2

Example Compound B2 was prepared as in Example 17 except that Compound E25 shown below was used in place of Compound E24 in Example 17, (3).

[Chem. 45]

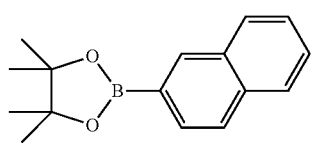

E25

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=480.48, calculated value: $C_{38}H_{24}$=480.19.

The energy gap of Example Compound B2 was measured by the following process:
Example Compound B2 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B2 was determined to be 3.2 eV from the absorption edge of the resulting absorption spectrum.

Example 19

Synthesis of Example Compound B12

[Chem. 46]

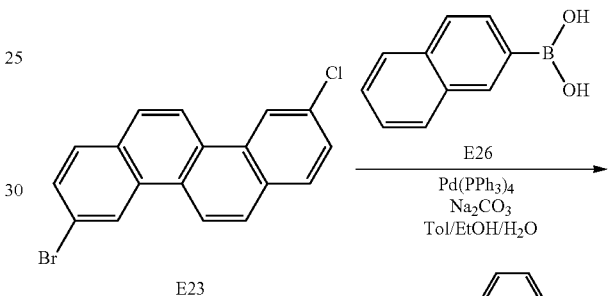

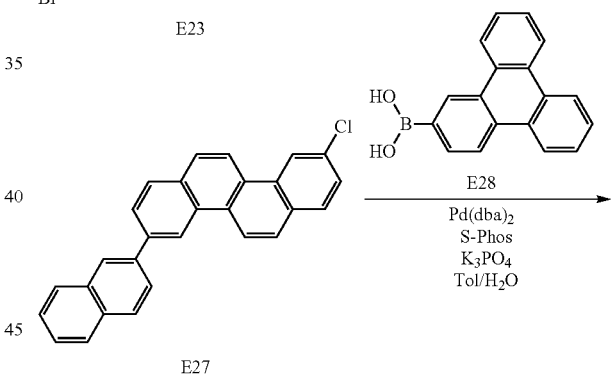

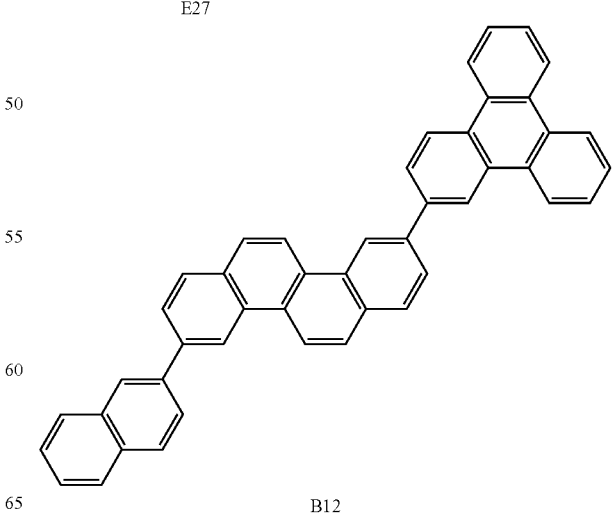

B12

(1) Synthesis of Compound E27

The following reagents and solvents:
intermediate E23: 1.23 g (3.0 mmol),
Compound E26: 0.53 g (3.1 mmol),
tetrakis(triphenylphosphine)palladium(0): 0.1 g (0.08 mmol),
toluene: 10 mL,
ethanol: 5 mL, and
an aqueous 10 wt % sodium carbonate solution: 5 mL
were put into a 100-mL recovery flask.

This reaction solution was heated under reflux with stirring under a nitrogen atmosphere for 5 hours. After the completion of the reaction, the reaction solution was washed with water, was dried over sodium sulfate, and was then concentrated to give a crude product. Subsequently, the crude product was purified by silica gel column chromatography (eluent: toluene/heptane=2/1) to give 0.99 g (yield: 85%) of intermediate E27.

(2) Synthesis of Example Compound B12

The following reagents and solvents:
intermediate E27: 389 mg (1.0 mmol),
boronic acid Compound E28: 272 mg (1.0 mmol),
palladium(II) acetate: 18 mg (80 μmol),
dicyclohexyl(2',6'-dimethoxybiphenyl-2-yl)phosphine: 80 mg (194 μmol),
potassium phosphate: 0.53 g (2.5 mmol), and
toluene: 10 mL
were put into a 100-mL recovery flask.

This reaction solution was heated under reflux with stirring for 8 hours. After the completion of the reaction, water was added to the reaction solution to perform liquid-liquid separation, followed by purification by silica gel column chromatography (eluent: heptane/toluene=4/1) and then recrystallization from toluene/ethanol. The resulting crystals were vacuum dried at 150° C. and were purified by sublimation to give 458 mg (yield: 79%) of Example Compound B12.

This compound was confirmed by HPLC to have a purity of 99% or more.

The resulting compound was identified as follows:
[MALDI-TOF-MS (matrix-assisted laser desorption-ionization time-of-flight mass spectrometry)(Autoflex LRF manufactured by Bruker Corporation)]
Observed value: m/z=580.01, calculated value: $C_{46}H_{28}$=580.22.

The energy gap of Example Compound B12 was measured by the following process:

Example Compound B12 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B12 was determined to be 3.2 eV from the absorption edge of the resulting absorption spectrum.

Example 20

Synthesis of Example Compound B14

Example Compound B14 was prepared as in Example 17 except that Compound E29 shown below was used in place of Compound E24 in Example 17, (3).

[Chem. 47]

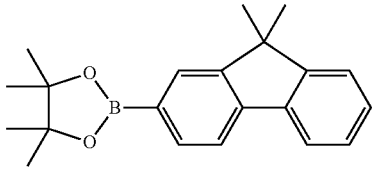

E29

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=612.55, calculated value: $C_{48}H_{36}$=612.28.

The energy gap of Example Compound B14 was measured by the following process:

Example Compound B14 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B14 was determined to be 3.1 eV from the absorption edge of the resulting absorption spectrum.

Example 21

Synthesis of Example Compound B16

Example Compound B16 was prepared as in Example 19 except that Compound E30 and Compound E31 shown below were used in place of Compound E26 in Example 19, (1) and Compound E28 in Example 19, (2), respectively.

[Chem. 48]

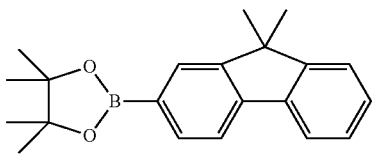

E30

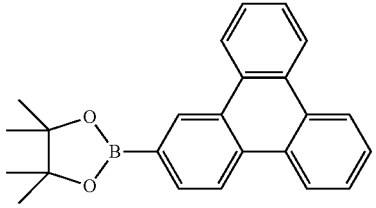

E31

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=646.54, calculated value: $C_{51}H_{34}$=646.82.

The energy gap of Example Compound B16 was measured by the following process:

Example Compound B16 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B16 was determined to be 3.1 eV from the absorption edge of the resulting absorption spectrum.

Example 22

Synthesis of Example Compound B18

Example Compound B18 was prepared as in Example 19 except that Compound E32 and Compound E33 were used in place of Compound E26 in Example 19, (1) and Compound E28 in Example 19, (2), respectively.

[Chem. 49]

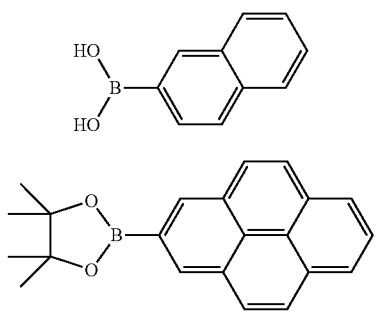

E32

E33

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]

Observed value: m/z=554.28, calculated value: $C_{44}H_{26}$=554.68.

The energy gap of Example Compound B18 was measured by the following process:

Example Compound B18 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B18 was determined to be 2.8 eV from the absorption edge of the resulting absorption spectrum.

Example 23

Synthesis of Example Compound B28

Example Compound B28 was prepared as in Example 19 except that Compound E34 and Compound E35 shown below were used in place of Compound E26 in Example 19, (1) and Compound E28 in Example 19, (2), respectively.

[Chem. 50]

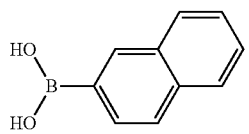

E34

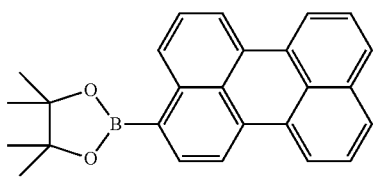

E35

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]

Observed value: m/z=604.30, calculated value: $C_{48}H_{28}$=604.22.

The energy gap of Example Compound B28 was measured by the following process:

Example Compound B28 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B28 was determined to be 2.5 eV from the absorption edge of the resulting absorption spectrum.

Example 24

Synthesis of Example Compound B33

Example Compound B33 was prepared as in Example 19 except that Compound E36 and Compound E37 shown below were used in place of Compound E26 in Example 19, (1) and Compound E28 in Example 19, (2), respectively.

[Chem. 51]

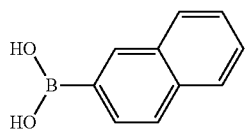

E36

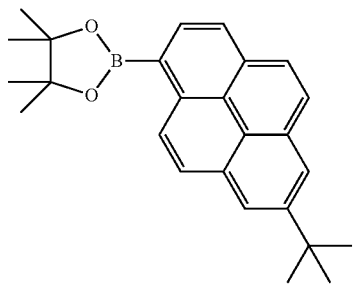

E37

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=610.29, calculated value: $C_{48}H_{34}$=610.78.

The energy gap of Example Compound B33 was measured by the following process:

Example Compound B33 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B33 was determined to be 2.9 eV from the absorption edge of the resulting absorption spectrum.

Example 25

Synthesis of Example Compound B38

Example Compound B38 was prepared as in Example 19 except that Compound E38 and Compound E39 shown below were used in place of Compound E26 in Example 19, (1) and Compound E28 in Example 19, (2), respectively.

[Chem. 52]

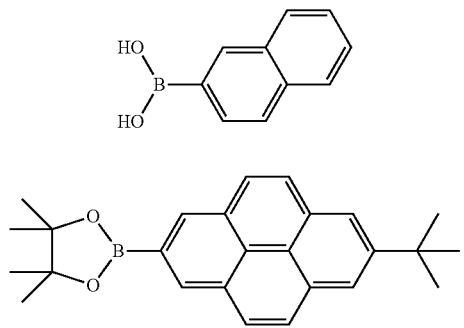

E38

E39

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=610.31, calculated value: $C_{48}H_{34}$=610.78.

The energy gap of Example Compound B38 was measured by the following process:

Example Compound B38 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B38 was determined to be 2.8 eV from the absorption edge of the resulting absorption spectrum.

Example 26

Synthesis of Example Compound B42

Example Compound B42 was prepared as in Example 19 except that Compound E40 and Compound E41 shown below were used in place of Compound E26 in Example 19, (1) and Compound E28 in Example 19, (2), respectively.

[Chem. 53]

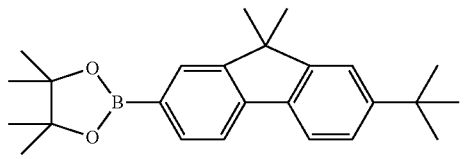

E40

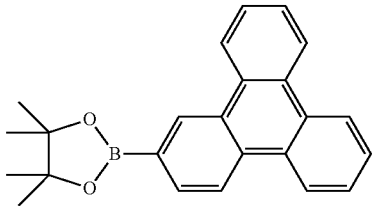

E41

This compound was confirmed by HPLC to have a purity of 99% or more.

The resulting compound was identified as follows:
[MALDI-TOF-MS (matrix-assisted laser desorption-ionization time-of-flight mass spectrometry) (Autoflex LRF manufactured by Bruker Corporation)]
Observed value: m/z=702.45, calculated value: $C_{55}H_{42}$=702.33.

The energy gap of Example Compound B42 was measured by the following process:

Example Compound B42 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound B42 was determined to be 3.2 eV from the absorption edge of the resulting absorption spectrum.

Example 27

Synthesis of Example Compound C4

Example Compound C4 was prepared as in Example 19 except that Compound E42 and Compound E43 shown below were used in place of Compound E26 in Example 19, (1) and Compound E28 in Example 19, (2), respectively.

[Chem. 54]

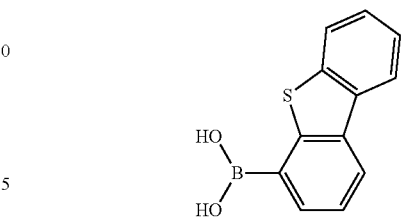

E42

-continued

E43

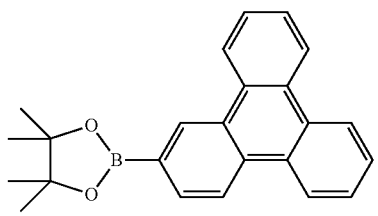

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=636.88, calculated value: $C_{48}H_{28}S=636.19$.

The energy gap of Example Compound C4 was measured by the following process:

Example Compound C4 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound C4 was determined to be 3.1 eV from the absorption edge of the resulting absorption spectrum.

Example 28

Synthesis of Example Compound C6

Example Compound C6 was prepared as in Example 1 except that Compound E44 shown below was used in place of Compound E5 in Example 1, (3).

[Chem. 55]

E44

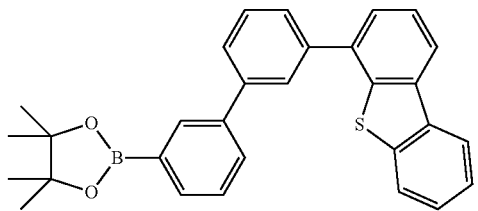

This compound was confirmed by HPLC to have a purity of 99% or more.

The resulting compound was identified as follows: [MALDI-TOF-MS (matrix-assisted laser desorption-ionization time-of-flight mass spectrometry) (Autoflex LRF manufactured by Bruker Corporation)]
Observed value: m/z=562.68, calculated value: $C_{42}H_{26}S=562.18$.

The energy gap of Example Compound C6 was measured by the following process:

Example Compound C6 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The band gap of Example Compound C6 was determined to be 3.2 eV from the absorption edge of the resulting absorption spectrum.

Example 29

In this Example, an organic light-emitting device in which an anode, a hole-transporting layer, an electron-blocking layer, a light-emitting layer, a hole/exciton-blocking layer, an electron-transporting layer, and a cathode were disposed on a substrate in this order was produced.

An ITO film having a thickness of 100 nm was formed on a glass substrate. The ITO film was patterned into a desired shape to form an ITO electrode (anode). The substrate thus provided with the ITO electrode was used as an ITO substrate in the following processes.

On this ITO substrate, organic compound layers and electrode layers shown in Table 6 were sequentially formed. On this occasion, the area where the electrodes (the metal electrode layer and the cathode) facing each other was adjusted to be 3 $mm^2$.

TABLE 6

| | Material | Thickness (nm) |
|---|---|---|
| Hole-transporting layer: G1 | H27 | 30 |
| Electron-blocking layer: G2 | H29 | 10 |
| Light-emitting layer | Example Compound A9 | 30 |
| Host: G3 | (host) | |
| Assist: G4 | GD6 (assist) | |
| Guest: G5 | RD3 (guest) | |
| | (H8:GD6:RD3 = 80:15:5 | |
| | (weight ratio)) | |
| Hole-blocking layer: G6 | H5 | 10 |
| Electron-transporting layer: G7 | H17 | 30 |
| First metal electrode layer | LiF | 1 |
| Second metal electrode layer | Al | 100 |

The characteristics of the resulting device were measured and evaluated. The light-emitting device had a maximum emission wavelength of 620 nm and a chromaticity of (X, Y)=(0.68, 0.32). Specifically, current-voltage characteristics were measured with a microammeter, 4140B, manufactured by Hewlett-Packard Company, and the luminance was measured with a luminance meter, BM7, manufactured by Topcon Corp.

The results of the measurement showed that the emission efficiency at a voltage of 4 V was 12 cd/A and the luminance half-life at a current value of 100 $mA/cm^2$ was 500 hours.

Examples 30 and 31

Comparative Examples 1 to 3

Organic light-emitting devices were produced as in Example 29 except that the compounds shown in Table 7 were used instead of G1 to G7 in Example 29. The resulting devices were subjected to measurement and evaluation of characteristics as in Example 29.

The results of the measurement are shown in Table 7. In Table 7, in the case where G3 and G4 are the same material, the host material and the assist material are the same.

TABLE 7

|  | G1 | G2 | G3 | G4 | G5 | G6 | G7 | Emission efficiency (cd/A) | Half-life (h) |
|---|---|---|---|---|---|---|---|---|---|
| Example 30 | H27 | H29 | A48 | A48 | RD3 | H5 | H17 | 12 | 400 |
| Example 31 | H27 | H29 | B1 | B1 | RD3 | H5 | H17 | 12 | 320 |
| Comparative Example 1 | H27 | H29 | (2) | (2) | RD3 | H5 | H17 | 2 | 2 |
| Comparative Example 2 | H27 | H29 | (3) | (3) | RD3 | H5 | H17 | 10 | 30 |
| Comparative Example 3 | H27 | H29 | (4) | (4) | RD3 | H5 | H17 | 11 | 90 |

In contrast, the device half-life of each of the light-emitting devices including Comparative Compound (2), (3), or (4) was short. This is caused by aryl groups introduced into positions other than the 3- and 9-positions. That is, a light-emitting device with a long lifetime and being stable can be provided by introducing aryl groups only at 3- and 9-positions.

Examples 32 to 46

Organic light-emitting devices were produced as in Example 29 except that the compounds shown in Table 8 were used instead of G1 to G7 in Example 29. The resulting devices were subjected to measurement and evaluation of characteristics as in Example 29. The results of the measurement are shown in Table 8.

In Table 8, in the case where G3 and G4 are the same material, the host material and the assist material are the same. RD1, RD2, and GD4 as the G5 material are fluorescent materials.

TABLE 8

|  | G1 | G2 | G3 | G4 | G5 | G6 | G7 | Emission efficiency (cd/A) | Emission color |
|---|---|---|---|---|---|---|---|---|---|
| Example 32 | H27 | H29 | A11 | A11 | RD3 | H5 | H17 | 12 | red |
| Example 33 | H27 | H29 | A12 | GD6 | RD5 | H5 | H17 | 13 | red |
| Example 34 | H28 | H29 | A15 | GD6 | RD7 | H5 | H17 | 13 | red |
| Example 35 | H27 | H31 | A16 | A16 | RD5 | H5 | H17 | 13 | red |
| Example 36 | H27 | H31 | A27 | A27 | RD8 | B2 | H17 | 15 | red |
| Example 37 | H27 | H29 | A65 | H27 | RD3 | A11 | H17 | 12 | red |
| Example 38 | H28 | H29 | A70 | H15 | RD2 | A11 | H17 | 7 | red |
| Example 39 | H28 | H29 | A82 | GD6 | RD4 | A11 | H17 | 13 | red |
| Example 40 | H28 | H29 | A87 | A87 | RD1 | H17 | H17 | 5 | red |
| Example 41 | H27 | H30 | B2 | GD6 | RD6 | H5 | H17 | 14 | red |
| Example 42 | H27 | H31 | B12 | B12 | RD5 | H5 | H17 | 13 | red |
| Example 43 | H27 | H31 | B16 | B16 | RD3 | H5 | H17 | 11 | red |
| Example 44 | H27 | H31 | B18 | B18 | GD2 | H5 | H17 | 16 | green |
| Example 45 | H27 | H31 | B28 | B28 | RD1 | H5 | H17 | 5 | red |
| Example 46 | H35 | H30 | C4 | GD6 | RD5 | H5 | H17 | 13 | red |

Example 47

In this Example, an organic light-emitting device in which an anode, a hole-injecting layer, a hole-transporting layer, a light-emitting layer, an electron-transporting layer, an electron-injecting layer, and a cathode were disposed on a substrate in this order was produced. The organic light-emitting device produced in this Example had a resonance structure.

First, a film serving as a reflective anode having a thickness of 100 nm was formed on a glass substrate (support) by sputtering an aluminum alloy (AlNd).

Then, a film serving as a transparent anode having a thickness of 80 nm was formed on the reflective anode by sputtering ITO.

Furthermore, a device isolation acrylic film having a thickness of 1.5 μm was formed at the periphery of the anode, and an opening having a radius of 3 mm was formed by patterning.

The substrate provided with the anode was washed by ultrasonic cleaning with acetone and then isopropyl alcohol (IPA) and then washed by boiling in IPA, followed by drying. Furthermore, the surface of the substrate was washed with UV/ozone.

Then, organic compound layers shown in Table 9 were sequentially formed on the ITO substrate by resistance heating vacuum vapor deposition in a vacuum chamber of $1 \times 10^{-5}$ Pa.

TABLE 9

|  | Material | Thickness (nm) |
|---|---|---|
| Hole-transporting layer: G8 | H27 | 95 |
| Electron-blocking layer: G9 | H29 | 10 |
| Light-emitting layer Host: G10 Guest: G11 | Example Compound A18 (host) BD7 (guest) (A18:BD7 = 98:2 (weight ratio)) | 30 |
| Electron-transporting layer: G12 | H21 | 10 |
| Electron-injecting layer: G13 | H17 Li (H17:Li = 80:20 (weight ratio)) | 70 |

Then, a film serving as a cathode having a thickness of 30 nm was formed on the electron-injecting layer by sputtering ITO. Lastly, sealing was performed in a nitrogen atmosphere.

Thus, an organic light-emitting device was produced.

The characteristics of the resulting device were measured and evaluated. Specifically, current-voltage characteristics were measured with a microammeter, 4140B, manufactured by Hewlett-Packard Company, and luminance was measured with a luminance meter, BM7, manufactured by Topcon Corp.

The results of the measurement showed that the emission efficiency at a voltage of 4 V was 4 cd/A and the emission color was blue.

Examples 48 to 52

Organic light-emitting devices were produced as in Example 47 except that the compounds shown in Table 10 were used instead of G10, G11, and G12 in Example 47.

The resulting devices were subjected to measurement and evaluation of characteristics as in Example 47. The results of the measurement are shown in Table 10.

TABLE 10

| | G8 | G9 | G10 | G11 | G12 | G13 | Emission efficiency (cd/A) | Emission color |
|---|---|---|---|---|---|---|---|---|
| Example 48 | H27 | H29 | A10 | BD8 | H5 | H17 | 4 | blue |
| Example 49 | H27 | H29 | A69 | BD6 | H5 | H17 | 3 | blue |
| Example 50 | H27 | H29 | B33 | BD5 | H5 | H17 | 4 | blue |
| Example 51 | H27 | H29 | B38 | BD7 | H5 | H17 | 4 | blue |
| Example 52 | H27 | H29 | C4 | BD4 | H5 | H17 | 4 | blue |

Examples 53

In this Example, an organic light-emitting device in which an anode, a hole-transporting layer, a first light-emitting layer, a second light-emitting layer, a hole/exciton-blocking layer, an electron-transporting layer, and a cathode were disposed on a substrate in this order was produced. The organic light-emitting device in this Example had a plurality of light-emitting layers.

First, an ITO film having a thickness of 100 nm was formed on a glass substrate and was formed into an ITO electrode (anode) by patterning. The substrate thus provided with the ITO electrode was used as an ITO substrate in the following steps.

Then, organic compound layers and electrode layers shown in Table 11 were sequentially formed on the ITO substrate by resistance heating vacuum vapor deposition in a vacuum chamber of $1 \times 10^{-5}$ Pa. On this occasion, the area where the electrodes (the metal electrode layer and the cathode) facing each other was adjusted to be 3 mm$^2$.

TABLE 11

| | Material | Thickness (nm) |
|---|---|---|
| Hole-transporting layer: G8 | H27 | 30 |
| Electron-blocking layer: G9 | H29 | 10 |
| First light-emitting layer | Example Compound B36 (first host) | 20 |

TABLE 11-continued

| | Material | Thickness (nm) |
|---|---|---|
| | GD4 (first guest) | |
| | RD2 (second guest) | |
| | (B36:GD4:RD2 = 60:39.5:0.5 (weight ratio)) | |
| Second light-emitting layer | Example Compound A70 (second host) | 20 |
| | BD7 (third guest) | |
| | (A70:BD7 = 96:4 (weight ratio)) | |
| Hole-blocking layer: G6 | H21 | 10 |
| Electron-transporting layer: G7 | H17 | 30 |
| First metal electrode layer | LiF | 1 |
| Second metal electrode layer | Al | 100 |

The characteristics of the resulting device were measured and evaluated. Specifically, current-voltage characteristics were measured with a microammeter, 4140B, manufactured by Hewlett-Packard Company, and luminance was measured with a luminance meter, BM7, manufactured by Topcon Corp.

The results of the measurement showed that the organic light-emitting device had an emission efficiency of 10 cd/A at a voltage of 4 V and emitted white light with a chromaticity of (X, Y)=(0.31, 0.33).

As described by Examples, the organic compound having a chrysene skeleton according to the embodiment has substituents at the 3- and 9-positions only of the chrysene skeleton and thereby has a high binding energy level and a shallow HOMO level when it is applied to a light-emitting device, resulting in an improvement in the device characteristics of the light-emitting layer. As a result, the device can be stable and have a long lifetime.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-220406, filed Oct. 2, 2012, which is hereby incorporated by reference herein in its entirety.

INDUSTRIAL APPLICABILITY

The organic compound according to the present invention is a highly stable compound and can provide a device having a long device lifetime when it is used as a host material of an organic light-emitting device.

REFERENCE SIGNS LIST

8 TFT device
11 anode
12 organic compound layer
13 cathode

The invention claimed is:
1. An organic light emitting device comprising:
a pair of electrodes; and
an organic compound layer disposed between the pair of electrodes, wherein
the organic compound layer includes an organic compound represented by the following formula (1):

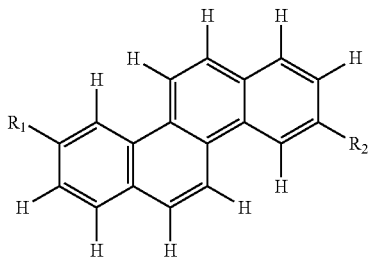
(1)

wherein $R_1$ and $R_2$ each independently selected from a hydrogen atom, Substituent group A shown below, and Substituent group B shown below, wherein

- at least one of $R_1$ and $R_2$ is selected from Substituent group A or Substituent group B;
- $R_{11}$ and $R_{12}$ of a substituent belonging to Substituent group A are each independently selected from Substituent group B; and
- each substituent belonging to Substituent group A or Substituent group B optionally has a halogen atom, a substituted or unsubstituted alkyl group, a substituted or unsubstituted alkoxy group, a silyl group, or a cyano group at a position other than the $R_{11}$ and $R_{12}$ substitution positions:

A: 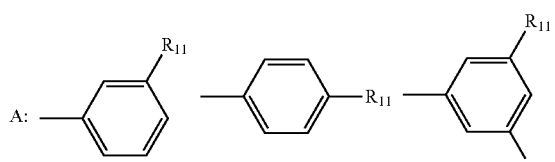

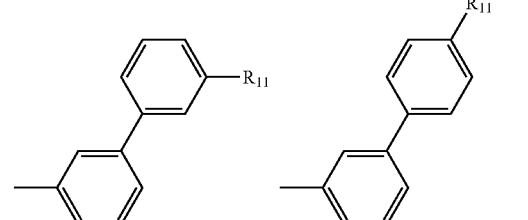

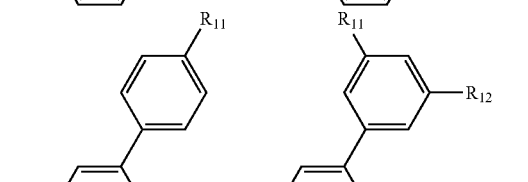

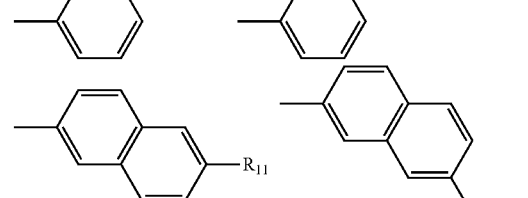

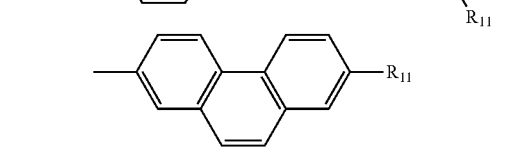

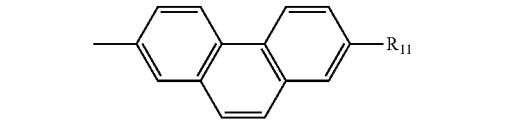

-continued

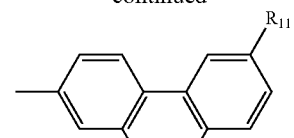

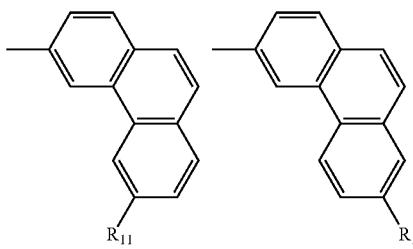

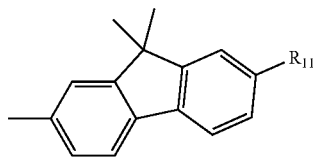

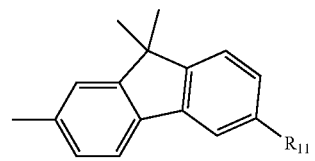

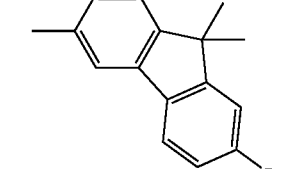

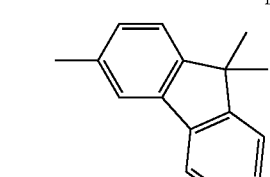

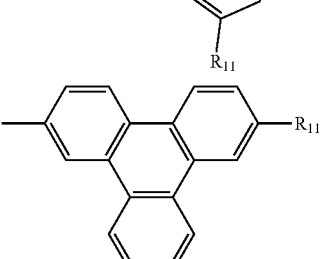

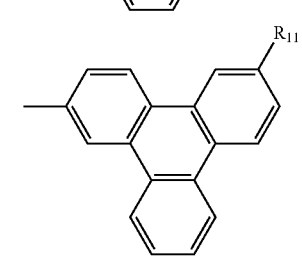

117
-continued

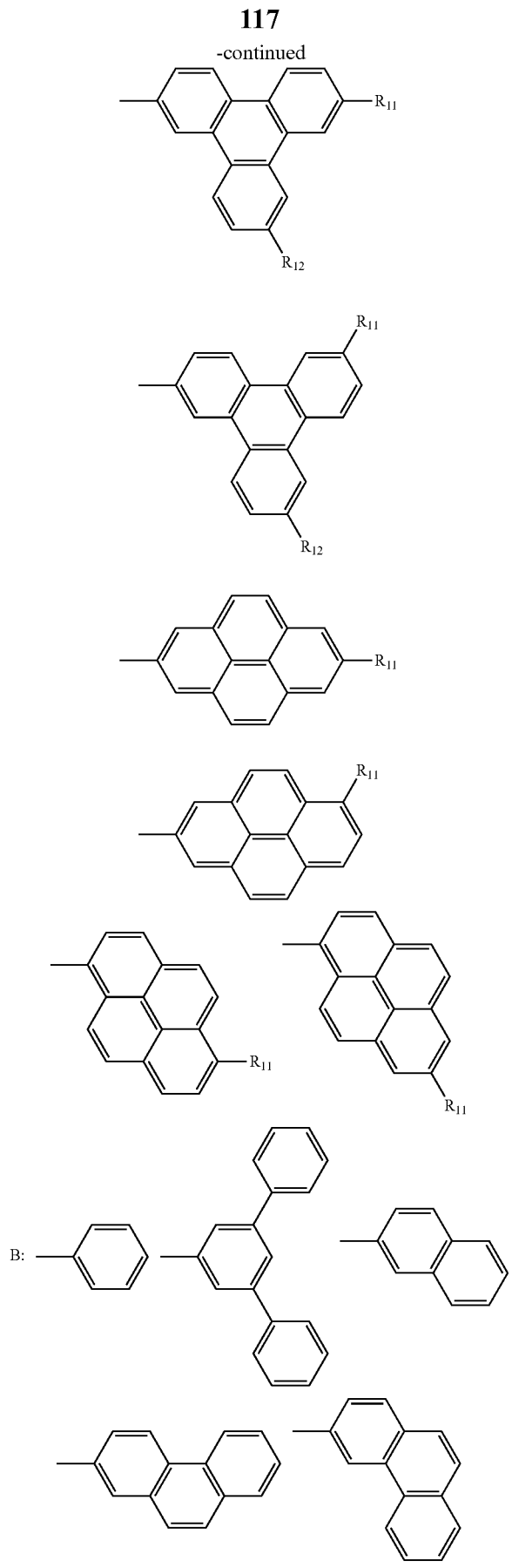

118
-continued

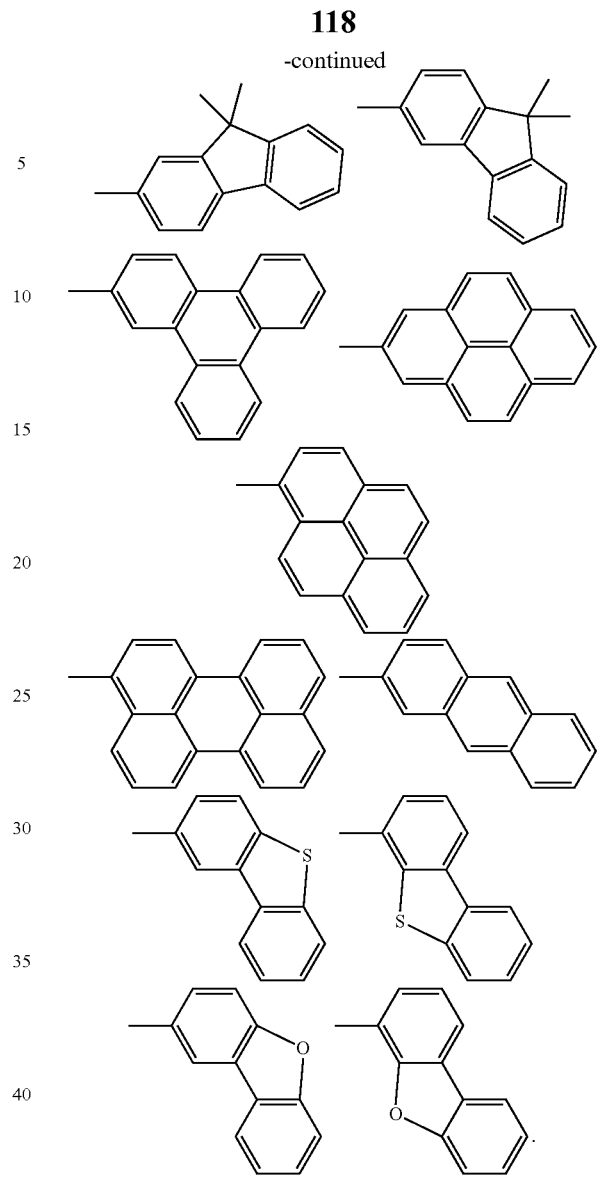

2. The organic light-emitting device according to claim 1, wherein the substituent belonging to Substituent group B has a tertiary butyl group as a substituent.

3. The organic light-emitting device according to claim 1, wherein
the organic compound layer includes a first light-emitting layer, the first light-emitting layer comprising the organic compound.

4. The organic light-emitting device according to claim 3, wherein
the first light-emitting layer includes a host material and a guest material, and the host material comprises the organic compound.

5. The organic light-emitting device according to claim 4, wherein the first light-emitting layer further includes an assist material.

6. The organic light-emitting device according to claim 5, wherein
the organic compound layer further includes a second light-emitting layer laminated on the first light-emitting layer, wherein the first and the second light-emitting layers emit light of colors different from each other; and the device emits white light.

7. The organic light-emitting device according to claim 4, wherein the organic compound layer further includes a second light-emitting layer laminated on the first light-emitting layer, wherein the first and the second light-emitting layers emit light of colors different from each other; and the device emits white light.

8. The organic light-emitting device according to claim 4, wherein the guest material comprises a phosphorescent material.

9. The organic light-emitting device according to claim 8, wherein the phosphorescent material is Ir(ppy)3 and Ir(piq)3.

10. The organic light-emitting device according to claim 3, wherein the organic compound layer has a light-emitting portion containing a plurality of light-emitting materials;

the plurality of light-emitting materials emit light of colors different from each other; and the device emits white light.

11. A display apparatus comprising:

a plurality of pixels, wherein the pixels each at least include an organic light-emitting device according to claim 3 and an active device connected to the organic light-emitting device.

12. An image information processing apparatus comprising:

an image input section for inputting image information, and a display section for displaying an image, wherein the display section includes a display apparatus according to claim 11.

13. The display apparatus according to claim 11, further comprising:

a substrate, wherein the active device is integrated on the substrate.

14. A lighting system comprising:

organic light-emitting device according to claim 3, and a converter circuit for supplying a drive voltage to the organic light-emitting device.

15. An image forming apparatus comprising:

a photosensitive member, a charging unit for charging the photosensitive member, an exposure unit for exposing the photosensitive member to light, and a developing unit for developing an electrostatic latent image formed on a surface of the photosensitive member, wherein the exposure unit includes an organic light-emitting device according to claim 3.

16. An exposure machine for exposing a photosensitive member to light, the machine comprising:

organic light-emitting devices according to claim 3, wherein the organic light-emitting devices are arranged in a line.

* * * * *